(12) United States Patent
Wortzman et al.

(10) Patent No.: US 8,268,804 B2
(45) Date of Patent: *Sep. 18, 2012

(54) MINOCYCLINE ORAL DOSAGE FORMS FOR THE TREATMENT OF ACNE

(75) Inventors: Mitchell Wortzman, Scottsdale, AZ (US); R. Todd Plott, Briscoe, TX (US); Kuljit Bhatia, Nesconset, NY (US); Bhiku Patel, Chandler, AZ (US)

(73) Assignee: Medicis Pharmaceutical Corporation, Scottsdale, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 12/875,876

(22) Filed: Sep. 3, 2010

(65) Prior Publication Data

US 2010/0330131 A1 Dec. 30, 2010

Related U.S. Application Data

(60) Division of application No. 12/253,845, filed on Oct. 17, 2008, now Pat. No. 7,790,705, which is a continuation of application No. 11/695,513, filed on Apr. 2, 2007, and a continuation of application No. 11/695,514, filed on Apr. 2, 2007, and a continuation of application No. 11/695,528, filed on Apr. 2, 2007, now Pat. No. 7,541,347, and a continuation of application No. 11/695,541, filed on Apr. 2, 2007, and a continuation of application No. 11/695,539, filed on Apr. 2, 2007, now Pat. No. 7,544,373, and a continuation-in-part of application No. 11/166,817, filed on Jun. 24, 2005, now Pat. No. 7,919,483.

(51) Int. Cl.
*A61K 9/16* (2006.01)
*A61K 9/50* (2006.01)
*A61K 9/54* (2006.01)
*A61K 9/52* (2006.01)
*A61K 31/65* (2006.01)

(52) U.S. Cl. ........ 514/152; 424/482; 424/457; 424/458; 424/455; 424/474; 424/490; 424/495; 424/497; 424/489; 424/498

(58) Field of Classification Search .................. 424/482, 424/457, 458, 455, 474, 490, 497, 495, 489, 424/498; 514/152
See application file for complete search history.

(56) References Cited

U.S. PATENT DOCUMENTS

| | | |
|---|---|---|
| 3,932,615 A | 1/1976 | Ito et al. |
| 3,957,980 A | 5/1976 | Noseworthy |
| 3,966,922 A | 6/1976 | Okamoto et al. |

(Continued)

FOREIGN PATENT DOCUMENTS

CA 2025703 9/1990

(Continued)

OTHER PUBLICATIONS

Office Communication dated Mar. 31, 2010 in U.S. Appl. No. 11/776,669.

(Continued)

*Primary Examiner* — Savitha Rao
(74) *Attorney, Agent, or Firm* — Ohlandt, Greeley, Ruggiero & Perle, L.L.P.

(57) ABSTRACT

Minocycline oral dosage forms containing a controlled release carrier are useful for the treatment of acne.

14 Claims, 14 Drawing Sheets

U.S. PATENT DOCUMENTS

| | | | |
|---|---|---|---|
| 4,086,332 A | 4/1978 | Armstrong | |
| 4,126,680 A | 11/1978 | Armstrong | |
| 4,138,475 A | 2/1979 | McAinsh et al. | |
| 4,369,172 A | 1/1983 | Schor et al. | |
| 4,376,118 A | 3/1983 | Daher et al. | |
| 4,443,442 A | 4/1984 | Skillern | |
| 4,701,320 A | 10/1987 | Hasegawa et al. | |
| 4,764,377 A | 8/1988 | Goodson | |
| 4,792,448 A | 12/1988 | Ranade | |
| 4,806,529 A | 2/1989 | Levy | |
| 4,837,030 A | 6/1989 | Valorose, Jr. et al. | |
| 4,925,833 A | 5/1990 | McNamara et al. | |
| 4,935,411 A | 6/1990 | McNamara et al. | |
| 4,935,412 A | 6/1990 | McNamara et al. | |
| 4,960,913 A | 10/1990 | Szalay et al. | |
| 5,007,790 A | 4/1991 | Shell | |
| 5,009,895 A | 4/1991 | Lui | |
| 5,122,519 A | 6/1992 | Ritter | |
| 5,167,964 A | 12/1992 | Muhammad et al. | |
| 5,188,836 A | 2/1993 | Muhammad et al. | |
| 5,202,128 A | 4/1993 | Morella et al. | |
| 5,209,978 A | 5/1993 | Kosaka et al. | |
| 5,211,958 A | 5/1993 | Akkerboom et al. | |
| 5,217,493 A | 6/1993 | Raad et al. | |
| 5,230,895 A | 7/1993 | Czarnecki et al. | |
| 5,262,173 A | 11/1993 | Sheth et al. | |
| 5,277,916 A | 1/1994 | Dwyer et al. | |
| 5,283,065 A | 2/1994 | Doyon et al. | |
| 5,300,304 A | 4/1994 | Sheth et al. | |
| 5,324,751 A | 6/1994 | DuRoss | |
| 5,348,748 A | 9/1994 | Sheth et al. | |
| 5,413,777 A | 5/1995 | Sheth et al. | |
| 5,459,135 A | 10/1995 | Golub et al. | |
| 5,518,730 A | 5/1996 | Fuisz | |
| 5,554,654 A | 9/1996 | Yu et al. | |
| 5,582,837 A | 12/1996 | Shell | |
| 5,665,776 A | 9/1997 | Yu et al. | |
| 5,674,539 A | 10/1997 | Tomas | |
| 5,698,593 A | 12/1997 | Peck | |
| 5,776,489 A | 7/1998 | Preston et al. | |
| 5,780,049 A | 7/1998 | Dickner et al. | |
| 5,783,212 A | 7/1998 | Fassihi et al. | |
| 5,789,395 A | 8/1998 | Amin et al. | |
| 5,800,836 A | 9/1998 | Morella et al. | |
| 5,814,331 A | 9/1998 | Holen | |
| 5,824,343 A | 10/1998 | Ng et al. | |
| 5,834,450 A | 11/1998 | Su | |
| 5,855,904 A | 1/1999 | Chung et al. | |
| 5,908,838 A | 6/1999 | Gans | |
| 5,972,389 A | 10/1999 | Shell et al. | |
| 6,015,804 A | 1/2000 | Golub et al. | |
| 6,087,382 A | 7/2000 | Bonner, Jr. et al. | |
| 6,120,803 A | 9/2000 | Wong et al. | |
| 6,165,513 A | 12/2000 | Dansereau et al. | |
| 6,165,999 A | 12/2000 | Vu | |
| 6,194,000 B1 | 2/2001 | Smith et al. | |
| 6,340,475 B2 | 1/2002 | Shell et al. | |
| 6,340,476 B1 | 1/2002 | Midha et al. | |
| 6,429,204 B1 | 8/2002 | Golub et al. | |
| 6,455,583 B1 | 9/2002 | Pflugfelder et al. | |
| 6,497,902 B1 | 12/2002 | Ma | |
| 6,585,997 B2 | 7/2003 | Moro et al. | |
| 6,638,922 B2 | 10/2003 | Ashley et al. | |
| 6,667,060 B1 | 12/2003 | Vandecruys et al. | |
| 6,673,843 B2 | 1/2004 | Arbiser | |
| 6,863,830 B1 | 3/2005 | Purdy et al. | |
| 6,958,161 B2 | 10/2005 | Hayes et al. | |
| 7,008,631 B2 | 3/2006 | Ashley | |
| 7,211,267 B2 | 5/2007 | Ashley | |
| 7,541,347 B2 | 6/2009 | Wortzman et al. | 514/152 |
| 7,544,373 B2 | 6/2009 | Wortzman et al. | |
| 7,790,705 B2 | 9/2010 | Wortzman et al. | |
| 7,919,483 B2 | 4/2011 | Wortzman et al. | |
| 7,976,870 B2 | 7/2011 | Berner et al. | |
| 2002/0015731 A1 | 2/2002 | Appel et al. | |
| 2002/0044968 A1 | 4/2002 | van Lengerich | |
| 2003/0044446 A1 | 3/2003 | Moro et al. | |
| 2003/0082120 A1 | 5/2003 | Milstein | |
| 2003/0130240 A1 | 7/2003 | Ashley | |
| 2003/0139380 A1 | 7/2003 | Ashley | |
| 2003/0199480 A1 | 10/2003 | Hayes et al. | |
| 2003/0229055 A1 | 12/2003 | Ashley | |
| 2004/0002481 A1 | 1/2004 | Ashley et al. | |
| 2004/0115261 A1 | 6/2004 | Ashley | |
| 2004/0127471 A1 | 7/2004 | Reisberg | |
| 2004/0185105 A1 | 9/2004 | Berner et al. | |
| 2004/0228912 A1 | 11/2004 | Chang et al. | |
| 2005/0136107 A1 | 6/2005 | Patel et al. | |
| 2005/0148552 A1 | 7/2005 | Ryan et al. | |
| 2006/0293290 A1 | 12/2006 | Wortzman et al. | |
| 2007/0154547 A1 | 7/2007 | Flanner et al. | |
| 2007/0254855 A1 | 11/2007 | Wortzman et al. | |
| 2007/0259039 A1 | 11/2007 | Wortzman et al. | |
| 2007/0270390 A1 | 11/2007 | Wortzman et al. | |
| 2007/0275933 A1 | 11/2007 | Wortzman et al. | |
| 2008/0070872 A1 | 3/2008 | Wortzman et al. | |
| 2008/0161273 A1 | 7/2008 | Arsonnaud et al. | |
| 2008/0241197 A1 | 10/2008 | Wortzman et al. | |
| 2008/0241235 A1 | 10/2008 | Wortzman et al. | |
| 2008/0241236 A1 | 10/2008 | Wortzman et al. | |
| 2008/0241241 A1 | 10/2008 | Wortzman et al. | |
| 2008/0242641 A1 | 10/2008 | Wortzman et al. | |
| 2008/0242642 A1 | 10/2008 | Wortzman et al. | |
| 2008/0260824 A1 | 10/2008 | Nangia et al. | |
| 2008/0318910 A1 | 12/2008 | Desjardins et al. | |
| 2010/0035846 A1 | 2/2010 | Wortzman et al. | |
| 2010/0215744 A1 | 8/2010 | Watt et al. | |
| 2012/0028929 A1 | 2/2012 | Power et al. | |

FOREIGN PATENT DOCUMENTS

| | | |
|---|---|---|
| CA | 2068366 | 11/1992 |
| CA | 2090561 | 2/1993 |
| CN | 101822650 A | 9/2010 |
| CN | 101836961 A | 9/2010 |
| EP | 0184389 | 6/1986 |
| EP | 0418565 | 3/1991 |
| EP | 0558913 | 9/1992 |
| GB | 2414668 | 12/2005 |
| GB | 2 420 708 A | 7/2006 |
| JP | 020064374 A | 1/1990 |
| WO | WO 93/18755 | 9/1993 |
| WO | WO 98/11879 | 3/1998 |
| WO | WO 98/55107 | 12/1998 |
| WO | WO 99/58131 | 11/1999 |
| WO | WO 02/080932 | 10/2002 |
| WO | WO 03/088906 | 10/2003 |
| WO | WO 2004/012700 | 2/2004 |
| WO | WO 2004/078111 A2 | 9/2004 |
| WO | WO 2004/091483 A2 | 10/2004 |
| WO | WO 2007/038867 A0 | 4/2007 |
| WO | WO 2007/102447 A1 | 9/2007 |
| WO | WO 2008/102161 A2 | 8/2008 |
| WO | WO 2010/033800 A2 | 3/2010 |
| WO | WO 2010/046932 A2 | 4/2010 |

OTHER PUBLICATIONS

Office Communication dated Mar. 31, 2010 in U.S. Appl. No. 11/776,676.
Office Communication dated Mar. 31, 2010 in U.S. Appl. No. 11/776,711.
Office Communication dated Apr. 2, 2010 in U.S. Appl. No. 11/944,186.
Extended European Search Report in European Application No. 06773507.6, dated Jul. 1, 2009.
Examination Report in NZ Application No. 564093, dated Oct. 29, 2009.
Office Communication dated Nov. 6, 2009 in Chinese Pat. App. Ser. No. 2006800224203 (with English translation).
Yang, Jian, et al., LingNan Skin Disease Magazine, No. 1, p. 38 (1994) (with English translation).
Agwuh, K.N., et al., "Pharmacokinetics of the tetracyclines including glycylcyclines," J. Antimicrobial Chemotherapy vol. 58, 256-265 (Jul. 1, 2006).
American Hospital Formulary Service, AHFS Drug Information 446-448 (2003).

Cartwright, A.C., et al., "A comparison of the bioavailability of minocycline capsules and film-coated tablets," J. Antimicrobial Chemotherapy vol. 1, 317:322 (1975).

Cullen, S.I., et al., "Minocycline therapy in acne vulgaris", Cutis vol. 17, No. 6, 1208-1214 (1976).

Del Rosso, J.Q., "A status report on the use of subantimicrobial-dose doxycycline: a review of the biologic and antimicrobial effects of the tetracyclines," Cutis 118-122 (Jun. 1, 2004).

Del Rosso, J.Q., "What's new in the Medicine Cabinet?", Supplement to the Feb. 2005 Skin and Aging Conference, pp. 3-6.

dePaz, S., et al., "Severe hypersensitivity reaction to minocycline", Invest. Allergol. Clin. Immunol., vol. 9, No. 6, 403-404 (1999).

Eady, A.E., et al., "Is antibiotic resistance in cutaneous propionibacteria clinically relevant?", Amer. J. Clin. Dermatol., vol. 4, No. 12, 813-831 (2003).

Goldstein, N.S., et al., "Minocycline as a cause of drug-induced autoimmune hepatitis", Amer. J. Clin. Pathol., vol. 114, 591-598 (2000).

Gump, D.W., et al., "Side effects of minocycline: different dosage regimens," Antimicrobial Agents and Chemotherapy, vol. 12, No. 5, 642-646 (Nov. 1977).

Healy, N., et al., "Fortnightly review, acne," BMJ vol. 308, 831-833 (1994).

Johnson, B.A., et al., "Use of systemic agents in the treatment of acne vulgaris," Am. Fam Physician vol. 62,1823-1830, 1835-1836 (Oct. 15, 2000).

Lawrenson, R.A., et al., "Liver damage associated with minocycline use in acne", Drug Safety, vol. 23, No. 4, 333-349 (2000).

MacDonald, H., et al., "Pharmacokinetic studies on minocycline in man," American Cyanamid (Lederle Laboratories division) 852-861 (1973).

Shalita, A., "The integral role of topical and oral retinoids in the early treatment of acne," J. European Acad. Derm. Venereol. vol. 15, Suppl. 3, 43-49 (2001).

Office Communication dated Jun. 10, 2009 in U.S. Appl. No. 11/776,676.

Office Communication dated Jun. 10, 2009 in U.S. Appl. No. 11/695,514.

Office Communication dated Jun. 25, 2009 in U.S. Appl. No. 11/776,669.

Office Communication dated May 29, 2009 in U.S. Appl. No. 11/944,186.

Office Communication dated May 29, 2009 in U.S. Appl. No. 11/776,711.

AAI International PROCORE® Technology, referencing patents issued prior to 2000.

AAI International PROSLO™ and PROSLO™ II Tablets Technology, referencing patents issued prior to 2000.

AAI International PROSORB® Technology, referencing patents issued prior to 2000.

American Hospital Formulary Service Drug Information 88, 1988, pp. 330-331.

A Comparison of the Side Effects Produced by VECTRIN and DYNACIN After Normal Dosage. Clinical Acne Reviews, vol. 2 Oct. 1977.

Drugs.com, Drug information online, Minocin PAC product information, Aug. 2007.

International Search Report and Written Opinion dated Feb. 26, 2007, for PCT/US06/23761.

International Search Report and Written Opinion mailed Dec. 5, 2007 pp. 1-18.

Is minocycline overused in acne?, Drug and Therapeutics Bulletin. vol. 44 No. 8, 60-62, Aug. 2006.

Minocin Product Insert, Wyeth Pharmaceuticals Inc. Rev Oct. 2005. Prescribingreference.com, Prescribing Reference, Drug News—Minocin PAC for Acne (Oct. 11, 2006).

MinoPAC product information, Monthly prescribing Reference (Oct. 2006) and the product information (Aug. 2007).

Physician's Desk Reference; MINOCIN®: Minocycline Hydrochloride for Oral Use; Physician's Desk Reference, 1989, pp. 1134-1136, 43rd Edition; Edward R. Barnhard, publisher, Medical Economics Co., Inc.; Oradell, NJ.

Solodyn (Minocycline HCl Extended Release Tablets) Labeling and package insert information, submitted with a New Drug Application approved May 8, 2006.

Office Communication dated Nov. 6, 2007 in U.S. Appl. No. 11/166,817.

Office Communication dated Nov. 13, 2008 in U.S. Appl. No. 11/166,817.

Office Communication dated Nov. 6, 2007 in U.S. Appl. No. 11/776,669.

Office Communication dated Jun. 17, 2008 in U.S. Appl. No. 11/776,669.

Office Communication dated Dec. 1, 2008 in U.S. Appl. No. 11/776,669.

Office Communication dated Nov. 6, 2007 in U.S. Appl. No. 11/776,676.

Office Communication dated Aug. 8, 2008 in U.S. Appl. No. 11/776,676.

Office Communication dated Nov. 6, 2007 in U.S. Appl. No. 11/776,711.

Office Communication dated Jun. 17, 2008 in U.S. Appl. No. 11/776,711.

Office Communication dated Nov. 17, 2008 in U.S. Appl. No. 11/944,186.

Office Communication dated Dec. 24, 2008 in U.S. Appl. No. 11/695,514.

Office Communication dated Jul. 22, 2008 in U.S. Appl. No. 11/695,528.

Office Communication dated Jul. 23, 2008 in U.S. Appl. No. 11/695,539.

Office Communication dated Dec. 23, 2008 in U.S. Appl. No. 11/695,539.

Akamatsu, et al., "Effect of Doxycycline on the Generation of Reactive Oxygen Species: A Possible Mechanism of Action of Acne Therapy with Doxycycline"; Acta Derm Venereol (Stockh), 1992; 72:178-179.

Akamatsu, et al., "Effects of subminimal inhibitory concentrations of minocycline on neutrophil chemotactic factor production in comedonal bacteria, neutrophil phagocytosis and oxygen metabolism", Archives of Dermatological Research, vol. 283, 1991, pp. 524-528.

Arndt et al., "What disorders present with inflamed skin?" Cutaneous Medicine and Surgery, An Intergrated Program in Dermatology, vol. 1, pp. 470-471, 1996.

Arnold et al., Andrews' Diseases of the Skin: Clinical Dermatology, 8th Edition, p. 254, 1990.

Bikowski, "Treatment of Rosacea With Doxycycline Monohydrate", Therapeutics for the clinician, vol. 66, Aug. 2000, pp. 149-152.

Brown, et al., "Diagnosis and Treatment of Ocular Rosacea", Official Journal of American Academy of Ophthalmology, vol. 85, Aug. 1978, pp. 779-786.

Champion et al., "Disorders of the Sebaceous Glands," Textbook of Dermatology, 6th Edition, vol. 3, pp. 1958-1961, 1998.

Darrah, et al., "An open multicentre study to compare fusidic acid lotion and oral minocycline in the treatment of mild-to-moderate acne vulgaris of the face", European Journal of Clinical Research, 1996, vol. 8, pp. 97-107.

James Q. Del Rosso, Clinical Significance of Brand Versus Generic Formulations: Focus on Oral Minocycline, Cutis, vol. 77, 153-156, Mar. 2006.

James Q. Del Rosso, et al. Weight-based Dosing of a Novel Antibiotic for Moderate-to-Severe Acne Vulgaris Offers Potential for Improved Safety and Tolerability, www.millennium.com/ao/acne, Millennium CME Institute, Inc., 2006.

Dreno, et al., "Multicenter Randomized Comparative Double-Blind Controlled Clinical Trial of the Safety and Efficacy of Zinc Gluconate versus Minocyclin Hydrochloride in the Treatment of Inflammatory Acne vulgaris", Dermatology, 2001, vol. 203, pp. 135-140.

Adolfo C. Fernandez-Obregon, Azithromycin for the treatment of acne, International Journal of Dermatology 2000, 39, 45-50.

Barbara Fingleton, CMT-3 CollaGenex, Current Opinion in Investigational Drugs, vol. 4, No. 12, 1460-1467, Dec. 2003.

Fleischer, A.B. et al. Safety and Efficacy of a New Extended-Release Formulation of Minocycline. Cutis 2006; 78 (suppl 4):21-31.

Freedberg, et al., Fizpatrick's Dermatology in General Medicine, 5th Edition, vol. 1, pp. 77-78, 1999.

Freeman, et al., "Therapeutic Focus Minocycline in the treatment of acne", BJCP, Mar. 1989, vol. 43, pp. 112-114.

Gans et al. The Solubility and Complexing properties of Oxytetracycline and Tetracycline II, Journal of the American Pharmaceutical Association, Sci. Ed. 46, No. 10, Oct. 1957.

K. J. Gardner, et al., Comparison of serum antibiotic levels in acne patients receiving the standard or a modified release formulation of minocycline hydrochloride. Clinical and Experimental Dermatology, vol. 22, pp. 72-76, Jan. 1997.

Garner SE, et al., "Minocycline for acne vulgaris: efficacy and safety", (Cochrane Review), The Cochrane Library, issue 1, 2004, Chichester, UK: John Wiley & Sons, Ltd.

Gollnick, Harald, et al., "Management of Acne, A Report From a Global Alliance to Improve Outcomes in Acne", Supplement to Journal of The American Academy of Dermatology, Jul. 2003, vol. 49, No. 1, S1-38.

Golub, et al., "Tetracyclines Inhibit Connective Tissue Breakdown: New Therapeutic Implications for an Old Family of Drugs", Critical Reviews in Oral Biology and Medicine, vol. 2, No. 2, 1991, pp. 297-322.

Aditya K. Gupta et al., Solodyn (Minocycline HCI, USP) Extended-Release Tablets, LE JACQ, 291-292, Nov. Dec. 2006.

Harrison, "A comparison of doxycycline and minocycline in the treatment of acne vulgaris", Clinical and Experimental Dermatology, 1998, vol. 13, pp. 242-244.

Hersle, et al., "Minocycline in Acne Vulgaris: a Double-Blind Study", Current Therapeutic Research, Mar. 1976, vol. 19, No. 3, pp. 339-342.

Charles G. Hubbell et al. Efficacy of Minocycline Compared with Tetracycline in Treatment of Acne Vulgaris, Archives of Dermatology, vol. 118, pp. 989-992, Dec. 1982.

Illig, "Positive Side Effects of Antibiotic and Antimicrobial Substances in Therapy", Infection, vol. 7, Suppl. 6, 1979, pp. S 584-588. (with English-language translation).

Muzharul M. Islam, A Nonantibiotic Chemically Modified Tetracycline (CMT-3) Inhibits intimal Thickening, American Journal of Pathology; vol. 163, No. 4, 1557-1566, Oct. 2003.

Jonas, et al., "Minocycline", Therapeutic Drug Monitoring, vol. 4, 1982, pp. 137-145.

Kelly, et al., "Metabolism and Tissue Distribution of Radiosotopically Labeled Minocycline", Elsevier Toxicology and Applied Pharmacology, 1967, vol. 11, pp. 171-183.

Leyden, J. Introduction. Cutis 2006; 78 (suppl 4):4-5.

Leyden, James J., "Absorption of minocycline hydrochloride and tetracycline hydrochloride", J. Am. Acad. Dermatol. 12:308-312, 1985.

Leyden, James J., et al., "The antimicrobial effects in vivo of minocycline, doxycycline and tetracycline in humans", The Journal of Dermatological Treatment, Dec. 1996, vol. 7, No. 4, 223-225.

Leyden, James J., et al., "Clinical Considerations in the Treatment of Acne Vulgaris and Other Inflammatory Skin Disorders: Focus on Antibiotic Resistance", Cutis 2007 (suppl. 6), vol. 79, No. 65, 9-25.

Leyden, James J., et al., "Comparison of Tazarotene and Minocycline Maintenance Therapies in Acne Vulgaris", Archives of Dermatology, May 2006, 605-612.

Leyden, et al. 2006. New Extended-Release Minocycline. First Systemic Antibiotic Approved for the Treatment of Acne. A Supplement to Cutis, 78(4S): 1-32.

Leyden, James J., et al., "*Pseudomonas aeruginosa* Gram-Negative Folliculitis", Archives of Dermatology, 1979, vol. 115, 1203-1204.

Leyden, James J., et al., "Tetracycline and Minocycline Treatment, Effects on Skin-Surface Lipid Levels and *Propionibacterium acnes*", Archives of Dermatology, 1982, vol. 118, 19-22.

Jing Li et al., Evidence for Dissolution Rate-Limited Absorption of COL-3, a Matrix Metalloproteinase Inhibitor, Leading to the Irregular Absorption Profile in Rats after Oral Administration, Pharmaceutical Research, Vo. 19, No. 11, 1655-1662, Nov. 2002.

Bal L. Lokeshwar et al., Inhibition of Cell Proliferation, Invasion, Tumor Growth and Metastasis by an Oral Non-Antimicrobial Tetracycline Analog (COL-3) in a Metastatic Prostate Cancer Model, International Journal of Cancer: 98, 297-309 (2002).

Marks, Ronald, et al., (eds.) "Dermatologic Therapy in Current Practice", Chapter 3, 35-44 (2002).

Millar, et al., "A general practice study investigating the effect of minocycline (Minocin) 50 mg bd for 12 weeks in the treatment of acne vulgaris", The British Journal of Clinical Practice, Aug. 1987, vol. 41, No. 8, pp. 882-886.

Millar, MB, ChB., et al., "A general practice study investigating the effect of minocycline (Minocin) 50 mg bd for 12 weeks in the treatment of acne vulgaris", British Journal of Clinical Practice, vol. 41, No. 8, Aug. 1987, pp. 882-886.

Falk Ochsendorf, Systemic antibiotic therapy of acne vulgaris, Journal der Deutschen Dermatologischen Gesellschaft, 4:828-841, 2006.

Piérard-Franchimont, et al. 2002. Lymecycline and Minocycline in Inflammatory Acne. Skin Pharmacol Appl Skin Physiol, 15:112-119.

Gilbert Plott, Extended-Release Minocycline: Is Efficacy Dose-dependent in the Approved Dose Range?, Poster Presentation for the DUSA Pharmaceuticals, Inc. Medical Conferences and Trade Shows, Hawaii, Mar. 3-9, 2007.

Plott, R. T. and Wortzman, M. Key Bioavailability Features of a New Extended-Release Formulation of Minocycline Hydrochloride Tablets. Cutis 2006; 78 (suppl 4):6-10.

Allen N. Sapadin et al., Tetracyclines: Nonantibiotic properties and their clinical implications, American Academy of Dermatology, Inc., 258-265, Feb. 2006.

Richard E. B. Seftor et al, Chemically modified tetracyclines inhibit human melanoma cell invasion and metastasis, Clinical & Experimental Metastasis, vol. 16, No. 3, 217-225 (1998).

Sheehan-Dare, et al " A Double-blind Comparison of Topical Clindamycin and Oral Minocycline in the Treatment of Acne Vulgaris", Acta Derm Venereol (Stockh), 70, pp. 534-537, 1990.

Smit, "Minocycline versus Doxycycline in the Treatment of Acne vulgaris", Dermatologica, vol. 157, 1978, pp. 186-190.

Smith, Kelly, et al., "Safety of Doxycycline and Minocycline: A Systematic Review", Clinical Therapeutics, The International Peer-Reviewed Journal of Drug Therapy, vol. 27, No. 9, Sep. 2005, 1329-1342.

Stewart, D.M. et al. Dose Ranging Efficacy of New Once-Daily Extended-Release Minocycline for Acne Vulgaris. Cutis 2006; 78 (suppl 4):11-20.

Ta et al., Effects of Minocycline on the Ocular Flora of Patients with Acne Rosacea or Seborrheic Blepharitis, Cornea vol. 22(6): 545-548, 2003.

Schach Von Wittenau, et al., The Distribution of Tetracyclines in Tissues of Dogs After Repeated Oral Administration, The Journal of Pharmacology and Experimental Therapeutics, 1965, vol. 152, No. 1, pp. 164-169.

Webster, "Inflammation in acne vulgaris", Journal of the American Academy of Dermatology, vol. 33, No. 2, part 1, Aug. 1995, pp. 247-253.

Webster, et al., "Suppression of Polymorphonuclear Leukocyte Chemotactic Factor Production in *Propionibacterium acnes* by Subminimal Inhibitory Concentrations of Tetracycline, Ampicillin, Minocycline, and Erythromycin", Antimicrobial Agents and Chemotherapy, vol. 21, No. 5, May 1982, pp. 770-772.

Williams D. N., et al., Minocycline: Possible vestibular side-effects. Lancet. Sep. 28, 1974;2(7883):744-6.

Opadry II Brochure, 1990, consisting of 3 pages.

Lubrizol Pharmaceutical Bulletin 23, Oct. 29, 2008, Bioadhesion (Lubrizol Advanced Materials, Inc.), consisting of 20 pages.

Nayak, et al., "Gastroretentive Drug Delivery Systems: A Review", Asian Journal of Pharmaceutical and Clinical Research, vol. 3, Issue 1, Jan.-Mar. 2010, pp. 2-10.

"Carbopol Polymers of Pharmaceutical Drug Delivery Applictions", web pages: www.drugdeliverytech.com/ME2/dimrod.asp, Sep. 6, 2003, consisting of 3 pages.

Anlar, et al., "Physico-chemical and Bioadhesive Properties of Polyacrylic Acid Polymers", Pharmazie Apr. 1993, 48 (4): 285-287, Abstract.

"Carbopol and its Applications in Pharmaceutical Dosage Forms", webpage: www.pharmainfo.net, Oct. 27, 2007, consisting of 6 pages.

Office Action dated Mar. 4, 2010 for U.S. Appl. No. 12/253,845.

Office Action dated Nov. 17, 2009 for U.S. Appl. No. 12/253,845.

International Preliminary Report on Patentability dated Feb. 2, 2011 for International Patent Application No. PCT/US2007/008086.

Del Rosso, et al., "Current Approach to Acne Management: A Community-Based Analysis", Cutaneous Medicine for the Practitioner, vol. 83, No. 6S, Jun. 2009, p. 5-24.

Del Rosso, et al., "Optimizing Use of Oral Antibiotics in Acne Vulgaris", Dermatol Clin, 27, 2009, p. 33-42.

James Q. Del Rosso, "Recently Approved Systemic Therapies for Acne Vulgaris and Rosacea", Drug Therapy Topics, vol. 80, Aug. 2007, p. 113-120.

Torok, et al., "Long-Term Safety of a Modified-Release Forumlation of Minocycline for Treating Moderate to Severe Acne", program and abstracts of the Foundation of Reaserch and Education in Dermatology Winter Clinical Dermatology Conference; Mar. 14-18, 2008; Kapalua, Hawaii, Poster, consisting of 9 pages.

Office Action dated Oct. 18, 2011 for U.S. Appl. No. 12/536,359.

U.S. Appl. No. 12/861,424, filed Aug. 23, 2010; first name inventor: Mitchell Wortzman (filed with Non-Publication Request under 35 U.S.C. 122(b)(2)(B)(i)).

International Search Report and Written Opinion dated Oct. 1, 2009 for International Patent Application No. PCT/US2009/052873.

International Preliminary Report on Patentability dated Oct. 4, 2010 for International Patent Application No. PCT/US2009/052873.

Stanley I. Cullen, "Low-Dose Minocycline Therapy in Tetracycline-Recalcitrant Acne Vulgaris", Therapeutics for the Clinician, Jan. 1978, vol. 21, pp. 101-105.

P.M. Cohen, "A General Practice Study Investigating the Effect of Minocin 50 mg b.d. for 12 Weeks in the Treatment of Acne Vulgaris", J Int Med Res, 1985, Vol. 13, pp. 214-221.

Ralph J. Coskey, "Acne: Treatment with Minocycline", Therapeutics for the Clinician, Apr. 1976, vol. 17, pp. 799-801.

Physician's Desk Reference®, 51st Ed., 1997, Minocin® Minocycline Hydrochloride Pellet-Filled Capsules, pp. 1429-1431.

MINOCYCLINE ORAL DOSAGE FORMS FOR THE TREATMENT OF ACNE

BACKGROUND OF THE INVENTION

1. Field of the Invention

This invention relates to oral tetracycline-class antibiotic dosage forms, and in some embodiments, to controlled-release oral dosage forms of minocycline and methods of using them to treat acne.

2. Background

Acne affects large patient populations, and is a common inflammatory skin disorder which usually localizes in sebaceous areas of the body including on the face, back and chest. Fortunately, the disease usually disappears, and in the interval of months or years between onset and resolution, therapy, although not curative, can satisfactorily suppress the disease in the majority of patients.

Oral tetracycline-class antibiotics are frequently used in the treatment of acne. Tetracycline-class antibiotics are known to have some side effects. These side effects include vestibular symptoms such as vertigo, dizziness or blurred vision. These effects are sometimes disabling. See, Gould & Brookler, Arch. Otolarang. Vol. 96, p. 291 (1972); Williams et al., Lancet, Sep. 28, 1974, p. 144-45; Fanning & Gump, Arch. Intern. Med., Vol. 136, pp. 761-62 (1976). Headache and general malaise, along with gastro-intestinal symptoms such as the diarrhea, nausea, gas, or cramps may also occur. Dry nose and dry mouth are also occasionally encountered.

One of the oral tetracycline-class antibiotics used in the treatment of acne is minocycline hydrochloride. Oral dosage forms of minocycline hydrochloride are available commercially under various trade names. The Approved Drug Products with Therapeutic Equivalence Evaluations ("Orange Book") lists a number of oral dosage forms of minocycline hydrochloride that are AB-rated to the MINOCIN® brand of minocycline hydrochloride. These commercial products are immediate-release oral dosage forms of minocycline hydrochloride that have been determined by the Food and Drug Administration (FDA) to be therapeutically equivalent to the MINOCIN® brand of minocycline hydrochloride on the basis of adequate in vivo and/or in vitro evidence supporting bioequivalence.

The dosing schedule used most frequently for treating acne using currently available immediate-release oral dosage forms is 100 mg of minocycline (free base equivalent) administered twice daily, see Leyden, J. Cutis 2006; 78 (suppl 4):4-5. However, some patients experience adverse effects with currently available immediate-release oral dosage forms, leading to reduced rates of patient compliance. See Stewart, M. et al., Cutis 2006; 78 (suppl 4):11-20. U.S. Pat. No. 5,908,838, which is hereby incorporated by reference, discloses slowly dissolving dosage forms of oral tetracycline-class antibiotics, including minocycline hydrochloride, that reduce the incidence or severity of vestibular side effects resulting from the treatment of acne.

Although the development of slowly dissolving forms of minocycline hydrochloride was a significant advance in the art, there remains a long-felt need for treatments that are effective in suppressing acne but associated with fewer adverse effects than those associated with the various immediate-release oral dosage forms of minocycline hydrochloride.

SUMMARY

Various improved oral dosage forms of tetracycline-class antibiotics have now been developed. An embodiment provides controlled-release minocycline oral dosage forms that are pharmacokinetically distinct from the MINOCIN® brand of immediate-release minocycline hydrochloride. Upon administration, e.g., at minocycline free base equivalent dosages in the range of about 0.75 mg/kg to about 1.5 mg/kg, embodiments provide substantially similar or better acne treatment efficacy and/or reduced incidence of at least one adverse effect, as compared to administration of the MINOCIN® immediate-release dosage form. In an embodiment, administration on a once-daily basis is effective. In some embodiments, administration without food is effective.

An embodiment provides an oral dosage form, comprising: minocycline or a pharmaceutically acceptable salt thereof; and an amount of a controlled-release carrier composition that is effective to render said oral dosage form pharmacokinetically distinct from MINOCIN® immediate-release minocycline hydrochloride. Another embodiment provides a method of treating acne, comprising administering such an oral dosage form to a subject in need thereof. Another embodiment provides a method of distributing minocycline, comprising: distributing such an oral dosage form; and concomitantly distributing information that the oral dosage form may cause an adverse effect. Another embodiment provides a method of making such an oral dosage form, comprising intermixing the minocycline or pharmaceutically acceptable salt thereof and the controlled-release carrier composition to form an admixture.

Another embodiment provides a method of administering an oral dosage form comprising: (i) administering to a patient an oral dosage form, which oral dosage form comprises: an oral tetracycline-class antibiotic; a fast dissolving carrier; and a slow dissolving carrier; and (ii) providing information to the patient, wherein the information comprises that the administering of the oral dosage form may cause one or more adverse effects selected from pseudomembranous colitis, hepatotoxicity, vasculitis, tissue hyperpigmentation, and anaphylaxis.

Another embodiment provides a method of distributing an oral dosage form, comprising: distributing an oral dosage form comprising an oral tetracycline-class antibiotic, a fast dissolving carrier and a slow dissolving carrier; and concomitantly distributing information that the oral dosage form may cause one or more adverse effects selected from pseudomembranous colitis, hepatotoxicity, vasculitis, tissue hyperpigmentation, and anaphylaxis.

Another embodiment provides a method of administering an oral dosage form comprising: (i) administering to a patient an oral dosage form, which oral dosage form comprises: an oral tetracycline-class antibiotic; a fast dissolving carrier; and a slow dissolving carrier; wherein the fast dissolving carrier and the slow dissolving carrier are at a weight ratio of 0.3 to 0.5 of fast dissolving carrier to slow dissolving carrier; and (ii) providing information to the patient, which information comprises that the administering of the oral dosage form may cause one or more adverse effects.

Another embodiment provides a method of distributing an oral dosage form, comprising: distributing an oral dosage form comprising an oral tetracycline-class antibiotic, a fast dissolving carrier and a slow dissolving carrier, wherein the fast dissolving carrier and the slow dissolving carrier are at a weight ratio of 0.3 to 0.5 of fast dissolving carrier to slow dissolving carrier; and concomitantly distributing information that the oral dosage form may cause one or more adverse effects.

Another embodiment provides a minocycline oral dosage form, comprising minocycline or a pharmaceutically acceptable salt thereof and an amount of a controlled-release carrier composition that is effective to provide an in vitro release rate of the minocycline or pharmaceutically acceptable salt thereof of about 90% in about 4 hours to about 6 hours. Another embodiment provides a method of treating acne, comprising administering such a minocycline oral dosage form to a subject in need thereof. Another method provides a method of distributing minocycline, comprising: distributing such a minocycline oral dosage form; and concomitantly distributing information that the minocycline may cause an adverse effect. Another embodiment provides a method of making such a minocycline oral dosage form, comprising intermixing the minocycline salt and the controlled-release carrier composition to form an admixture.

Another embodiment provides a kit, comprising any of the minocycline oral dosage forms described herein; and information that the oral dosage form may cause one or more adverse effects.

Another embodiment provides a kit comprising (i) an oral dosage form comprising: an oral tetracycline-class antibiotic; a fast dissolving carrier; and a slow dissolving carrier; wherein the fast dissolving carrier and slow dissolving carrier are at a weight ratio of 0.3 to 0.5 of fast dissolving carrier to slow dissolving carrier; and (ii) information that the oral dosage form may cause one or more adverse effects.

These and other embodiments are described in greater detail below.

DETAILED DESCRIPTION

Figure 1:
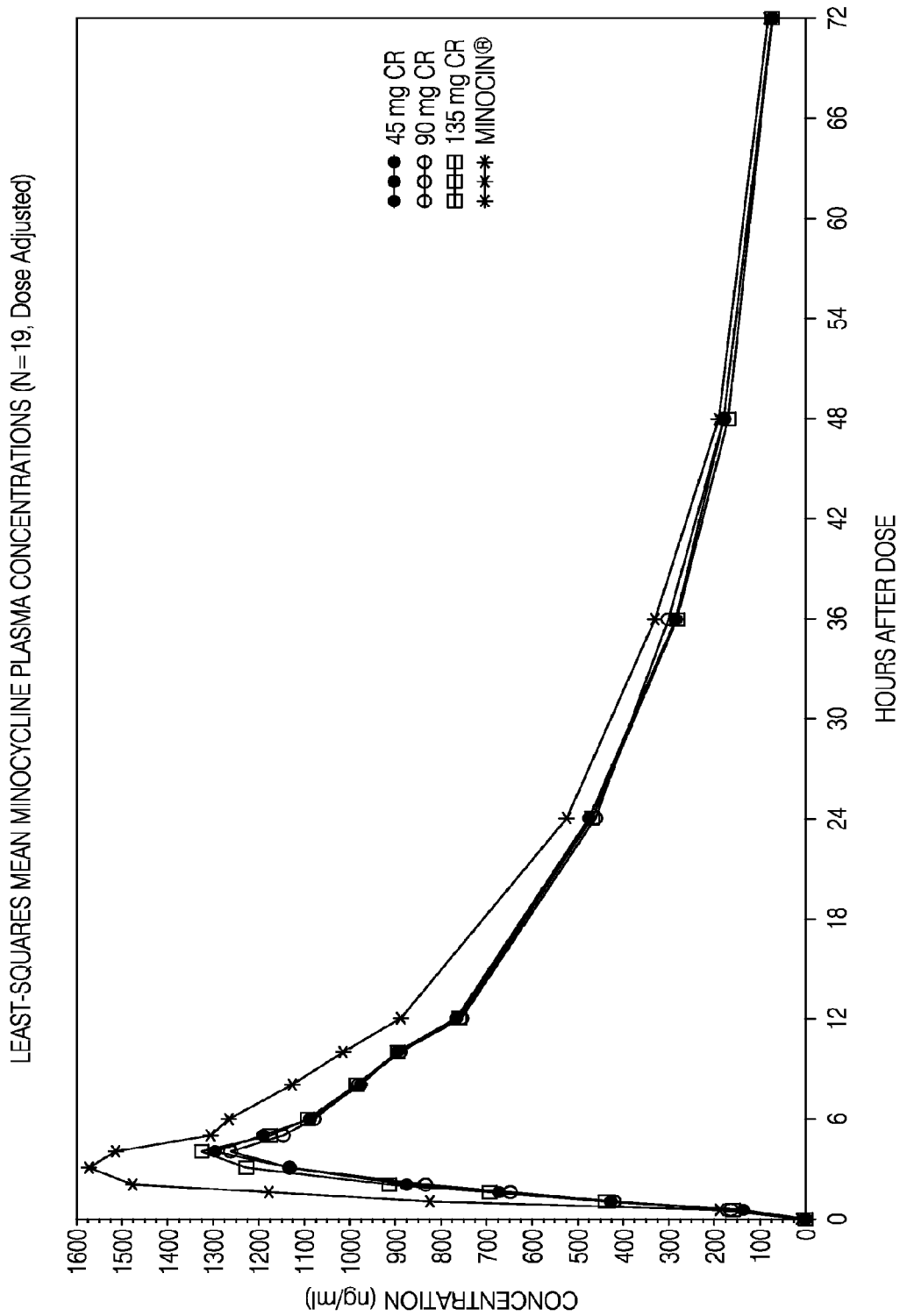
FIG. 1 is a plot showing minocycline plasma concentrations as a function of time across different dosages and formulations.

Various embodiments provide oral dosage forms in which the active ingredient is a tetracycline-class antibiotic such as minocycline. The term "active ingredient" refers to a component or mixture of components of a formulation that has a significant medicinal effect on the patient to which it is administered. For example, in some embodiments, the significant medicinal effect is a reduction in one or more symptoms associated with acne, e.g., acne vulgaris.

The term "bioequivalent" as used herein has its ordinary meaning as understood by those skilled in the art and thus includes, by way of non-limiting example, a drug or dosage form that, upon administration to a suitable patient population, provides principle pharmacokinetic parameters (AUC and $C_{max}$) that are in the range of 80% to 125% of those provided by a reference standard.

The term "pharmacokinetically distinct" as used herein refers to a drug or dosage form that, upon administration to a patient population, provides a pharmacokinetic profile that is outside the range of 80% to 125% of the reference standard. Those skilled in the art will understand that such determinations of pharmacokinetic distinctness by comparison to the reference standard are undertaken using clinical trial methods known and accepted by those skilled in the art, e.g., as described in the examples set forth herein. Since the pharmacokinetics of a drug can vary from patient to patient, such clinical trials generally involve multiple patients and appropriate statistical analyses of the resulting data (typically ANOVA at 90% confidence). Pharmacokinetic distinctness is determined on a dose-adjusted basis, as understood by those skilled in the art.

In various embodiments related to the controlled-release minocycline oral dosage forms described herein, the reference standard is an immediate-release minocycline dosage form. Those skilled in the art will understand that the immediate-release minocycline dosage form appropriate for use as the reference standard in the determination of pharmacokinetic distinctness is the legend immediate-release minocycline dosage form, widely available commercially as the MINOCIN® brand of minocycline hydrochloride. The U.S. government regulates the manner in which prescription drugs can be labeled and thus reference herein to MINOCIN® immediate-release minocycline hydrochloride has a well-known, fixed and definite meaning to those skilled in the art.

The term "pharmacokinetic profile," as used herein, has its ordinary meaning as understood by those skilled in the art and thus includes, by way of non-limiting example, a characteristic of the curve that results from plotting blood serum concentration of a drug over time, following administration of the drug to a subject. A pharmacokinetic profile thus includes a pharmacokinetic parameter or set of parameters that can be used to characterize the pharmacokinetics of a particular drug or dosage form when administered to a suitable patient population. Various pharmacokinetic parameters are known to those skilled in the art, including area under the blood plasma concentration vs. time curve (AUC), maximum blood plasma concentration after administration ($C_{max}$), time to maximum blood plasma concentration ($T_{max}$), blood plasma concentration decay half-life ($t_{1/2}$), etc. The AUC parameter may be expressed over a defined time, e.g., $AUC_{(0-24)}$ indicates the area under the blood plasma concentration vs. time curve from administration (t=0) to 24 hours after administration. Pharmacokinetic parameters may be measured in various ways known to those skilled in the art, e.g., single dosage or steady-state, as described in the examples below. The AUC parameter may be extrapolated to infinite time, e.g., $AUC_{inf}$ indicates the estimated area under the blood plasma concentration vs. time curve for all time following administration. Examples of pharmacokinetic profiles suitable for determining pharmacokinetic distinctness include those that comprise one or more of an AUC parameter, a $C_{max}$ parameter and a $T_{max}$ parameter. Other examples of pharmacokinetic parameters include in vivo plasma minocycline concentration profiles such as single-dosage $C_{max}$, steady-state $C_{max}$, single-dosage $AUC_{(0-72)}$, steady state $AUC_{(0-72)}$, single-dosage $T_{max}$, and steady state $T_{max}$, as well as pharmacokinetic parameters reported in the examples provided herein. Differences between pharmacokinetic profiles are determined using statistical methods that are known and accepted by those skilled in the art, e.g., as illustrated in the examples provided herein.

The term "dosage form", as used herein, has its ordinary meaning as understood by those skilled in the art and thus includes, by way of non-limiting example, a formulation of a drug or drugs in a form administrable to human. The illustrative embodiments of the invention have been described primarily as being directed to oral dosage forms such as tablets, cores, capsules, caplets and loose powder, but other suitable oral dosage forms such as solutions and suspensions are also contemplated.

The term "release rate", as used herein, has its ordinary meaning as understood by those skilled in the art and thus includes, by way of non-limiting example, a characteristic related to the amount of an active ingredient released per unit time as defined by in vitro or in vivo testing. An in vitro release rate is determined by a "standard dissolution test.," conducted according to United States Pharmacopeia 24th edition (2000) (USP 24), pp. 1941-1943, using Apparatus 2 described therein at a spindle rotation speed of 100 rpm and a dissolution medium of water, at 37° C., or other test conditions substantially equivalent thereto. As used herein, a release rate can define a formulation. For example, reference herein to a formulation or dosage form as a "4-hour" formulation or dosage form indicates that the point at which about 90% of the active ingredient has been released occurs within a range of about 4 hours to about 6 hours after commencement of the release test. Reference herein to a controlled-release or extended release formulation or dosage form includes such 4-hour formulations.

The term "immediate release", as used herein, has its ordinary meaning as understood by those skilled in the art and thus includes, by way of non-limiting example, release of a drug from a dosage form in a relatively brief period of time after administration. In the context of minocycline, immediate-release dosage forms are those that have a release rate that is up to and including 125% of the release rate for MINOCIN® immediate-release minocycline hydrochloride. The term "modified release", as used herein, has its ordinary meaning as understood by those skilled in the art and thus includes, by way of non-limiting example, release characteristics of time, course and/or location of the drug from the dosage form in a manner that is chosen to provide therapeutic or convenience features that are significantly different from those provided by the immediate-release form. The term "controlled release", as used herein, has its ordinary meaning as understood by those skilled in the art and thus includes, by way of non-limiting example, release of a drug from a dosage form in a pre-determined manner or according to a pre-determined condition. The term "delayed release", as used herein, has its ordinary meaning as understood by those skilled in the art and thus includes, by way of non-limiting example, release of drug at a time later than immediately after administration. The term "extended release" or "sustained release", as used herein, has its ordinary meaning as understood by those skilled in the art and thus includes, by way of non-limiting example, the controlled release of a drug from a dosage form over an extended period of time. In the context of minocycline, extended-release dosage forms are those that have a release rate that is greater than 125% of the release rate for MINOCIN® immediate-release minocycline hydrochloride, e.g., a $T_{max}$ that is greater than 125% of the $T_{max}$ for MINOCIN® immediate-release minocycline hydrochloride. The term "controlled release carrier", as used herein, has its ordinary meaning as understood by those skilled in the art and thus includes, by way of non-limiting example, an ingredient or ingredients that are included in a pharmaceutical formulation in amounts that are effective to extend the release rate of the active ingredient from the formulation as compared to an immediate-release formulation. Examples of controlled release carriers include hydroxypropylmethylcellulose, hydroxypropylcellulose, and polyvinylpyrollidone. A controlled release carrier composition may contain one or more controlled release carriers, along with other suitable ingredients.

Minocycline may be in the form of a free base, an acid salt (e.g., hydrochloride salt) or a mixture thereof. Reference herein to "minocycline" will be understood as encompassing all such forms, unless the context clearly indicates otherwise. Dosages of minocycline salts will be understood to be on the basis of the amount of minocycline free base provided thereby, and thus may be expressed as a minocycline free base equivalent dosage or amount. Minocycline salts are pharmaceutically acceptable in some embodiments. The term "pharmaceutically acceptable", as used herein, refers to a drug, salt, carrier, etc., that can be introduced safely into an animal body (e.g., taken orally and digested, etc.).

Generally, embodiments of the present invention relate to tetracycline-class antibiotic oral dosage forms and methods of administering them, e.g., for the treatment of acne. In some embodiments, the tetracycline-class antibiotic is minocycline or a pharmaceutically acceptable salt thereof and/or the oral dosage form comprises a controlled-release carrier composition. The compositions and oral dosage forms that contain a controlled-release carrier may be referred to herein in a general way as modified-release, controlled-release or extended-release compositions, e.g., to distinguish them from the immediate-release forms also described herein, to which they may be compared.

An embodiment provides an oral dosage form, comprising: minocycline or a pharmaceutically acceptable salt thereof; and an amount of a controlled-release carrier composition that is effective to render the oral dosage form pharmacokinetically distinct from MINOCIN® immediate-release minocycline hydrochloride. Illustrative controlled-release carrier compositions and methods of selecting such effective amounts and incorporating them into extended-release minocycline oral dosage forms are described in greater detail below. In some embodiments, the oral dosage form is pharmacokinetically distinct in such a way that the oral dosage form is not considered to be bioequivalent to MINOCIN® immediate-release minocycline hydrochloride.

In some embodiments, controlled-release minocycline oral dosage forms provide dosages in a minocycline free base equivalent amount selected from about 45 mg, about 60 mg, about 90 mg and about 135 mg. The selection of a particular dosage may be based on the weight of the patient. Unit dosage forms suitable for administration to a human may be configured to provide a minocycline free base equivalent dosage in the range of about 0.75 mg/kg to about 1.5 mg/kg, e.g., about 1 mg/kg (basis is mg of drug per kilogram of body weight). The controlled-release oral dosage forms described herein may be administered on a once-daily basis, with or without a loading dose.

In some embodiments, once-daily administration of the controlled-release oral dosage form provides substantially similar or better acne treatment efficacy and/or reduced incidence of at least one adverse effect, as compared to a twice-daily administration of MINOCIN® immediate-release minocycline hydrochloride. The dosing schedule used most frequently for treating acne using currently available immediate-release oral dosage forms is reported to be 100 mg of minocycline (free base equivalent) administered twice daily, see Leyden, J. Cutis 2006; 78 (suppl 4):4-5, and Fleischer, A. et al. Cutis 2006; 78 (suppl 4):21-31. Thus, once-daily administration of the controlled-release oral dosage forms described herein enables the ingestion of substantially smaller amounts of minocycline than obtained by the reported current practice using immediate-release oral dosage forms, yet in some embodiments, efficacy is substantially similar or better.

In some embodiments the compositions described herein contain an amount of a controlled-release carrier composition that is effective to render the oral dosage form pharmacokinetically distinct from a comparable composition, such as MINOCIN® immediate-release minocycline hydrochloride. For example, relative to the comparable composition, the amount and type of controlled-release carrier composition may be selected to slow the release of the drug from the oral dosage form after ingestion, thus modifying the pharmacokinetic profile of the composition. A description of representative controlled release carrier materials can be found in the Remington: The Science and Practice of Pharmacy (20$^{th}$ ed, Lippincott Williams & Wilkens Publishers (2003)), which is incorporated herein by reference in its entirety. Those skilled in the art can formulate controlled-release carrier compositions by routine experimentation informed by the detailed guidance provided herein. Examples 1-12 below describe illustrative minocycline extended-release oral dosage forms.

In an embodiment, the controlled-release carrier composition comprises one or more slow dissolving carriers and one or more fast dissolving carriers. For example, an embodiment provides an oral dosage form comprising an oral tetracycline-class antibiotic, a fast dissolving carrier and a slow dissolving carrier. The weight ratio of fast dissolving carrier(s) to slow dissolving carrier(s) in the controlled-release carrier composition may be in various ranges, e.g., the range of about 0.3 to about 0.5, the range of about 0.3 to about 0.45, or the range of about 0.36 to about 0.40. Examples of controlled-release carrier compositions are described in U.S. priority application that provides a method for the treatment of acne in which an antibiotically effective dose of an oral tetracycline, such as minocycline, is provided. This dose is approximately 1 milligram per kilogram of body weight (1 mg/kg), without an initial loading dose of antibiotic. This antibiotic dosing regimen has been found to be as effective as a conventional dosing regimen incorporating a significant initial loading dose and higher subsequent doses. However, the dosing method of the current invention produces far fewer side effects.

In another aspect of this invention, the oral tetracycline is provided in a dosage form that provides for the continued release of the antibiotic between doses, as opposed to an immediate or nearly immediate release of the drug.

According to the present invention, acne vulgaris is treated by the use of an oral tetracycline antibiotic, preferably minocycline. This antibiotic is administered in an antibiotically effective amount of approximately 1.0 milligram per kilogram of body weight per day (1.0 mg/kg/day). It is preferred that the tetracycline antibiotic be delivered in a single daily dose. This treatment regime is initiated without a loading dose, and is continued until resolution or substantial resolution of the patient's acne. The course of treatment typically lasts 12 to up to 60 weeks, but will be adjusted according to the disease status and other medical conditions of each patient in the exercise of ordinary good clinical judgment by the patient's health care provider.

Controlled, double-blinded studies were undertaken to determine the effectiveness of this invention. Treatment of 473 patients with acne was undertaken according to the present invention. Placebos were provided to 239 patients. The effectiveness of the invention in treating acne vulgaris is shown in Table A.

TABLE A

Total Lesion Counts

|  | Total Lesions | Total Lesions (as Percent of Baseline) |
|---|---|---|
| Baseline (mean) | 169.3 | 100 |
| Day 28 (mean) | 134.0 | 78 |
| Day 56 (mean) | 119.3 | 69 |
| Day 84 (mean) | 112.3 | 66 |

Inflammatory Lesion Counts

|  | Inflammatory Lesions | Inflammatory Lesions (as Percent of Baseline) |
|---|---|---|
| Baseline (mean) | 77.4 | 100 |
| Day 28 (mean) | 52.1 | 66 |
| Day 56 (mean) | 44.3 | 56 |
| Day 84 (mean) | 41.9 | 53 |

While effective as a treatment for acne, this resulted in almost no side effects above those observed with a placebo, as shown in Table B.

TABLE B

% Subjects with Adverse Events

|  | Minocycline | Placebo |
|---|---|---|
| At least One Adverse Event | 56.2 | 54.1 |
| At Least One Serious Adverse Event | 0.4 | 0 |
| Blood/Lymphatic System Disorders | 0.3 | 0.3 |
| Cardiac Disorders | 0.3 | 0 |
| Ear and Labyrinth Disorders | 3.6 | 3.3 |
| Endocrine Disorders | 0.3 | 0 |
| Eye Disorders | 2.2 | 2.7 |
| Gastrointestinal Disorders | 21.2 | 26.1 |
| General Disorders and Administrative Site Conditions | 13.8 | 10.4 |
| Immune System Disorders | 0.7 | 2.5 |
| Infections and Infestations | 9.3 | 11.0 |
| Laboratory Blood Abnormalities | 0.7 | 1.1 |
| Metabolism and Nutrition Disorders | 0.6 | 0.3 |
| Musculoskeletal and Connective Disorders | 4.6 | 3.6 |
| Neoplasms Benign, Malignant and Unspecified | 0.1 | 0 |
| Nervous System Disorders | 29.2 | 25.8 |
| Psychiatric Disorders | 6.4 | 7.1 |
| Renal and Urinary Disorders | 0.3 | 0.5 |

TABLE B-continued

% Subjects with Adverse Events

| | Minocycline | Placebo |
|---|---|---|
| Reproductive System and Breast Disorders | 0.7 | 0.3 |
| Respiratory, Thoracic and Mediastinal Disorders | 5.3 | 6.9 |
| Skin and Subcutaneous Tissue Disorders | 8.6 | 7.1 |
| Vascular Disorders | 1.0 | 0.3 |

The effectiveness of this invention can be seen by comparing the above efficacy data with published data on the effectiveness of conventional tetracycline treatments for acne in the reduction of total acne lesions and in the reduction of inflammatory lesions. See, e.g. Hersel & Gisslen, "Minocycline in Acne Vulgaris: A Double Blind Study," Current Therapeutic Research, 1976.

Because of the variations in body weight encountered in clinical practice, in the actual practice of this invention it is not practical to provide every patient with exactly 1 mg/kg/day of oral tetracycline antibiotic. However, it is acceptable to approximate this dose by providing the patient with from 0.5 to 1.5 mg/kg/day although from 0.7 to 1.3 mg/kg/day is preferred, and 1.0 mg/kg/day is ideal.

While it can be effective to provide the oral tetracycline antibiotic in divided doses taken over the course of a day (e.g. twice or three times a day), it is preferable to provide the oral tetracycline antibiotic in a dosage form that releases the antibiotic slowly during the course of a day so that once-a-day dosing is possible. While delayed release dosage forms are known in the art, the formulation of them is far from predictable and the selection of a specific delayed release formulation is accomplished more by trial and error than by mathematical prediction based on known properties of delay release agents. No delayed release product useful in the present invention has been known heretofore.

It has been discovered that the ratio of fast dissolving carriers to slow dissolving carriers in the core caplet is important in obtaining a dissolution profile that enables once-a-day dosing in accordance with the present invention. By keeping the ratio of these components within a certain range, one may obtain this result.

The fast dissolving carrier is any binder, vehicle, or excipient that quickly dissolves in an aqueous physiological medium, such as gastric fluid, thereby tending to quickly release the active ingredient. Lactose, its salts and hydrates are good examples of such components. It has been observed that sometimes a portion of the fast dissolving components are formulated in a manner that results in the complete or partial encapsulation or inclusion or coating of these fast-dissolving materials in granules of slow-dissolving materials. These encapsulated materials are excluded from the calculation of the above mentioned ratio of fast-dissolving to slow dissolving components.

A slow dissolving carrier is any binder, vehicle, or excipient that dissolves slowly over the course of hours and perhaps a day, thereby slowing the release of the active ingredient. Examples of such components are polyvinyl pyrrolidone, polyvinyl acetate, microcrystalline cellulose, methyl cellulose, ethyl cellulose, hydroxypropyl cellulose, hydroxypropylmethyl cellulose, or waxy or lipid-based tableting agents such as magnesium stearate or calcium stearate. Outer "enteric" coatings are excluded from this amount when calculating the above-mentioned ratio.

Insoluble carriers are binders, vehicles, or excipients that are practically insoluble in physiological fluids, such as gastric fluid, and includes compounds, such as silicon dioxide and talc.

While the exact formulation of these dosage forms can vary, it has been observed that it is advantageous to formulate them so that the ratio of fast dissolving carriers to slow dissolving carriers is from 0.30 to 0.50, and preferably from 0.35 to 0.45. A ratio of about 0.36 to 0.40 is particularly preferable.

Dosage forms, such as capsules, tablets, and caplets that release 25 to 52% of the antibiotics within 1 hour, 53 to 89% in 2 hours, and at least 90% within 4 hours are suited to the once-a-day dosage regimen contemplated by the current inventories. More preferably, 30 to 52% of the antibiotic is released within 1 hour, 53 to 84% within 2 hours, and at least 85% within 4 hours.

Alternatively, the oral tetracycline antibiotic may be delivered in a dosage form that releases the antibiotic in such a way that the maximum blood concentration of the antibiotic ($C_{max}$) is reached at about 3.5 hours after administration ($T_{max}$). In actual practice of the invention, the $C_{max}$ should be reached between 2.75 and 4.0 after administration, more preferably between 3.0 and 3.75 after administration.

As examples of such a once-a-day formulation, one may use the following:

| 135 mg Caplet | |
|---|---|
| Component | Quantity (mg) |
| Minocycline (as hydrochloride) (dry weight) | 145.8 |
| Lactose Monohydrate (intragranular) | 107.4 |
| Lactose Monohydrate (extragranular) | 43.8 |
| Total Lactose Monohydrate | 151.2 |
| HPMC | 94 |
| Silicon Dioxide | 3 |
| Mg. Stearate | 6 |

| 45 mg Caplet | |
|---|---|
| Component | Quantity (mg) |
| Minocycline (as hydrochloride) (dry weight) | 48.6 |
| Lactose Monohydrate (intragranular) | 192.2 |
| Lactose Monohydrate (extragranular) | 42.2 |
| Total Lactose Monohydrate | 234.40 |
| HPMC | 108 |
| Silicon Dioxide | 3 |
| Mg. Stearate | 6 |

The fast dissolving carrier is any binder, vehicle, or excipient that quickly dissolves in an aqueous physiological medium, such as gastric fluid, thereby tending to quickly release the active ingredient. Lactose, its salts and hydrates are good examples of such components. It has been observed that sometimes a portion of the fast dissolving components are formulated in a manner that results in the complete or partial encapsulation or inclusion or coating of these fast-dissolving materials in granules of slow-dissolving materials. These encapsulated materials are excluded from the calculation of the above mentioned ratio of fast-dissolving to slow dissolving components.

A slow dissolving carrier is any binder, vehicle, or excipient that dissolves slowly over the course of hours and perhaps a day, thereby slowing the release of the active ingredient. Examples of such components are polyvinyl pyrrolidone (e.g., KOLLIDON SR POLYOX), polyvinyl acetate, microcrystalline cellulose, methyl cellulose, ethyl cellulose, hydroxypropyl cellulose (e.g., KLUCEL LF, KLUCEL HXF), hydroxypropylmethyl cellulose (e.g., METHOCEL E50 PREMIUM LV, METHOCEL K100 LV), or waxy or lipid-based tableting agents such as magnesium stearate or calcium stearate. Outer "enteric" coatings are excluded from this amount when calculating the above-mentioned ratio.

In an embodiment, a 45 mg (minocycline free base equivalent) unit oral dosage form comprises minocycline hydrochloride and an amount of the controlled-release carrier in the range of about 20% to about 30%, by weight based on the total weight of the unit dosage form. For example, a 45 mg minocycline oral dosage form may comprise about 26 wt. % to about 28 wt. %, e.g., about 27%, of HYPROMELLOSE USP, Type 2910 (METHOCEL E50 PREMIUM LV).

In an embodiment, a 90 mg (minocycline free base equivalent) unit oral dosage form comprises minocycline hydrochloride and an amount of the controlled-release carrier in the range of about 20% to about 30%, by weight based on the total weight of the unit dosage form. For example, a 90 mg minocycline oral dosage form may comprise about 26 wt. % to about 28 wt. %, e.g., about 27%, of HYPROMELLOSE USP, Type 2910 (METHOCEL E50 PREMIUM LV).

In an embodiment, a 135 mg (minocycline free base equivalent) unit oral dosage form comprises minocycline hydrochloride and an amount of the controlled-release carrier in the range of about 20% to about 30%, by weight based on the total weight of the unit dosage form. For example, a 135 mg minocycline oral dosage form may comprise about 22 wt. % to less than 25 wt. %, e.g., about 23.5%, of HYPROMELLOSE USP, Type 2910 (METHOCEL E50 PREMIUM LV).

The oral dosage forms described herein may be formulated to comprise various excipients, binders, carriers, disintegrants, coatings, etc. Pharmaceutical preparations for oral use can be obtained by mixing one or more solid excipients with a pharmaceutical composition as described herein, optionally grinding the resulting mixture, and processing the mixture of granules, after adding suitable auxiliaries, if desired, to obtain pharmaceutical compositions suitable for use in various forms, e.g., as pills, tablets, powders, granules, dragees, capsules, liquids, sprays, gels, syrups, slurries, suspensions and the like, in bulk or unit dosage forms, for oral ingestion by a patient to be treated. Various examples of unit dosage forms are described herein; non-limiting examples include a pill, a tablet, a capsule, a gel cap, and the like. Examples of suitable excipients are listed below, some of which are mentioned above as having particular dissolution properties (e.g., fast dissolving or slow dissolving). Pharmaceutically acceptable carriers or diluents for therapeutic use are well known in the pharmaceutical art, and are described, for example, in Remington: The Science and Practice of Pharmacy (2003), which is hereby incorporated by reference in its entirety. The term "carrier" material or "excipient" herein can mean any substance, not itself a therapeutic agent, used as a carrier, diluent, adjuvant, binder, and/or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, saline, dextrose, mannitol, lactose, lecithin, albumin, sodium glutamate, cysteine hydrochloride, and the like. Examples of suitable excipients for soft gelatin capsules include vegetable oils, waxes, fats, semisolid and liquid polyols. Suitable excipients for the preparation of solutions and syrups include, without limitation, water, polyols, sucrose, invert sugar and glucose. The pharmaceutical compositions can additionally include preservatives, solubilizers, stabilizers, wetting agents, emulsifiers, sweeteners, colorants, flavorings, buffers, coating agents, or antioxidants. Dissolution or suspension of the active ingredient in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice. The compound can also be made in microencapsulated form. If desired, absorption enhancing preparations (for example, liposomes), can be utilized. In some embodiments oral dosage forms include one or more a sugars (lactose, lactose monohydrate, sucrose, mannitol, or sorbitol); cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); disintegrating agents such as the cross-linked polyvinyl pyrrolidone, agar, or alginic acid or a salt thereof such as sodium alginate; colloidal silicon dioxide, magnesium stearate, titanium dioxide, polyethylene glycol, triacetin, carnauba wax, microcrystalline cellulose, providone, sodium starch glycolate, corn starch, polysorbate 80, and iron oxide. Coating materials include those available commercially under the tradename OPADRY, e.g., at a level in the range of about 3.5 wt. % to about 3.9 wt. % based on total weight of the oral dosage form. Those skilled in the art can formulate controlled-release oral dosage forms containing one or more of the foregoing ingredients by routine experimentation informed by the detailed guidance provided herein.

The pharmacokinetic properties of a drug can affect both the effectiveness and the side effects of treatment. In some embodiments, administration of a tetracycline-class antibiotic composition to a suitable patient population as described herein results in one or more of a reduced maximum observed plasma minocycline concentration ($C_{max}$), a reduced area under a blood plasma minocycline concentration versus time curve (AUC), and/or an increased time ($T_{max}$) of occurrence of the maximum observed plasma minocycline concentration as compared to a comparable composition. For minocycline, the comparable composition is MINOCIN® immediate-release minocycline hydrochloride. Pharmacokinetic properties can be determined by analyzing the plasma of a patient population that has received controlled-release tetracycline-class antibiotic compositions, and comparing them to a comparable patient population that has received the comparable composition, using the appropriate clinical trial methodology and statistical analyses.

In some embodiments, the pharmacokinetic properties are single-dosage, while in others, they are steady-state. For example, in an embodiment, the oral dosage form provides, after administration, at least one in vivo plasma minocycline concentration profile selected from: (a) a single-dosage $C_{max}$ that is about 80% or less of the single-dosage $C_{max}$ of the MINOCIN® immediate-release minocycline hydrochloride; (b) a steady-state $C_{max}$ that is about 80% or less of the steady-state $C_{max}$ of the MINOCIN® immediate-release minocycline hydrochloride; (c) a single-dosage $AUC_{(0-72)}$ that is about 80% or less of the single-dosage $AUC_{(0-72)}$ of the MINOCIN® immediate-release minocycline hydrochloride; (d) a steady state $AUC_{(0-72)}$ that is about 80% or less of the steady state $AUC_{(0-72)}$ of the MINOCIN® immediate-release minocycline hydrochloride; (e) a single-dosage $T_{max}$ that is at least about 125% of the single-dosage $T_{max}$ of the MINOCIN® immediate-release minocycline hydrochloride; and (f) a steady state $T_{max}$ that is at least about 125% of the steady state $T_{max}$ of the MINOCIN® immediate-release minocycline hydrochloride.

For the single-dosage measurements, patients may be provided with a single dosage of a composition comprising the controlled-release minocycline, and plasma specimens may be collected from the patient at different time periods relative to the administration of the composition to determine pharmacokinetic profiles. For the steady-state measurements, patients may be provided with a dosing regimen across approximately 5 days comprising administering compositions comprising low-dosage controlled-release minocycline. Plasma specimens may then be collected from the patient at different time periods relative to a particular dosage during steady state. In some embodiments, the steady state can be determined by monitoring a plasma minocycline concentration profile at specific times of anticipated peak and trough blood levels relative to the administration of a dosage across hours and days and determining when the profile has reached steady state. For example, the in vivo plasma minocycline concentration may be measured one hour after dosing across days, until the concentration no longer significantly varies from day to day. In other embodiments, the steady state may be estimated as a specific number of days after the dosing regimen began. For example, steady state may be estimated as six days after the dosing regimen began. In some embodiments, steady state is estimated after dosing over about five times the half-life of the drug.

Plasma may be analyzed using any appropriate method. In some embodiments, blood is collected from a patient. Any suitable amount of blood may be collected. Blood samples may then be centrifuged until separation of red cells from plasma occurs. In some embodiments, minocycline analysis is performed using plasma specimens by the bioanalytical division of SFBC Anapharm using the analytical method of SOP ANI 8842.01 entitled "Determination of Minocycline in Human Lithium Heparinized Plasma Over a Concentration Range of 20 to 5000 ng/mL using a High Performance Liquid Chromatographic Method with Tandem Mass Spectrometry Detection and Using MultiPROBE II Automated Extraction," which is hereby incorporated by reference in its entirety. In some embodiments, minocycline analysis is performed according to the analytical method validation entitled "Validation of a High Performance Liquid Chromatographic Method Using Tandem Mass Spectrometry Lithium Heparinized Plasma," hereby incorporated by reference in its entirety. In some embodiments, samples are analyzed for the content of minocycline by HPLC/UV assay, as described in greater detail below.

One pharmacokinetic parameter, $C_{max}$, is the maximum observed plasma concentration. Another pharmacokinetic parameter, AUC, is the area under the plasma concentration versus time curve from the time of a specific dosage (which is the first and only dosage during single-dosage analysis and a specific later dosage during steady-state analysis, as described above) to the end of a specific interval. For example, the parameter may be the area under the plasma concentration versus time curve from the time a specific dosage to 24 hours following that dosage ($AUC_{(0-24)}$) or to 72 hours following that dosage ($AUC_{(0-72)}$). The AUC from the time of administration until an infinite time later ($AUC_{inf}$) may be extrapolated from the data by any appropriate method. Yet another pharmacokinetic parameter, $T_{max}$, is the time of occurrence of $C_{max}$ relative to the time of the specific dosage (which again is the first and only dosage during single-dosage analysis and the specific later dosage during steady-state analysis).

In order to measure the pharmacokinetic parameters mentioned above, in vivo minocycline concentrations may be measured at various time intervals with respect to a minocycline dosage. In some embodiments, these concentrations are measured at least 10 times within a 24 hour period. In some embodiments, the concentrations are measured pre-dose and at 0.5, 1.0, 1.5, 2.0, 3.0, 4.0, 5.0, 6.0, 8.0, 12.0, 12.5, 13.0, 13.5, 14.0, 15.0, 16.0, 17.0, 18.0 and 20.0 hours post-dose. In some embodiments, the concentrations are measured pre-dose and at 0.5, 1.0, 1.5, 2.0, 3.0, 4.0, 5.0, 6.0, 8.0, 10.0, 12.0, 24.0, 36.0, 48.0, and 72.0 hours post-dose.

In some embodiments, a patient population undergoes a dosing regimen comprising the administration of a composition comprising a dosage form as described herein, and the reported pharmacokinetic parameters are the average of the pharmacokinetic parameters across patients. The average may be obtained by calculating the parameters for each patient and then averaging across patients. In some embodiments, the averaging comprises a least-squares arithmetic mean or a least-squares geometric mean.

In some embodiments, pharmacokinetic parameters are obtained from crossover studies, wherein the composition comprises an extended-release formulation of minocycline hydrochloride and is compared to a comparable composition comprising an immediate-release formulation of 100 mg dosage of minocycline. In these embodiments, the reported pharmacokinetic parameters associated with administration of compositions comprising low-dosage extended-release minocycline may be averaged across both subject groups (such that the parameters associated with such compositions are averaged across all patients regardless of whether such compositions are received first or second).

In some embodiments, the pharmacokinetic profile of a composition described herein (e.g., controlled release minocycline oral dosage form) is pharmacokinetically distinct from an immediate-release composition. In some embodiments, the pharmacokinetic profile of a composition described herein is pharmacokinetically distinct from a comparable composition. The pharmacokinetic distinctness may be due to, for example, a difference in the $C_{max}$, $AUC_{(0-72)}$, and/or $T_{max}$ parameters. The parameters may be single-dosage or steady-state. The $C_{max}$ of a composition described herein may be less than about 80% of a comparable composition. The $AUC_{(0-72)}$ may be less than about 80% of a comparable composition. The $T_{max}$ may be greater than about 125% of a comparable composition. The comparable composition may differ by being of an immediate-release form, e.g., MINOCIN® immediate-release minocycline hydrochloride. The comparable composition may differ by comprising a higher dosage of a tetracycline-class antibiotic (e.g., minocycline). The comparable composition may be an immediate-release form including a higher dosage of the oral tetracycline-class antibiotic.

In some embodiments, a composition described herein (e.g., controlled release minocycline oral dosage form) provides a pharmacokinetic profile of one or more of a single-dosage $C_{max}$ that is about 80% or less of the single-dosage $C_{max}$ of the immediate-release dosage form; a steady-state $C_{max}$ that is about 80% or less of the steady-state $C_{max}$ of the immediate-release dosage form; a single-dosage $AUC_{(0-72)}$ that is about 80% or less of the single-dosage $AUC_{(0-72)}$ of the immediate-release dosage form; a steady state $AUC_{(0-72)}$ that is about 80% or less of the steady state $AUC_{(0-72)}$ of the immediate-release dosage form; a single-dosage $T_{max}$ that is at least about 125% of the single-dosage $T_{max}$ of the immediate-release dosage form; and a steady state $T_{max}$ that is at least about 125% of the steady state $T_{max}$ of the immediate-release dosage form. The composition may provide two or more of these pharmacokinetic profiles. The composition may provide all three of the steady-state pharmacokinetic profiles. The composition may provide all three of the single-dosage pharmacokinetic profiles.

In some embodiments, a composition described herein (e.g., controlled release minocycline oral dosage form) may provide specific pharmacokinetic profiles that are dose-adjusted to a 100-mg dosage. The dose-adjusted pharmacokinetic profile may include a single-dosage $C_{max}$ in the range of about 0.9 µg/mL to about 1.5 µg/mL or in the range of about 1.1 µg/mL to about 1.4 µg/mL. The dose-adjusted pharmacokinetic profile may include additionally or instead a single-dosage $AUC_{(0-72)}$ in the range of about 25 µg×hr/mL to about 30 µg×hr/mL or in the range of about 27 µg×hr/mL to about 29 µg×hr/mL. These values may indicate that the composition is pharmacokinetically distinct from a comparable composition. The dose-adjusted $C_{max}$ in the range of about 0.9 µg/mL to about 1.5 µg/mL or in the range of about 1.1 µg/mL to about 1.4 µg/mL may be about 80% or less of the single-dosage $C_{max}$ of the immediate-release dosage form, e.g., MINOCIN® immediate-release minocycline hydrochloride. The dose-adjusted $AUC_{(0-72)}$ in the range of about 25 µg×hr/mL to about 30 µg×hr/mL or in the range of about 27 µg×hr/mL to about 29 µg×hr/mL may be about 80% or less of the single-dosage $AUC_{(0-72)}$ of the immediate-release dosage form, e.g. MINOCIN® immediate-release minocycline hydrochloride. A composition described herein may provide a single-dosage $T_{max}$ in the range of about 3.2 to about 4.5 hours or in the range of about 3.5 to about 4.0 hours. These $T_{max}$ ranges may be about 125% or more of the single-dosage $T_{max}$ of the immediate-release dosage form, e.g. MINOCIN® immediate-release minocycline hydrochloride.

In some embodiments, a composition described herein (e.g., controlled release minocycline oral dosage form) may provide specific pharmacokinetic profiles that are dose-adjusted to a 100-mg dosage. The dose-adjusted pharmacokinetic profile may include a steady-state $C_{max}$ in the range of about 2.0 µg/mL to about 2.8 µg/mL or in the range of about 2.2 µg/mL to about 2.6 µg/mL. The dose-adjusted pharmacokinetic profile may include additionally or instead a steady-state $AUC_{(0-72)}$ in the range of about 25 µg×hr/mL to about 40 µg×hr/mL or in the range of about 28 µg×hr/mL to about 37 µg×hr/mL. These values may indicate that the composition is pharmacokinetically distinct from a comparable composition, e.g. MINOCIN® immediate-release minocycline hydrochloride. The dose-adjusted $C_{max}$ in the range of about 0.9 µg/mL to about 1.5 µg/mL or in the range of about 1.1 µg/mL to about 1.4 µg/mL may be about 80% or less of the steady-state $C_{max}$ of the immediate-release dosage form. The dose-adjusted $AUC_{(0-72)}$ in the range of about 25 µg×hr/mL to about 30 µg×hr/mL or in the range of about 27 µg×hr/mL to about 29 µg×hr/mL may be about 80% or less of the steady-state $AUC_{(0-72)}$ of the immediate-release dosage form e.g. MINOCIN® immediate-release minocycline hydrochloride. A composition described herein may provide a steady-state $T_{max}$ in the range of about 3.2 to about 4.5 hours or in the range of about 3.5 to about 4.0 hours. These $T_{max}$ ranges may be about 125% or more of the steady-state $T_{max}$ of the immediate-release dosage form e.g. MINOCIN® immediate-release minocycline hydrochloride.

An embodiment provides a minocycline oral dosage form, comprising minocycline or a pharmaceutically acceptable salt thereof and an amount of a controlled-release carrier composition that is effective to provide an in vitro release rate of the minocycline or pharmaceutically acceptable salt thereof of about 90% in about 4 hours to about 6 hours. In vitro release rate is determined by a standard dissolution test as described above. Thus, during this test, the point in time at which about 90% dissolution of the minocycline oral dosage form is achieved, is in the range of about 4 hours to about 6 hours after commencement of the test. Such an embodiment may be referred to herein as a 4-hour oral dosage formulation or simply as a 4-hour formulation. In an embodiment, the amount and type of controlled-release carrier composition that is effective to provide such a release rate is the same as that described elsewhere herein as being effective to render the oral dosage form pharmacokinetically distinct from MINOCIN® immediate-release minocycline hydrochloride. Thus, the methods of making and using controlled-release oral dosage forms described herein are applicable to 4-hour formulations. For example, in an embodiment, the 4-hour oral dosage formulation comprises a controlled-release carrier composition that comprises at least one selected from hydroxypropylmethylcellulose, hydroxypropylcellulose, and polyvinylpyrollidone. The amount of controlled-release carrier composition in the 4-hour formulation may be, for example, in the range of about 20% to about 30%, by weight based on the total weight of the minocycline oral dosage form. Likewise, various other descriptions provided herein such as minocycline form (e.g., minocycline hydrochloride), dosage (e.g., minocycline free base equivalent dosage in the range of about 0.75 mg/kg to about 1.5 mg/kg), unit dosage size (e.g., about 45 mg, about 60 mg, about 90 mg and about 135 mg), methods of treatment, methods of distribution, methods of making, methods of reducing adverse effects, kits, etc., are not limited to the context in which they may be discussed, but are equally applicable to 4-hour formulations.

Administration of a composition as described herein (e.g., a controlled-release minocycline oral dosage form) may result in an in vivo plasma minocycline $C_{max}$ as described herein. Administration of the composition may result in an in vivo plasma minocycline AUC as described herein. Administration of the composition may result in an in vivo plasma minocycline $T_{max}$ as described herein. Administration of the composition may result in two selected from the in vivo plasma minocycline $C_{max}$ as described herein, the in vivo plasma minocycline AUC as described herein, and the in vivo plasma minocycline $T_{max}$ as described herein. Administration of the composition may result in an in vivo plasma minocycline $C_{max}$ described herein, an in vivo plasma minocycline AUC as described herein and an in vivo plasma minocycline $T_{max}$ as described herein.

A pharmacokinetic profile described herein may be associated with reduced adverse side effects following administration of a composition described herein as compared to those expected and/or obtained by administration of a comparable composition (e.g., MINOCIN® immediate-release minocycline hydrochloride), as described in greater detail below. This invention is not bound by theory of operation, but it is believed that the some or all of the adverse effects associated with immediate-release dosage forms may result from dosage practices that produce concentration profiles of the drug in plasma that were believed to be needed to provide efficacy. However, the administration of the oral dosage forms in accordance with some embodiments described herein produces concentration profiles of the drug that are pharmacokinetically distinct from those obtained by administration of a comparable composition, yet still provide substantially similar or better treatment efficacy and/or reduced incidence of at least one adverse effect.

In some embodiments, a controlled-release tetracycline-class antibiotic oral dosage form as described herein can be distributed, provided to a patent for self-administration or administered to a patient. The patient is typically suffering from or at risk of suffering from acne or a complication thereof. In some embodiments, the acne is acne vulgaris. In other embodiments, the acne is acne rosacea. In still other embodiments, the acne may be one or more of acne conglobata, acne fulminans, gram-negative folliculitis, and pyoderma faciale. The acne may be a severe form of acne, a moderate form of acne, or a mild form of acne. Such distribution, provision or administration of a controlled-release tetracycline-class antibiotic oral dosage form as described herein may be in conjunction with the provision of information regarding actual or potential adverse side effects and/or reductions in adverse effects that may be obtained by administration of a controlled-release tetracycline-class antibiotic oral dosage form as described herein.

Currently marketed immediate-release minocycline products have been approved as adjunctive therapy in cases of severe acne, but were not formally studied in FDA trials for that indication, see Leyden, J. Cutis 2006; 78 (suppl 4):4-5. The recommended daily dose of immediate-release minocycline for the treatment of acne ranges from about 2 mg/kg/day to about 4 mg/kg/day. Previous studies have suggested that high dosages are necessary for effective treatment of acne, Pierard-Franchimont et al., Skin Pharmacol. Appl. Skin Physiol. 15(2): 112-119 (2002). However, as noted above, a commercial embodiment of the extended-release minocycline oral dosage forms described herein is reported to be the first systemic antibiotic approved by the FDA for the treatment of acne, see Leyden, J. Cutis 2006; 78 (suppl 4):4-5.

In an embodiment, oral dosage forms described herein are effective in the treatment of acne. In some embodiments, the oral dosage form is more effective than a comparable composition (e.g., MINOCIN® immediate-release minocycline hydrochloride). The comparable composition may comprise higher dosages of the active ingredient and/or an immediate-release formulation. The comparable composition may provide a release rate of greater than 50%, 90% or 95% in about 1, about 2, about 4, or about 6 hours. The comparable composition may provide a release rate of 50%, 90% or 95% in less than about 1, about 2, about 4, or about 6 hours.

It will be understood that the specific dose level of the controlled-release oral dosage forms described herein for any particular patient can depend upon any of a variety of factors including the genetic makeup, body weight, general health, diet, time and route of administration, combination with other drugs and the particular condition being treated, and its severity. In an embodiment, low dosages of the active ingredient are provided. These low doses are effective and, in most patients, are associated with reduced side effects as compared to higher dosages. Dosages described herein may involve comparatively low dosages of a tetracycline, minocycline, and/or minocycline hydrochloride.

In some embodiments, the controlled-release oral dosage forms described herein remain effective in treating acne despite providing a lower AUC as compared to that provided by higher dosages of an immediate-release dosage form such as MINOCIN® immediate-release minocycline hydrochloride. In some embodiments, the controlled-release oral dosage forms described herein provide substantially similar or improved acne treatment efficacy as compared to an otherwise comparable composition containing a larger dosage of the active ingredient. In some embodiments, once-daily administration of a composition described herein provides substantially similar or better acne treatment efficacy as compared to a twice-daily administration of the immediate-release dosage form. In some embodiments, treatment dosages are based on the body weight of the patient, e.g., for minocycline dosages may be in the range of about 0.75 mg/kg to about 1.5 mg/kg, e.g., about 1 milligram of minocycline (free base equivalent) per kilogram of patient body weight. Once-daily dosing is provided in some embodiments.

In an embodiment, administration of a controlled-release minocycline oral dosage form as described herein on a once-daily basis is effective. As noted above, the dosing schedule used most frequently for treating acne using currently available immediate-release oral dosage forms is 100 mg of minocycline (free base equivalent) administered twice daily, see Leyden, J. Cutis 2006; 78 (suppl 4):4-5. In an embodiment, a controlled-release minocycline oral dosage form as described herein has a single-dosage $T_{max}$ that is about 125% or more of the single-dosage $T_{max}$ of MINOCIN® immediate-release minocycline hydrochloride, e.g., a $T_{max}$ that occurs about an hour later. Such a difference in $T_{max}$ is considerably less than 12 hours and thus once-daily administration of such a controlled-release minocycline oral dosage form would not ordinarily be expected to provide comparable efficacy to twice-daily administration of the immediate-release oral dosage form. However, in an embodiment, once-daily dosing of a controlled-release minocycline oral dosage form as described herein, e.g., at a dosage in the range of about 0.75 mg/kg to about 1.5 mg/kg, provides substantially similar or better acne treatment efficacy, as compared to a twice-daily administration of a conventional immediate release form, e.g., MINOCIN® immediate-release minocycline hydrochloride. In an embodiment, such once-daily dosing further provides a reduced incidence of at least one adverse effect as compared to a twice-daily administration of a conventional immediate release form, e.g., MINOCIN® immediate-release minocycline hydrochloride.

In some embodiments, a patient is provided with a composition comprising minocycline hydrochloride, wherein the dosage of minocycline hydrochloride is 45 mg, 60 mg, 90 mg or 135 mg, and the dosage is determined by the weight of the patient. In some these embodiments, the dosage is chosen such that the administered or provided dosage of minocycline hydrochloride is in the range of about 0.75 mg/kg to about 1.5 mg/kg.

In some embodiments, the dosage is held constant across days. In other embodiments, the dosage may vary across days. For example, the initial dosages of minocycline may be higher than subsequent dosages. The dosages may be predetermined or may be determined based on the patient's reaction to the dosage. For example, the dosage may be decreased until the dose is no longer effective. In other embodiments, the dosage can be increased until the severity of at least one adverse side effect increases. For example, the dosage may be increased until the patient reports experiencing a vestibular side effect.

Effective treatment of acne may be characterized in various ways. For example, effective treatment of acne may be characterized as a reduction, and in some embodiments a substantial reduction, in the number of acne lesions. The acne lesions may be defined as at least one of inflammatory and non-inflammatory lesions. Effective treatment of acne may be characterized as a reduction in the severity of acne. Effective treatment of acne may be characterized as a reduction in the duration of an outbreak. For example, a composition described herein may reduce the duration that a lesion will remain after it has formed. Effective treatment of acne may be characterized as a reduced probability of an acne-related symptom. For example, a composition described herein may reduce the probability of developing further lesions.

In some embodiments, oral dosage forms and methods described herein can be used to treat acne, wherein the acne is acne vulgaris. In other embodiments, the acne is acne rosacea. In still other embodiments, the acne may be one or more of acne conglobata, acne fulminans, gram-negative folliculitis, and pyoderma faciale. The acne may be a severe form of acne, a moderate form of acne, or a mild form of acne, and may include inflammatory and/or non-inflammatory lesions. In an embodiment, oral dosage forms and methods described herein can be used to treat inflammatory lesions of acne vulgaris.

In some embodiments, the acne is at least partially caused by hormonal changes, excessive production of one or more male hormones, or pregnancy. The acne may be caused by a medication, such as a contraceptive pill, ointments for eczema, or medicine for epilepsy. The acne may be caused by a drug, such as androgens, lithium, or barbiturates.

Administration of a controlled-release tetracycline-class antibiotic oral dosage form as described herein (e.g., extended-release minocycline) may result in the reduction of one or more adverse side effects associated with administration of a comparable composition (e.g., MINOCIN® immediate-release minocycline hydrochloride) as described in further detail below. The one or more adverse side effects may comprise a side effect associated with acne treatment using the comparable composition. In general, the comparable composition may comprise higher dosages of the active ingredient and/or an immediate-release formulation. The comparable composition may provide a release rate of greater than 50%, 90% or 95% in about 1, about 2, about 4, or about 6 hours. The comparable composition may provide a release rate of 50%, 90% or 95% in less than about 1, about 2, about 4, or about 6 hours. In some embodiments, a composition described herein reduces one or more adverse side effects while maintaining efficacy, as described above.

In some embodiments, administration of a controlled-release tetracycline-class antibiotic oral dosage form as described herein may reduce the probability of the adverse side effect occurring. In other embodiments, such administration may reduce the magnitude of at least one adverse side effect. In other embodiments, such administration may reduce the duration of at least one adverse side effect. In some cases, e.g., involving individual patients, such reductions may be in comparison to the side effects that would be expected by one of skill in the art in view of the known side effects of a higher-dosage immediate release form, and thus it is not necessary that the patient actually experience side effects from the immediate release form in order to benefit from such reductions in side effects.

Examples of adverse side effects that may be reduced by administration in accordance with certain embodiments include one or more of: ear and labyrinth disorders, eye disorders, gastrointestinal disorders, immune system disorders, infections and infestations, laboratory blood abnormalities, metabolism and nutritional disorders, musculoskeletal and connective disorders, nervous system disorders, psychiatric disorders, renal and urinary disorders, reproductive system and breast disorders, respiratory, thoracic and mediastinal disorders, skin and subcutaneous tissue disorders, vascular disorders, pseudomembranous colitis, hepatotoxicity, vasculitis, tissue hyperpigmentation, and/or anaphylaxis.

An adverse side effect may include one or more gastrointestinal disorders, blurred vision, autoimmune syndromes, and/or adverse renal reactions. The gastrointestinal disorder may include anorexia, nausea, vomiting, diarrhea, glossitis, dysphagia, enterocolitis, pancreatitis, inflammatory lesions (with monilial overgrowth) in the anogenital region, increases in liver enzymes, hepatitis, liver failure, esophagitis and/or esophageal ulcerations. The skin and subcutaneous tissue disorder may include maculopapular, erythematous rashes, exfoliative dermatitis, fixed drug eruptions, balanitis, erythema multiforme, Stevens-Johnson syndrome, or pigmentation of the skin and/or mucous membranes. The adverse renal reaction may be an elevation in BUN and/or acute renal failure. The metabolism and nutritional disorder may be azotemia, hyperphosphatemia, and/or acidosis. An adverse side effect may be a hypersensitivity reaction side effect. The hypersensitivity reaction side effect may be urticaria, angioneurotic edema, polyarthralgia, anaphylaxis, anaphylactoid purpura, pericarditis, exacerbation of systemic lupus erythematosus, pulmonary infiltrates with eosinophilia, and/or transient lupus-like syndrome. An adverse side effect may be a blood side effect. The blood side effect may be hemolytic anemia, thrombocytopenia, neutropenia, and/or eosinophilia. An adverse side may be a central nervous system side effect. The central nervous system side effect may be light-headedness, dizziness, vertigo, pseudotumor cerebri or benign intracranial hypertension. An adverse side effect may be a brown-black microscopic discoloration of the thyroid glands, soft tissue, bone or teeth, abnormal thyroid function, and/or hepatotoxicity.

In some embodiments, a controlled-release tetracycline-class antibiotic oral dosage form as described herein can be administered in conjunction with other acne treatments or medications. For example, an extended-release minocycline oral dosage form may include one or more other acne medications, such as an antibiotic and/or retinoid, e.g., retinol, retinoic acid, another oral tetracycline, dapsone, prednisone, and/or estrogen, or they may be administered separately. In some embodiments, a controlled-release tetracycline-class antibiotic oral dosage form as described herein can be administered in conjunction with the use of a topical acne treatment product such as a topical antibiotic, a topical retinoid, and/or a cream or facial cleanser product, e.g., a cleanser that contains benzoyl peroxide such as TRIAZ® cleanser pads (available commercially from Medicis Pharmaceutical Corporation, Phoenix, Ariz.).

In some embodiments, methods of the present invention include identifying a patient suffering from at least one adverse side effect and/or who is particularly susceptible to at least one adverse side effect associated with a comparable higher-dosage immediate-release composition (such as MINOCIN® immediate-release minocycline hydrochloride) and providing or administering to the patient a controlled-release tetracycline-class antibiotic oral dosage form as described herein. In other embodiments, methods of the present invention include identifying a patient who is particularly susceptible to at least one adverse side effect.

Methods of use can include the step of administering a therapeutically-effective amount of the oral dosage form to a mammal in need thereof by any suitable route or method of delivery, including those described herein. Actual dosage levels of the compounds in the pharmaceutical compositions may be varied so as to administer an amount of the tetracycline-class antibiotic (e.g., minocycline) that is effective to achieve the desired therapeutic response for a particular patient. Examples of dosages that can be used are described more fully elsewhere herein. Suitable routes of administration include delivery in the form of, e.g., pills, tablets, powders, granules, dragees, capsules, liquids, sprays, gels, syrups, slurries, suspensions and the like, any of which can be in unit dosage form, for oral ingestion by a patient to be treated. The formulation can be in form suitable for bolus administration, for example. Oral administration can be accomplished using fast-melt formulations, for example. As a further example, the formulations can be included in push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Formulations for oral administration can be in unit dosages suitable for such administration.

In some embodiments, a composition described herein may be associated with one or more adverse side effects. The one or more side effects may include pseudomembranous colitis, hepatotoxicity, vasculitis, tissue hyperpigmentation, and anaphylaxis.

In some embodiments, a composition described herein is administered to a patient. The patient may be informed that the composition may cause one or more adverse side effects. The patient may be informed that the composition may cause one or more of pseudomembranous colitis, hepatotoxicity, vasculitis, tissue hyperpigmentation, and anaphylaxis. The patient may be provided information that the composition may cause one or more adverse side effects. The patient may be provided information that the composition may cause one or more of pseudomembranous colitis, hepatotoxicity, vasculitis, tissue hyperpigmentation, and anaphylaxis.

In some embodiments, a composition described herein is distributed. Information may also be distributed, and may be concomitantly distributed with the composition, indicating that the composition may cause one or more adverse side effects.

Information may also be distributed, and may be concomitantly distributed with the composition, indicating that the composition may cause one or more of pseudomembranous colitis, hepatotoxicity, vasculitis, tissue hyperpigmentation, and anaphylaxis.

In some embodiments, the present invention relates to a kit. The kit may include one or more unit dosage forms comprising a tetracycline-class antibiotic. The tetracycline-class antibiotic may be minocycline. The tetracycline-class antibiotic may be present in a low dosage. The unit dosage form may be of a controlled-release formulation. The unit dosage forms may be of an oral formulation. The unit dosage forms may comprise tablets. The kit may include a plurality of unit dosage forms.

The kit may include information. The information may be directed towards a physician, pharmacist or patient. The information may indicate that the unit dosage form may cause one or more adverse effects. The information may indicate that the unit dosage form is to be administered once per day. The information may indicate that the unit dosage form may cause one or more adverse side effects. The information may indicate that the unit dosage form may cause one or more of pseudomembranous colitis, hepatotoxicity, vasculitis, tissue hyperpigmentation, and anaphylaxis.

The information may comprise instructions to administer the unit dosage form at a dosage of about 0.75 mg/kg to about 1.5 mg/kg. These instructions may be provided in a variety of ways. For example, the information may include a table including a variety of weights or weight ranges and appropriate dosages for each weight or weight range.

The information may be provided on a readable medium. The readable medium may comprise a label. The kit may comprise a therapeutic package suitable for commercial sale. The kit may comprise a container. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual dosages for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

The information can be associated with the container, for example, by being: written on a label (e.g., the prescription label or a separate label) adhesively affixed to a bottle containing a composition described herein; included inside a container as a written package insert, such as inside a box which contains unit dose packets; applied directly to the container such as being printed on the wall of a box; or attached as by being tied or taped, for example as an instructional card affixed to the neck of a bottle via a string, cord or other line, lanyard or tether type device. The information may be printed directly on a unit dose pack or blister pack or blister card.

In an embodiment, one or more of the oral dosage forms, methods and/or kits described herein is provided, with a proviso that the oral dosage form, method and/or kit does not include a composition, oral dosage form or method disclosed in U.S. Patent Publication No. 2006-0293290, published 28 Dec. 2006, which is hereby incorporated by reference in its entirety. For example, an embodiment provides an oral dosage form as described herein, with the proviso that the oral dosage form does not include a 135 mg caplet that consists of 145.8 mg minocycline hydrochloride, 107.4 mg lactose monohydrate (intragranular), 43.8 mg lactose monohydrate (extragranular), 94 mg HPMC, 3 mg silicon dioxide and 6 mg magnesium stearate. As another example, an embodiment provides a method of administering an oral dosage form as described herein, wherein the method does not include administering such a 135 mg caplet. As another example, an embodiment provides an oral dosage form as described herein, wherein the oral dosage form does not include a 45 mg caplet that consists of 48.6 mg minocycline hydrochloride, 192.2 mg lactose monohydrate (intragranular), 42.2 mg lactose monohydrate (extragranular), 108 mg HPMC, 3 mg silicon dioxide and 6 mg magnesium stearate. As another example, an embodiment provides a method of administering an oral dosage form as described herein, wherein the method does not include administering such a 45 mg caplet.

Non-limiting embodiments of the invention include the following:

Embodiment 1

An oral dosage form, comprising: minocycline or a pharmaceutically acceptable salt thereof; and an amount of a controlled-release carrier composition that is effective to render said oral dosage form pharmacokinetically distinct from MINOCIN® immediate-release minocycline hydrochloride.

Embodiment 2

The oral dosage form of Embodiment 1, wherein a once-daily administration of said oral dosage form provides substantially similar or better acne treatment efficacy and reduced incidence of at least one adverse effect, as compared to a twice-daily administration of said MINOCIN® immediate-release minocycline hydrochloride.

Embodiment 3

The oral dosage form of Embodiment 1 or 2, wherein said oral dosage form provides, after administration, at least one in vivo plasma minocycline concentration profile selected from:
(a) a single-dosage $C_{max}$ that is about 80% or less of the single-dosage $C_{max}$ of the MINOCIN® immediate-release minocycline hydrochloride;
(b) a steady-state $C_{max}$ that is about 80% or less of the steady-state $C_{max}$ of the MINOCIN® immediate-release minocycline hydrochloride;
(c) a single-dosage $AUC_{(0-72)}$ that is about 80% or less of the single-dosage $AUC_{(0-72)}$ of the MINOCIN® immediate-release minocycline hydrochloride;
(d) a steady state $AUC_{(0-72)}$ that is about 80% or less of the steady state $AUC_{(0-72)}$ of the MINOCIN® immediate-release minocycline hydrochloride;
(e) a single-dosage $T_{max}$ that is at least about 125% of the single-dosage $T_{max}$ of the MINOCIN® immediate-release minocycline hydrochloride; and
(f) a steady state $T_{max}$ that is at least about 125% of the steady state $T_{max}$ of the MINOCIN® immediate-release minocycline hydrochloride.

Embodiment 4

The oral dosage form of Embodiment 3, wherein said in vivo plasma minocycline concentration profile is dose-adjusted to a 100 mg dosage and wherein:
said single-dosage $C_{max}$ is in the range of about 0.9 µg/mL to about 1.5 µg/mL;
said single-dosage $AUC_{(0-72)}$ is in the range of about 25 µg×hr/mL to about 30 µg×hr/mL; or
said single-dosage $C_{max}$ in the range of about 0.9 µg/mL to about 1.5 µg/mL and said single-dosage $AUC_{(0-72)}$ is in the range of about 25 µg×hr/mL to about 30 µg×hr/mL.

Embodiment 5

The oral dosage form of any one of Embodiments 3 to 4, wherein said single-dosage $T_{max}$ in the range of about 3.2 to about 4.5 hours.

Embodiment 6

The oral dosage form of Embodiment 5, wherein said single-dosage $T_{max}$ is in the range of about 3.5 to about 4.0 hours.

Embodiment 7

The oral dosage form of Embodiment 4, wherein said single-dosage $C_{max}$ is in the range of about 1.1 µg/mL to about 1.4 µg/mL.

Embodiment 8

The oral dosage form of Embodiment 4, wherein said single-dosage $AUC_{(0-72)}$ is in the range of about 27 µg×hr/mL to about 29 µg×hr/mL.

Embodiment 9

The oral dosage form of Embodiment 3, wherein said in vivo plasma minocycline concentration profile is dose-adjusted to a 100 mg dosage and wherein:
said steady-state $C_{max}$ is in the range of about 2.0 µg/mL to about 2.8 µg/mL;
said steady-state $AUC_{(0-24)}$ is in the range of about 25 µg×hr/mL to about 40 µg×hr/mL; or
said steady-state $C_{max}$ is in the range of about 2.0 µg/mL to about 2.8 µg/mL and said steady-state $AUC_{(0-24)}$ is in the range of about 25 µg×hr/mL to about 40 µg×hr/mL.

Embodiment 10

The oral dosage form of Embodiment 3 or Embodiment 9, wherein said steady-state $T_{max}$ in the range of about 3.2 to about 4.5 hours.

Embodiment 11

The oral dosage form of Embodiment 10, wherein said steady-state $T_{max}$ is in the range of about 3.5 to about 4.0 hours.

Embodiment 12

The oral dosage form of Embodiment 9, wherein said steady-state $C_{max}$ is in the range of about 2.2 µg/mL to about 2.6 µg/mL.

Embodiment 13

The oral dosage form of Embodiment 9, wherein said steady-state $AUC_{(0-72)}$ is in the range of about 28 µg×hr/mL to about 37 µg×hr/mL.

Embodiment 14

The oral dosage form of any one of Embodiments 1 to 13, wherein said minocycline salt is minocycline hydrochloride.

Embodiment 15

The oral dosage form of any one of Embodiments 1 to 14, wherein said oral dosage form is in a unit dosage form suitable for administration to a human at a minocycline free base equivalent dosage in the range of about 0.75 mg/kg to about 1.5 mg/kg.

Embodiment 16

The oral dosage form of Embodiment 15, wherein said unit dosage form comprises minocycline hydrochloride in a minocycline free base equivalent amount selected from about 45 mg, about 60 mg, about 90 mg and about 135 mg.

Embodiment 17

The oral dosage form of any one of Embodiments 3 to 16, wherein said in vivo plasma minocycline concentration profile is single-dosage $C_{max}$.

Embodiment 18

The oral dosage form of any one of Embodiments 3 to 16, wherein said in vivo plasma minocycline concentration profile is single-dosage $AUC_{(0-72)}$.

Embodiment 19

The oral dosage form of any one of Embodiments 3 to 16, wherein said in vivo plasma minocycline concentration profile is single-dosage $T_{max}$.

Embodiment 20

The oral dosage form of any one of Embodiments 3 to 16, wherein said in vivo plasma minocycline concentration profile is steady-state $C_{max}$.

Embodiment 21

The oral dosage form of any one of Embodiments 3 to 16, wherein said in vivo plasma minocycline concentration profile is steady-state $AUC_{(0-72)}$.

Embodiment 22

The oral dosage form of any one of Embodiments 3 to 16, wherein said in vivo plasma minocycline concentration profile is steady-state $T_{max}$ Embodiment 23

The oral dosage form of any one of Embodiments 3 to 16, wherein said oral dosage form provides, after administration, at least two of said in vivo plasma minocycline concentration profiles.

Embodiment 24

The oral dosage form of any one of Embodiments 3 to 16, wherein said oral dosage form provides said single-dosage $C_{max}$, said single-dosage $AUC_{(0-72)}$ and said single-dosage $T_{max}$.

Embodiment 25

The oral dosage form of any one of Embodiments 3 to 16, wherein said oral dosage form provides said steady-state $C_{max}$, said steady-state $AUC_{(0-72)}$ and said steady-state $T_{max}$.

Embodiment 26

The oral dosage form of any one of Embodiments 1 to 25, wherein said controlled-release carrier composition comprises at least one selected from hydroxypropylmethylcellulose, hydroxypropylcellulose, and polyvinylpyrollidone.

Embodiment 27

A method of treating acne, comprising administering the oral dosage form of any one of Embodiments 1 to 26 to a subject in need thereof.

Embodiment 28

The method of Embodiment 27, comprising administering the oral dosage form to the subject at a minocycline free base equivalent dosage in the range of about 0.75 mg/kg to about 1.5 mg/kg.

Embodiment 29

The method of Embodiment 27 or Embodiment 28, comprising administering the oral dosage form to the subject on a once-daily basis.

Embodiment 30

The method of any one of Embodiments 27 to 29, further comprising reducing at least one adverse side effect as compared to that expected from administering the MINOCIN® immediate-release minocycline hydrochloride.

Embodiment 31

The method of Embodiment 30, wherein reducing at least one adverse side effect comprises reducing the likelihood of experiencing said adverse side effect.

Embodiment 32

The method of Embodiment 30, wherein reducing at least one adverse side effect comprises reducing the magnitude of said adverse side effect.

Embodiment 33

The method of Embodiment 30, wherein reducing at least one adverse side effect comprises reducing the duration of said adverse side effect.

Embodiment 34

The method of any one of Embodiments 27 to 33, further comprising informing the subject that the oral dosage form may cause an adverse effect.

Embodiment 35

The method of Embodiment 34, wherein the adverse effect is selected from ear and labyrinth disorders, eye disorders, gastrointestinal disorders, immune system disorders, infections and infestations, laboratory blood abnormalities, metabolism and nutritional disorders, musculoskeletal and connective disorders, nervous system disorders, psychiatric disorders, renal and urinary disorders, reproductive system and breast disorders, respiratory, thoracic and mediastinal disorders, skin and subcutaneous tissue disorders, vascular disorders, pseudomembranous colitis, hepatotoxicity, vasculitis, tissue hyperpigmentation, and anaphylaxis.

Embodiment 36

The method of Embodiment 34, wherein the adverse effect is selected from gastrointestinal disorders, blurred vision, autoimmune syndromes, and adverse renal reactions.

Embodiment 37

A method of distributing minocycline, comprising:
distributing the oral dosage form of any one of Embodiments 1 to 26; and
concomitantly distributing information that the oral dosage form may cause an adverse effect.

Embodiment 38

The method of Embodiment 37, wherein the adverse effect is selected from ear and labyrinth disorders, eye disorders, gastrointestinal disorders, immune system disorders, infections and infestations, laboratory blood abnormalities, metabolism and nutritional disorders, musculoskeletal and connective disorders, nervous system disorders, psychiatric disorders, renal and urinary disorders, reproductive system and breast disorders, respiratory, thoracic and mediastinal disorders, skin and subcutaneous tissue disorders, vascular disorders, pseudomembranous colitis, hepatotoxicity, vasculitis, tissue hyperpigmentation, and anaphylaxis.

Embodiment 39

The method of Embodiment 37, wherein the adverse effect is selected from gastrointestinal disorders, blurred vision, autoimmune syndromes, and adverse renal reactions.

Embodiment 40

A method of making the oral dosage form of any one of Embodiments 1 to 26, comprising intermixing the minocycline or pharmaceutically acceptable salt thereof and the controlled-release carrier composition to form an admixture.

Embodiment 41

The method of Embodiment 40, further comprising forming the admixture into a unit dosage form.

Embodiment 42

The method of Embodiment 41, wherein forming the admixture into the unit dosage form comprises compressing the admixture into tablets.

Embodiment 43

A method of administering an oral dosage form comprising:
(i) administering to a patient an oral dosage form, which oral dosage form comprises:
an oral tetracycline-class antibiotic;
a fast dissolving carrier; and
a slow dissolving carrier; and
(ii) providing information to the patient, wherein the information comprises that the administering of the oral dosage form may cause one or more adverse effects selected from pseudomembranous colitis, hepatotoxicity, vasculitis, tissue hyperpigmentation, and anaphylaxis.

Embodiment 44

The method of Embodiment 43, wherein the fast dissolving carrier and the slow dissolving carrier are at a weight ratio of from 0.3 to 0.5 of fast dissolving carrier to slow dissolving carrier.

Embodiment 45

The method of Embodiment 43, wherein the fast dissolving carrier and the slow dissolving carrier are at a weight ratio of from 0.3 to 0.45 of fast dissolving carrier to slow dissolving carrier.

Embodiment 46

The method of Embodiment 43, wherein the fast dissolving carrier and the slow dissolving carrier are at a weight ratio of from about 0.36 to 0.40 of fast dissolving carrier to slow dissolving carrier.

Embodiment 47

The method of any one of Embodiments 43 to 46, wherein the adverse effect is pseudomembranous colitis.

Embodiment 48

The method of any one of Embodiments 43 to 46, wherein the adverse effect is hepatotoxicity.

Embodiment 49

The method of any one of Embodiments 43 to 46, wherein the adverse effect is vasculitis.

Embodiment 50

The method of any one of Embodiments 43 to 46, wherein the adverse effect is tissue hyperpigmentation.

Embodiment 51

The method of any one of Embodiments 43 to 46, wherein the adverse effect is anaphylaxis.

Embodiment 52

The method of any one of Embodiments 43 to 51, wherein the patient has been diagnosed with acne vulgaris.

Embodiment 53

A method of distributing an oral dosage form, comprising:
distributing an oral dosage form comprising an oral tetracycline-class antibiotic, a fast dissolving carrier and a slow dissolving carrier; and
concomitantly distributing information that the oral dosage form may cause one or more adverse effects selected from pseudomembranous colitis, hepatotoxicity, vasculitis, tissue hyperpigmentation, and anaphylaxis.

Embodiment 54

The method of Embodiment 53, wherein the fast dissolving carrier and the slow dissolving carrier are at a weight ratio of from 0.3 to 0.5 of fast dissolving carrier to slow dissolving carrier.

Embodiment 55

The method of Embodiment 53, wherein the fast dissolving carrier and the slow dissolving carrier are at a weight ratio of from 0.35 to 0.45 of fast dissolving carrier to slow dissolving carrier.

Embodiment 56

The method of Embodiment 53, wherein the fast dissolving carrier and the slow dissolving carrier are at a weight ratio of from about 0.36 to 0.40 of fast dissolving carrier to slow dissolving carrier.

Embodiment 57

The method of any one of Embodiments 53 to 56, wherein the adverse effect is pseudomembranous colitis.

Embodiment 58

The method of any one of Embodiments 53 to 56, wherein the adverse effect is hepatotoxicity.

Embodiment 59

The method of any one of Embodiments 53 to 56, wherein the adverse effect is vasculitis.

Embodiment 60

The method of any one of Embodiments 53 to 56, wherein the adverse effect is tissue hyperpigmentation.

Embodiment 61

The method of any one of Embodiments 53 to 56, wherein the adverse effect is anaphylaxis.

Embodiment 62

A method of administering an oral dosage form comprising:
(i) administering to a patient an oral dosage form, which oral dosage form comprises:
an oral tetracycline-class antibiotic;
a fast dissolving carrier; and
a slow dissolving carrier;
wherein the fast dissolving carrier and the slow dissolving carrier are at a weight ratio of 0.3 to 0.5 of fast dissolving carrier to slow dissolving carrier; and
(ii) providing information to the patient, which information comprises that the administering of the oral dosage form may cause one or more adverse effects.

Embodiment 63

The method of Embodiment 62, wherein the weight ratio of fast dissolving carrier to slow dissolving carrier is 0.35 to 0.45.

Embodiment 64

The method of Embodiment 62, wherein the weight ratio of fast dissolving carrier to slow dissolving carrier is about 0.36 to 0.40.

Embodiment 65

The method of any one of Embodiments 62 to 64, wherein the one or more adverse effects is/are selected from ear and labyrinth disorders, eye disorders, gastrointestinal disorders, immune system disorders, infections and infestations, laboratory blood abnormalities, metabolism and nutritional disorders, musculoskeletal and connective disorders, nervous system disorders, psychiatric disorders, renal and urinary disorders, reproductive system and breast disorders, respiratory, thoracic and mediastinal disorders, skin and subcutaneous tissue disorders, and vascular disorders.

Embodiment 66

The method of any one of Embodiments 62 to 64, wherein the one or more adverse effects is/are selected from gastrointestinal disorders, blurred vision, autoimmune syndromes, and adverse renal reactions.

Embodiment 67

The method of any one of Embodiments 62 to 66, wherein the patient has been diagnosed with acne vulgaris.

Embodiment 68

A method of distributing an oral dosage form, comprising:
distributing an oral dosage form comprising an oral tetracycline-class antibiotic, a fast dissolving carrier and a slow dissolving carrier, wherein the fast dissolving carrier and the slow dissolving carrier are at a weight ratio of 0.3 to 0.5 of fast dissolving carrier to slow dissolving carrier; and
concomitantly distributing information that the oral dosage form may cause one or more adverse effects.

Embodiment 69

The method of Embodiment 68, wherein the fast dissolving carrier and the slow dissolving carrier are at a weight ratio of 0.35 to 0.45 of fast dissolving carrier to slow dissolving carrier.

Embodiment 70

The method of Embodiment 68, wherein the fast dissolving carrier and the slow dissolving carrier are at a weight ratio of about 0.36 to 0.40 of fast dissolving carrier to slow dissolving carrier.

Embodiment 71

The method of any one of Embodiments 68 to 70, wherein the one or more adverse effects is/are selected from ear and labyrinth disorders, eye disorders, gastrointestinal disorders, immune system disorders, infections and infestations, laboratory blood abnormalities, metabolism and nutritional disorders, musculoskeletal and connective disorders, nervous system disorders, psychiatric disorders, renal and urinary disorders, reproductive system and breast disorders, respiratory, thoracic and mediastinal disorders, skin and subcutaneous tissue disorders, and vascular disorders.

Embodiment 72

The method of any one of Embodiments 68 to 70, wherein the one or more adverse effects is/are selected from gastrointestinal disorders, blurred vision, autoimmune syndromes, and adverse renal reactions.

Embodiment 73

A minocycline oral dosage form, comprising minocycline or a pharmaceutically acceptable salt thereof and an amount of a controlled-release carrier composition that is effective to provide an in vitro release rate of the minocycline or pharmaceutically acceptable salt thereof of about 90% in about 4 hours to about 6 hours.

Embodiment 74

The minocycline oral dosage form of Embodiment 73, wherein said controlled-release carrier composition comprises at least one selected from hydroxypropylmethylcellulose, hydroxypropylcellulose, and polyvinylpyrrolidone.

Embodiment 75

The minocycline oral dosage form of Embodiment 73 or Embodiment 74, wherein said amount of said controlled-release carrier composition is in the range of about 20% to about 30%, by weight based on the total weight of the minocycline oral dosage form.

Embodiment 76

The minocycline oral dosage form of any one of Embodiments 73 to 75, wherein the minocycline salt comprises minocycline hydrochloride.

Embodiment 77

The minocycline oral dosage form of any one of Embodiments 73 to 76, wherein said oral dosage form is in a unit dosage form suitable for administration to a human at a minocycline free base equivalent dosage in the range of about 0.75 mg/kg to about 1.5 mg/kg.

Embodiment 78

The minocycline oral dosage form of Embodiment 77, wherein said unit dosage form comprises minocycline hydrochloride in a minocycline free base equivalent amount selected from about 45 mg, about 60 mg, about 90 mg and about 135 mg.

Embodiment 79

The minocycline oral dosage form of Embodiment 78, wherein said unit dosage form comprises minocycline hydrochloride in a minocycline free base equivalent amount of about 45 mg and about 26% to about 28% of said controlled-release carrier composition, by weight based on the total weight of the minocycline oral dosage form.

Embodiment 80

The minocycline oral dosage form of Embodiment 78, wherein said unit dosage form comprises minocycline hydrochloride in a minocycline free base equivalent amount of about 90 mg and about 26% to about 28% of said controlled-release carrier, by weight based on the total weight of the minocycline oral dosage form.

Embodiment 81

The minocycline oral dosage form of Embodiment 78, wherein said unit dosage form comprises minocycline hydrochloride in a minocycline free base equivalent amount of about 135 mg and about 22% to less than 25% of said controlled-release carrier, by weight based on the total weight of the minocycline oral dosage form.

Embodiment 82

A method of treating acne, comprising administering the minocycline oral dosage form of any one of Embodiments 73 to 81 to a subject in need thereof.

Embodiment 83

The method of Embodiment 82, comprising administering the minocycline oral dosage form to the subject at a minocycline free base equivalent dosage in the range of about 0.75 mg/kg to about 1.5 mg/kg.

Embodiment 84

The method of Embodiment 82 or 83, comprising administering the minocycline oral dosage form to the subject on a once-daily basis

Embodiment 85

The method of any one of Embodiments 82 to 84, further comprising eliminating or reducing the magnitude of at least one adverse side effect as compared to that obtained from administering substantially the same dosage of MINOCIN® immediate-release minocycline hydrochloride.

Embodiment 86

The method of any one of Embodiments 82 to 85, further comprising informing the subject that the oral dosage form may cause an adverse effect.

Embodiment 87

The method of Embodiment 86, wherein the adverse effect is selected from ear and labyrinth disorders, eye disorders, gastrointestinal disorders, immune system disorders, infections and infestations, laboratory blood abnormalities, metabolism and nutritional disorders, musculoskeletal and connective disorders, nervous system disorders, psychiatric disorders, renal and urinary disorders, reproductive system and breast disorders, respiratory, thoracic and mediastinal disorders, skin and subcutaneous tissue disorders, vascular disorders, pseudomembranous colitis, hepatotoxicity, vasculitis, tissue hyperpigmentation, and anaphylaxis.

Embodiment 88

The method of Embodiment 86, wherein the adverse effect is selected from gastrointestinal disorders, blurred vision, autoimmune syndromes, and adverse renal reactions.

Embodiment 89

A method of distributing minocycline, comprising:
distributing the minocycline oral dosage form of any one of Embodiments 73 to 81; and
concomitantly distributing information that the minocycline may cause an adverse effect.

Embodiment 90

The method of Embodiment 89, wherein the adverse effect is selected from ear and labyrinth disorders, eye disorders, gastrointestinal disorders, immune system disorders, infections and infestations, laboratory blood abnormalities, metabolism and nutritional disorders, musculoskeletal and connective disorders, nervous system disorders, psychiatric disorders, renal and urinary disorders, reproductive system and breast disorders, respiratory, thoracic and mediastinal disorders, skin and subcutaneous tissue disorders, vascular disorders, pseudomembranous colitis, hepatotoxicity, vasculitis, tissue hyperpigmentation, and anaphylaxis.

Embodiment 91

The method of Embodiment 89, wherein the adverse effect is selected from gastrointestinal disorders, blurred vision, autoimmune syndromes, and adverse renal reactions.

Embodiment 92

A method of making the minocycline oral dosage form of any one of Embodiments 73 to 81, comprising intermixing the minocycline salt and the controlled-release carrier composition to form an admixture.

Embodiment 93

The method of Embodiment 92, further comprising forming the admixture into a unit dosage form.

Embodiment 94

The method of Embodiment 93, wherein forming the admixture into the unit dosage form comprises compressing the admixture into tablets.

Embodiment 95

A kit comprising:
the minocycline oral dosage form of any one of Embodiments 1 to 26 or 73 to 81; and
information that the oral dosage form may cause one or more adverse effects.

Embodiment 96

The kit of Embodiment 95, wherein the adverse effect is selected from ear and labyrinth disorders, eye disorders, gastrointestinal disorders, immune system disorders, infections and infestations, laboratory blood abnormalities, metabolism and nutritional disorders, musculoskeletal and connective disorders, nervous system disorders, psychiatric disorders, renal and urinary disorders, reproductive system and breast disorders, respiratory, thoracic and mediastinal disorders, skin and subcutaneous tissue disorders, vascular disorders, pseudomembranous colitis, hepatotoxicity, vasculitis, tissue hyperpigmentation, and anaphylaxis.

Embodiment 97

The kit of Embodiment 95, wherein the adverse effect is selected from gastrointestinal disorders, blurred vision, autoimmune syndromes, and adverse renal reactions.

Embodiment 98

The kit of any one of Embodiments 95 to 97, further comprising instructions for administering the oral dosage form at a minocycline free base equivalent dosage of about 0.75 mg/kg to about 1.5 mg/kg.

Embodiment 99

The kit of any one of Embodiments 95 to 98, further comprising instructions for administering the oral dosage form on a once daily basis.

Embodiment 100

A kit comprising:
(i) an oral dosage form comprising:
an oral tetracycline-class antibiotic;
a fast dissolving carrier; and
a slow dissolving carrier;
wherein the fast dissolving carrier and slow dissolving carrier are at a weight ratio of 0.3 to 0.5 of fast dissolving carrier to slow dissolving carrier; and
(ii) information that the oral dosage form may cause one or more adverse effects.

Embodiment 101

The kit of Embodiment 100, wherein the ratio of fast dissolving carrier to slow dissolving carrier is 0.35 to 0.45.

Embodiment 102

The kit of Embodiment 100, wherein the ratio of fast dissolving carrier to slow dissolving carrier is about 0.36 to 0.40.

Embodiment 103

The kit of any one of Embodiments 100 to 102, wherein the one or more adverse effects is/are selected from ear and labyrinth disorders, eye disorders, gastrointestinal disorders, immune system disorders, infections and infestations, laboratory blood abnormalities, metabolism and nutritional disorders, musculoskeletal and connective disorders, nervous system disorders, psychiatric disorders, renal and urinary disorders, reproductive system and breast disorders, respiratory, thoracic and mediastinal disorders, skin and subcutaneous tissue disorders, and vascular disorders.

Embodiment 104

The kit of any one of Embodiments 100 to 102, wherein the one or more adverse effects is/are selected from gastrointestinal disorders, blurred vision, autoimmune syndromes, and adverse renal reactions.

Embodiment 105

The kit of any one of Embodiments 100 to 104, further comprising instructions for administering the oral dosage form at a dosage of about 0.75 mg/kg to about 1.5 mg/kg.

Embodiment 106

The kit of any one of Embodiments 100 to 105, further comprising instructions for administering the oral dosage form on a once-daily basis.

EXAMPLES

Example 1

A batch of 45 mg minocycline hydrochloride extended release tablets (4-hour formulation) is prepared. The tablets include 45 mg (minocycline free base equivalent) of the active ingredient minocycline hydrochloride, 108 mg of the matrix-forming polymer Methocel E50 Premium LV (hydroxypropyl methylcellulose), 197 mg intragranular of the diluent Fast Flo (lactose monohydrate), 41.0 mg extragranular of the diluent Fast Flo (lactose monohydrate), 3.0 mg of silicon oxide and 6.0 mg of the lubricant magnesium stearate Tablet formation includes high shear granulation followed by wet milling and fluid bed drying. The quantity of water used to achieve the wet granulation end point is 34% w/w of the starting materials (dry powders). Purified water is removed during drying and therefore is not present in the final tablet. The spray rate at which the granulating liquid is delivered is 5,000 g/minute. The formulation is then dry milled and blended with extragranular excipients before being compressed into tablets and subsequently film coated.

The tablets deliver approximately 90% of the active ingredient minocycline hydrochloride as free base over a 4-hour period and are suitable for use in the once-daily treatment of acne vulgaris.

Example 2

A batch of 90 mg minocycline hydrochloride extended release tablets (4-hour formulation) is prepared. The tablets include 90 mg (minocycline free base equivalent) of the active ingredient minocycline hydrochloride, 108 mg of the matrix-forming polymer Methocel E50 Premium LV (hydroxypropyl methylcellulose), 152 mg intragranular of the diluent Fast Flo (lactose monohydrate), 41.0 mg extragranular of the diluent Fast Flo (lactose monohydrate), 3.0 mg of silicon oxide and 6.0 mg of the lubricant magnesium stearate Tablet formation includes high shear granulation followed by wet milling and fluid bed drying. The quantity of water used to achieve the wet granulation end point is 34% w/w of the starting materials (dry powders). Purified water is removed during drying and therefore is not present in the final tablet. The spray rate at which the granulating liquid is delivered is 5,000 g/minute. The formulation is then dry milled and blended with extragranular excipients before being compressed into tablets and subsequently film coated.

The tablets deliver approximately 90% of the active ingredient minocycline hydrochloride as free base over a 4-hour period and are suitable for use in the once-daily treatment of acne vulgaris.

Example 3

A batch of 135 mg minocycline hydrochloride extended release tablets (4-hour formulation) is prepared. The tablets include 135 mg (minocycline free base equivalent) of the active ingredient minocycline hydrochloride, 94 mg of the matrix-forming polymer Methocel E50 Premium LV (hydroxypropyl methylcellulose), 121 mg intragranular of the diluent Fast Flo (lactose monohydrate), 41.0 mg extragranular of the diluent Fast Flo (lactose monohydrate), 3.0 mg of silicon oxide and 6.0 mg of the lubricant magnesium stearate Tablet formation includes high shear granulation followed by wet milling and fluid bed drying. The quantity of water used to achieve the wet granulation end point is 34% w/w of the starting materials (dry powders). Purified water is removed during drying and therefore is not present in the final tablet. The spray rate at which the granulating liquid is delivered is 5,000 g/minute. The formulation is then dry milled and blended with extragranular excipients before being compressed into tablets and subsequently film coated.

The tablets deliver approximately 90% of the active ingredient minocycline hydrochloride as free base over a 4-hour period and are suitable for use in the once-daily treatment of acne vulgaris.

Example 4

A batch of 150 mg minocycline hydrochloride extended release tablets (4-hour formulation) is prepared. The tablets include 150 mg (minocycline free base equivalent) of the active ingredient minocycline hydrochloride, 94 mg of the matrix-forming polymer Methocel E50 Premium LV (hydroxypropyl methylcellulose), 138 mg of the diluent Fast Flo (lactose monohydrate), 3.0 mg of silicon oxide and 6.0 mg of the lubricant magnesium stearate Tablet formation includes high shear granulation followed by wet milling and fluid bed drying. The quantity of water used to achieve the wet granulation end point is 34% w/w of the starting materials (dry powders). Purified water is removed during drying and therefore is not present in the final tablet. The spray rate at which the granulating liquid is delivered is 5,000 g/minute. The formulation is then dry milled and blended with extragranular excipients before being compressed into tablets and subsequently film coated.

The tablets deliver approximately 90% of the active ingredient minocycline hydrochloride as free base over a 4-hour period and are suitable for use in the once-daily treatment of acne vulgaris.

Example 5

A batch of 150 mg minocycline hydrochloride extended release tablets is prepared. The tablets include 36.41% of the active ingredient minocycline hydrochloride, 28.16% of the matrix-forming polymer Methocel E50 Premium LV (hydroxypropyl methylcellulose), 20.39% intragranular of the diluent Fast Flo (lactose monohydrate), 10.68% extragranular of the diluent Fast Flo (lactose monohydrate), 0.97% of the glidants Cab-O-Sil (colloidal silicon oxide), 0.49% of the lubricant magnesium stearate, and 2.91% of the non-functional film coat OpaDry II.

Example 6

A batch of 150 mg minocycline hydrochloride extended release tablets (4-hour formulation) is prepared. The tablets include 36.41% of the active ingredient minocycline hydrochloride, 22.82% of the matrix-forming polymer Methocel E50 Premium LV (hydroxypropyl methylcellulose), 25.73% intragranular of the diluent Fast Flo (lactose monohydrate), 10.68% extragranular of the diluent Fast Flo (lactose monohydrate), 0.97% of the glidants Cab-O-Sil (colloidal silicon oxide), 0.49% of the lubricant magnesium stearate, and 2.91% of the non-functional film coat OpaDry II. The tablets are formed using appropriate tablet-making methods. Purified water is removed during drying and therefore is not present in the final tablet.

The dissolution properties of the tablets are measured under various storage conditions as shown below:

| Conditions | 1 hr | 2 hr | 4 hr | 6 hr | >6 hr |
|---|---|---|---|---|---|
| Initial | 38 | 57 | 83 | 96 | 100 |
| 25° C./60% RH | | | | | |
| 1 month | 42 | 69 | 95 | 98 | 99 |
| 3 month | 36 | 59 | 87 | 95 | 95 |
| 6 month | 40 | 60 | 89 | 98 | 98 |
| 9 month | 39 | 57 | 83 | 98 | 98 |
| 40° C./60% RH | | | | | |
| 1 month | 42 | 70 | 97 | 99 | 99 |
| 3 month | 38 | 60 | 89 | 97 | 97 |
| 6 month | 43 | 62 | 88 | 97 | 97 |

Example 7

A batch of 200 mg minocycline hydrochloride extended release tablet (4-hour formulation) is prepared. The tablets include 48.54% of the active ingredient minocycline hydrochloride, 22.82% of the matrix-forming polymer Methocel E50 Premium LV (hydroxypropyl methylcellulose), 13.59% intragranular of the diluent Fast Flo (lactose monohydrate), 10.19% extragranular of the diluent Fast Flo (lactose monohydrate), 0.97% of the glidants Cab-O-Sil (colloidal silicon oxide), 0.97% of the lubricant magnesium stearate, and 2.91% of the non-functional film coat Opa Dry II. The tablets are formed using appropriate tablet-making methods. Purified water is removed during drying and therefore is not present in the final tablets.

The dissolution properties of the tablets are measured under various storage conditions as shown below:

| Conditions | 1 hr | 2 hr | 4 hr | 6 hr | >6 hr |
|---|---|---|---|---|---|
| Initial | 33 | 63 | 80 | 93 | 93 |
| 25° C./60% RH | | | | | |
| 1 month | 32 | 45 | 71 | 89 | 92 |
| 3 month | 31 | 53 | 77 | 91 | 93 |
| 6 month | 32 | 50 | 78 | 94 | 95 |
| 40° C./60% RH | | | | | |
| 1 month | 33 | 47 | 73 | 89 | 92 |
| 3 month | 35 | 56 | 80 | 92 | 94 |
| 6 month | 32 | 51 | 78 | 94 | 95 |

Example 8

A batch of 180 mg minocycline hydrochloride extended release tablets (4-hour formulation) is prepared. The tablets include 43.69% of the active ingredient minocycline hydrochloride, 22.82% of the matrix-forming polymer Methocel E50 Premium LV (hydroxypropyl methylcellulose), 18.45% intragranular of the diluent Fast Flo (lactose monohydrate), 10.19% extragranular of the diluent Fast Flo (lactose monohydrate), 0.97% of the glidants Cab-O-Sil (colloidal silicon oxide), 0.97% of the lubricant magnesium stearate, and 2.91% of the non-functional film coat Opa Dry II. The tablets are formed using appropriate tablet-making methods. Purified water is removed during drying and therefore is not present in the final tablet.

Example 9

A batch of 135 mg minocycline hydrochloride extended release tablets (4-hour formulation) is prepared. The tablets include 32.77% of the active ingredient minocycline hydrochloride, 22.82% of the matrix-forming polymer Methocel E50 Premium LV (hydroxypropyl methylcellulose), 13.59% intragranular of the diluent Fast Flo (lactose monohydrate), 22.82% extragranular of the diluent Fast Flo (lactose monohydrate), 0.73% of the glidants Cab-O-Sil (colloidal silicon oxide), 0.73% of the lubricant magnesium stearate, and 2.91% of the non-functional film coat Opa Dry II. The tablets are formed using appropriate tablet-making methods. Purified water is removed during drying and therefore is not present in the final tablet.

The dissolution properties of the tablets are measured under various storage conditions as shown below:

| Conditions | 1 hr | 2 hr | 4 hr | 6 hr | >6 hr |
|---|---|---|---|---|---|
| Initial | 38 | 52 | 79 | 95 | 97 |
| 25° C./60% RH | | | | | |
| 1 month | 39 | 55 | 79 | 94 | 96 |
| 3 month | 37 | 57 | 86 | 98 | 97 |
| 6 month | 37 | 56 | 87 | 96 | 96 |
| 9 month | 37 | 57 | 83 | 97 | 98 |
| 40° C./60% RH | | | | | |
| 1 month | 40 | 55 | 81 | 95 | 96 |
| 3 month | 37 | 59 | 86 | 96 | 97 |

Example 10

A batch of 90 mg minocycline hydrochloride extended release tablets (4-hour formulation) are prepared. The tablets include 32.77% of the active ingredient minocycline hydrochloride, 26.21% of the matrix-forming polymer Methocel E50 Premium LV (hydroxypropyl methylcellulose), 36.89% intragranular of the diluent Fast Flo (lactose monohydrate), 10.68% extragranular of the diluent Fast Flo (lactose monohydrate), 0.73% of the glidants Cab-O-Sil (colloidal silicon oxide), 0.73% of the lubricant magnesium stearate, and 2.91% of the non-functional film coat Opa Dry II. The tablets are formed using appropriate tablet-making methods. Purified water is removed during drying and therefore is not present in the final tablet.

Example 11

A batch of 45 mg minocycline hydrochloride extended release tablets (4-hour formulation) is prepared. The tablets include 10.92% of the active ingredient minocycline hydrochloride, 26.21% of the matrix-forming polymer Methocel E50 Premium LV (hydroxypropyl methylcellulose), 47.28% intragranular of the diluent Fast Flo (lactose monohydrate), 10.92% extragranular of the diluent Fast Flo (lactose monohydrate), 0.73% of the glidants Cab-O-Sil (colloidal silicon oxide), 0.49% of the lubricant magnesium stearate, and 2.91% of the non-functional film coat Opa Dry II. The tablets are formed using appropriate tablet-making methods. Purified water is removed during drying and therefore is not present in the final tablet.

The dissolution properties of the tablets are measured under various storage conditions as shown below:

| Conditions | 1 hr | 2 hr | 4 hr | 6 hr | >6 hr |
|---|---|---|---|---|---|
| Initial 25° C./60% RH | 39 | 54 | 85 | 92 | 92 |
| 1 month | 40 | 58 | 94 | 95 | 95 |
| 3 month | 40 | 58 | 93 | 93 | 93 |
| 6 month | 38 | 52 | 77 | 91 | 95 |
| 40° C./60% RH | | | | | |
| 1 month | 38 | 60 | 93 | 94 | 94 |
| 3 month | 40 | 58 | 91 | 93 | 93 |

Example 12

A purpose of this single-dose, four-way crossover, dose proportionality study is to determine the pharmacokinetics of minocycline after giving increasing doses to normal healthy subjects under fasted conditions. These data are evaluated statistically to determine the dose proportionality of the different strengths of the controlled-release (CR) minocycline unit dosage formulations and to compare the minocycline bioavailability of the these controlled-release formulations to that of commercially available immediate-release MINOCIN® capsules.

The study is performed as a single-dose four-way crossover, dose proportionality study using increasing doses of minocycline with an adequate washout period (7 days) between subsequent periods of the study. An equal number of subjects are randomly assigned to each of four dosing sequences (ABCD, BCDA, CDAB, DABC) to receive the study treatments, 2×45 mg caplets (A), 1×90 mg Caplet (B), 1×135 mg caplet (C) and 1×100 mg MINOCIN® capsule (D).

The study conduct is consistent with Good Clinical Practice (GCP) and regulatory requirements of the U.S. Food and Drug Administration. Venous blood samples are collected over a 72-hour period of time post drug administration. Medical care of the volunteers is assured by the presence of a physician for at least 4 hours post dose and the physician is on-call throughout the blood-sampling period. Professional medical personnel are on site during the entire study confinement period. Subjects are confined in the clinical facility for at least 10 hours before dosing and for 24 hours after dosing. Subjects are discharged after the 24-hour blood sample and return as outpatients for the remaining blood samples. Standardized meals are served and no caffeine, alcohol, or grapefruit-containing foods or beverages are allowed to be consumed 24 hours before dosing or throughout study confinement.

All subjects fast for at least 10 hours before dosing and remain fasted for 4 hours post drug administration. From 1 hour before, through 1 hour after drug administration, only the water supplied with the drug is permitted. After this time, water is permitted ad lib. Four hours after drug administration, a standardized boxed lunch is served.

The study drugs are administered per randomization code together with 240 mL of tepid water and a mouth check is performed. The time of drug administration is defined as study time=0 in each period. All further study times indicated refer to this time.

No serious adverse events are reported during the entire course of the study. There are nine (9) adverse events, including vaginal itching (2), nausea (1), nasal congestion (1), cough (1), itchy (1), rash (1), headache (1) and stomach pain (1). A summary of the Adverse Events is provided in Table 1.

TABLE 1

Summary of Adverse Events

| Subj # | Trt (1) | Adverse Event | Sev (2) | Out (3) | Act (4) | Occur (5) | Rel (6) |
|---|---|---|---|---|---|---|---|
| 1 | A | Vaginal Itching | 1 | 1 | 1 | 1 | 2 |
| 1 | B | Vaginal Itching | 1 | 1 | 1 | 1 | 2 |
| 1 | C | Nausea | 1 | 1 | 2 | 2 | 3 |
| 4 | D | Nasal Congestion | 1 | 1 | 2 | 1 | 2 |
| 4 | D | Cough | 1 | 1 | 2 | 1 | 2 |
| 17 | C | Itchy | 1 | 1 | 2 | 2 | 2 |
| 17 | C | Rash | 1 | 1 | 2 | 2 | 3 |
| 18 | C | Headache | 1 | 1 | 2 | 2 | 3 |
| 22 | B | Stomach Pain | 1 | 1 | 2 | 2 | 3 |

(1) Treatment: A = Test 2 × 45 mg, B = Test 90 mg, C = Test 135 mg, D = Reference 100 mg, NA = Not applicable (pre-dose)
(2) Severity of Adverse Event: 1-Mild, 2-Moderate, 3-Severe
(3) Outcome: 1-Resolved, 2-AE Continuing, 3-Subject Lost to Follow-up, 4-Other
(4) Action Taken: 1-None, 2-Increased Surveillance, 3-Medication, 4-Suspend Study Medication, 5-Other (specify)
(5) Occurrence: 1-Intermittent, 2-Continuous
(6) Relationship to Drug (Possible Cause): 1-None, 2-Remote, 3-Possible, 4-Probable, 5-Definite Blood samples (1×7 mL) are drawn from an antecubital or forearm vein into sodium heparin vacuum tubes and are obtained according to Table 2.

TABLE 2

| Day | Procedure | Collection | Time | Hours* (relative to dosing) |
|---|---|---|---|---|
| −1 | Confinement | | 1900 | |
| | Snack (provided, not required) | | 2000 | |
| | Fasting Begins | | 2100 | −10 |
| 0 | Vital Signs | | 0530 | |
| | Water restriction begins | | 0600 | −1.0 |
| | | 1 | 0615 | Pre Dose (0) |
| | Dosing | | 0700 | 0 |
| | | 2 | 0730 | 0.5 |
| | Water restriction ends | 3 | 0800 | 1 |
| | | 4 | 0830 | 1.5 |
| | | 5 | 0900 | 2 |
| | | 6 | 1000 | 3 |
| | Lunch (after sample) | 7 | 1100 | 4 |
| | | 8 | 1200 | 5 |
| | | 9 | 1300 | 6 |
| | | 10 | 1500 | 8 |

TABLE 2-continued

| Day | Procedure | Collection | Time | Hours* (relative to dosing) |
|---|---|---|---|---|
| | Dinner (after sample) | 11 | 1700 | 10 |
| | | 12 | 1900 | 12 |
| | Snack | | 2000 | |
| 1 | Discharge | 13 | 0700 | 24 |
| | Safety Labs (P2 only) | | | |
| | Outpatient Return Sample | 14 | 1900 | 36 |
| 2 | Outpatient Return Sample | 15 | 0700 | 48 |
| 3 | Outpatient Return Sample | 16 | 0700 | 72 |

Approximately 448 mL of blood are obtained for the pharmacokinetic samples. Blood samples are centrifuged until separation of red cells from plasma occurs. Plasma is transferred into a polypropylene tube and placed into a freezer within one hour of sample collection. Plasma samples are stored at a temperature at or below −20°±5° C. until transferred to the analytical laboratory for analysis.

The study is performed in accordance with the protocol for all essential parts except as outlined below. Discharge labs are not performed for subjects #5, 15, and 20 who withdraw consent after periods 1, 3 and 1 respectively. There are 9 significant deviations to the blood draw schedule. These are reported to the study Biostatistician.

The sample storage freezer temperature rises beyond −15° C. for short periods of time during the study. These deviations are caused by frequent placement of samples into the freezer or by sample preparation for shipment. None of the frozen samples thaws during these times.

Samples are analyzed for the content of minocycline by a fully-validated HPLC/UV assay.

Calibration standards and controls are prepared by spiking human, interference-free, plasma with the minocycline HCl reference material. Calibration standards are prepared to contain minocycline concentrations of 25.0, 50.0, 100, 250, 500, 750, 1000, 2500, and 5000 ng/mL. Quality control samples are prepared to contain concentrations of 40.0 ng/mL, 800 ng/mL, and 4000 ng/mL.

The assay method involves protein precipitation with perchloric acid followed by column switching and chromatographic separation of minocycline and the internal standard, demeclocycline, on an RP18 column. Detection and peak quantification are based on UV absorbance at 351 nm. Samples are analyzed in runs that consist of a control sample, control blanks with and without internal standard one set of calibration standards, two sets of quality control samples, and typically the samples from two subjects, both periods.

The peak height response ratio (analyte-to-internal) for each calibration standard is plotted as a function of concentration. A linear regression is calculated by the method of weighted least-squares using the inverse of concentration (1/x) as a weighting factor. A calculated concentration is determined for each standard quality control sample and subject sample from the calibration line. The analyte concentrations in samples and controls are estimated from the calibration line by use of the equation:

(Ratio−Intercept)/Slope

The coefficient of variation for the calculated concentrations for the quality control samples ranges from 4.9% to 7.9%. The apparent bias (% deviation of the mean from known concentration) for the calculated concentrations for the quality control samples ranges from −5.7% to +2.0%. The coefficient of variation for the back-calculated concentrations of the calibration standards ranges from 2.0% to 6.1%. The bias for the back-calculated concentrations of the calibration standards ranges from −3.2% to +2.4%. The lower limit of quantification of the assay is established at 25.0 ng/mL. Any sample whose calculated concentration is below this limit is reported as less than this lower limit. The assay is linear over the concentration range of 25.0 ng/mL to 5000 ng/mL.

The available data from the 19 subjects who completed all four periods of the study are used in the pharmacokinetic analyses. Pharmacokinetic calculations are performed using SAS (PC version 6.12). Any sample concentration reported less than the assay limit of quantitation are set to zero for use in the pharmacokinetic and statistical analyses.

Pharmacokinetic parameters (areas, times to peak and elimination rates) are calculated using the times of sample collection corrected for any reported deviations in collection time. Graphical presentations of individual subject results also use the corrected times of sample collection. Graphical presentations of mean results use the scheduled times of sample collection.

Peak concentration ($C_{max}$) is the observed maximum value during the collection period of 0 to 72 hours. The time to peak concentration ($T_{max}$) is the time at which $C_{max}$ is observed (or first observed, if the peak value occurred at more than one time).

The apparent first-order elimination rate constant (Ke) is estimated as the negative value of the slope of the regression line for the terminal log-linear concentration-time values. A minimum of three terminal values are used to obtain an estimate. The values included in the regression analyses are determined by examination of the individual subject plots of natural logarithm of concentration against time. Elimination half-life (T½) is estimated as $\log_e(2)/Ke$.

Area under the curve ($AUC_{0-t}$) to the last measured concentration ($C_t$) are calculated by the linear trapezoidal method. Area to infinite time ($AUC_{inf}$) is calculated by extrapolating $AUC_{0-t}$, by the addition of the quantity: $C_t/Ke$.

Statistical analyses are performed using the General Linear Models (GLM) procedure of the SAS statistical program (PC version 6.12). The pharmacokinetic parameter estimates, as well as the concentrations at each scheduled sample time are evaluated by analysis of variance.

Statistical analyses are conducted on the pharmacokinetic values derived from the reported minocycline concentrations and also on the values following dose adjustment to a common 100 mg dose. The dose adjustment is accomplished by multiplying the area and $C_{max}$ values for each subject in each period by the ratio 100/Dose, where Dose is that administered in the given period.

The statistical model contains main effects of sequence, subject nested within sequence, treatment and period. F-ratios for testing main effects are constructed using the mean square term for the effect as the numerator and the mean square error term from the ANOVA as the denominator. The F-ratio to test for sequence effects is constructed using the type II mean square term for sequence as the numerator and type II mean square for subjects nested within sequence as the denominator. Hypothesis testing for treatment effects in the analysis is conducted at $\alpha=0.05$.

When statistically significant differences are detected ($p<0.05$), possible pair-wise comparisons of treatment means are conducted to determine if the significance can be attributed to the difference between one or more pairs of treatments. These pair-wise comparisons are performed at an adjusted $\alpha=0.0085$ level to maintain the overall experimental error rate at 0.05.

Pair-wise comparisons of interest are those between each of the three controlled-release compositions comprising minocycline hydrochloride at various strengths (45 mg, 90 mg and 135 mg) and MINOCIN® capsules for assessing relative bioavailability. Of interest for evaluating the dose-proportionality of the three controlled-release compositions are the three pair-wise comparisons 45 mg vs. 90 mg, 45 mg vs. 135 mg and 90 mg vs. 135 mg.

The intra-subject coefficient of variation is estimated from the mean square error term (MSE) of the ln-transformed (loge) results as:

$$100\% * SQRT(e^{MSE}-1)$$

Confidence Intervals (90%) for the area and peak concentration comparisons of interest are calculated by the t-test approach (2, 1-sided) at α=0.10 overall, α=0.05 each side:

$$\text{Interval Lower Limit} = (X_T - X_R) - Se * t_{\alpha/2}$$

$$\text{Interval Lower Limit} = (X_T - X_R) - Se * t_{\alpha/2}$$

Where $X_T$, $X_R$ are the Test and Reference least-squares means in each comparison of interest, respectively.

Se is the standard error of the estimated difference between means from the SAS estimate statement.

$T_{\alpha/2}$ is the critical value from the t-distribution with degrees of freedom that of the error term and α=0.10.

For ln-transformed data the interval is calculated from the ANOVA results on the transformed values and then exponentiated to convert to the non-transformed scale:

$$\text{Interval Limit} = e^{(log\text{-}transformed\ interval\ limit)}$$

The intervals are computed for the "true" mean treatment differences, expressed as a percent of the reference mean for the comparison, and true geometric mean ratios (from logarithmic transformation).

There are no serious adverse events observed or reported during the study. Clinical laboratory parameters (clinical chemistry and hematology) are obtained at the end of the final period of subject confinement. No clinically significant laboratory abnormalities are observed.

Statistical analyses are performed to compare each of the three controlled-release (CR) caplets to each other and to the MINOCIN® capsule. Tables 3-4 summarize the mean results for the major pharmacokinetic parameters for each of the treatments before and after dose adjustment. Table 5 summarizes the comparisons of the controlled-release caplets to the MINOCIN® capsule. Table 6 summarizes the comparisons conducted to evaluate the dose-proportionality of the three controlled-release caplets.

TABLE 3

Summary of pharmacokinetic results (least-squares means, not dose-adjusted)

| Parameter | 45-mg CR (2 × 45 mg Dose) | 90-mg CR (1 × 90 mg Dose) | 135-mg CR (1 × 135 mg Dose) | MINOCIN® (1 × 100 mg Dose) |
|---|---|---|---|---|
| | Least-Squares Arithmetic Means | | | |
| $AUC_{0\text{-}t}$ (ng-hr/mL) | 25920 | 25732 | 38718 | 33595 |
| $AUC_{inf}$ (ng-hr/mL) | 27828 | 27631 | 41228 | 35702 |
| $C_{max}$ (ng/mL) | 1193 | 1171 | 1829 | 1661 |
| | Least-Squares Geometric Means | | | |
| $AUC_{0\text{-}t}$ (ng-hr/mL) | 24524 | 24733 | 37356 | 32340 |
| $AUC_{inf}$ (ng-hr/mL) | 26329 | 26470 | 39715 | 34335 |
| $C_{max}$ (ng/mL) | 1130 | 1125 | 1766 | 1596 |

TABLE 4

Summary of pharmacokinetic results (least-squares means, dose-adjusted)

| Parameter | 45-mg CR (2 × 45 mg Dose) | 90-mg CR (1 × 90 mg Dose) | 135-mg CR (1 × 135 mg Dose) | MINOCIN® (1 × 100 mg Dose) |
|---|---|---|---|---|
| | Least-Squares Arithmetic Means | | | |
| $AUC_{0\text{-}t}$ (ng-hr/mL) | 28769 | 28573 | 28748 | 33598 |
| $AUC_{inf}$ (ng-hr/mL) | 30886 | 30684 | 30611 | 35702 |
| $C_{max}$ (ng/mL) | 1326 | 1300 | 1358 | 1661 |
| $T_{max}$ (hour) | 3.96 | 3.90 | 3.85 | 2.92 |
| Ke (1/hour) | 0.0424 | 0.0424 | 0.0425 | 0.0429 |
| T½ (hour) | 16.9 | 17.1 | 16.7 | 16.5 |
| | Least-Squares Geometric Means | | | |
| $AUC_{0\text{-}t}$ (ng-hr/mL) | 27249 | 27481 | 27671 | 32340 |

TABLE 4-continued

Summary of pharmacokinetic results (least-squares means, dose-adjusted)

| Parameter | 45-mg CR (2 × 45 mg Dose) | 90-mg CR (1 × 90 mg Dose) | 135-mg CR (1 × 135 mg Dose) | MINOCIN ® (1 × 100 mg Dose) |
|---|---|---|---|---|
| $AUC_{inf}$ (ng-hr/mL) | 29254 | 29411 | 29418 | 34335 |
| $C_{max}$ (ng/mL) | 1255 | 1250 | 1308 | 1596 |

TABLE 5

Summary of statistical comparisons between minocycline CR and MINOCIN ® capsules (dose-adjusted)

| | Least-Squares CR-to-MINOCIN ® Ratios* | | | | | |
|---|---|---|---|---|---|---|
| CR Caplet | $AUC_{0-t}$ (ng-hr/mL) | $AUC_{inf}$ (ng-hr/mL) | $C_{max}$ (ng/mL) | $T_{max}$ (hour) | Ke (1/hour) | T½ (hour) |
| 45-mg (2 × 45 mg Dose) | 0.843 | 0.852 | 0.787 | 1.355 | 0.988 | 1.024 |
| 90-mg (1 × 90 mg Dose) | 0.850 | 0.857 | 0.783 | 1.336 | 0.990 | 1.032 |
| 135-mg (1 × 135 mg Dose) | 0.856 | 0.857 | 0.820 | 1.317 | 0.992 | 1.008 |

*For $AUC_{0-t}$, $AUC_{0-\infty}$ and $C_{max}$ results are geometric mean ratios; for other parameters, results are arithmetic mean ratios. All comparisons are detected as statistically significant by ANOVA ($\alpha = 0.05$) except for those involving the elimination parameters Ke and T½.

TABLE 6

Summary of statistical comparisons of dose-proportionality between CR caplets (dose-adjusted results)

| | Least-Squares Geometric Means Ratios* | | |
|---|---|---|---|
| CR Caplet | $AUC_{0-t}$ (ng-hr/mL) | $AUC_{inf}$ (ng-hr/mL) | $C_{max}$ (ng/mL) |
| 45-mg vs. 90-mg | 0.992 | 0.995 | 1.005 |
| 45-mg vs. 135-mg | 0.985 | 0.994 | 0.959 |
| 90-mg vs. 135-mg | 0.993 | 1.000 | 0.955 |

*The 90% confidence intervals for all geometric means ratios are contained within the bioequivalence interval 0.80 to 1.25, indicating dose-proportionality between all caplet strengths.

Tables 7-12 show pair-wise comparisons of the pharmacokinetic variables and show 90% confidence intervals on the ratios of the variables.

TABLE 7

| | Least-Squares Means[1] | | Ratio[2] | CV %[3] | 90% Confidence Interval[4] | |
|---|---|---|---|---|---|---|
| Parameter | 45-mg CR | MINOCIN ® | | | Lower | Upper |
| $AUC_{0-t}$ (ng-hr/mL) | 28769 | 33598 | 0.856* | — | 0.801 | 0.911 |
| $AUC_{inf}$ (ng-hr/mL) | 30886 | 35702 | 0.865* | — | 0.812 | 0.918 |
| $C_{max}$ (ng/mL) | 1326 | 1661 | 0.798* | — | 0.729 | 0.867 |
| $T_{max}$ (hour) | 3.96 | 2.92 | 1.355* | — | — | — |
| Ke (1/hour) | 0.0424 | 0.0429 | 0.988 | — | — | — |
| T½ (hour) | 16.9 | 16.5 | 1.024 | — | — | — |
| Ln-Transformed: | | | | | | |
| $AUC_{0-t}$ (ng-hr/mL) | 27249 | 32340 | 0.843* | 10.8 | 0.795 | 0.893 |
| $AUC_{inf}$ (ng-hr/mL) | 29254 | 34335 | 0.852* | 10.4 | 0.805 | 0.902 |

TABLE 7-continued

|  | Least-Squares Means[1] | | Ratio[2] | CV %[3] | 90% Confidence Interval[4] | |
|---|---|---|---|---|---|---|
| Parameter | 45-mg CR | MINOCIN ® | | | Lower | Upper |
| $C_{max}$ (ng/mL) | 1255 | 1596 | 0.787* | 13.2 | 0.732 | 0.845 |

[1] Least-squares geometric means for ln-transformed data.
[2] Ratio calculated as the 45-mg least-squares mean divided by the MINOCIN ® capsules least-squares mean.
[3] Estimated intra-subject coefficient of variation, CV % = 100 * SQRT($e^{MSE}$ − 1), where MSE is the mean square error term from the ANOVA.
[4] Confidence interval on the ratio.
*Comparison is detected as statistically significant by ANOVA ($\alpha$ = 0.05).

TABLE 8

|  | Least-Squares Means[1] | | Ratio[2] | CV %[3] | 90% Confidence Interval[4] | |
|---|---|---|---|---|---|---|
| Parameter | 90-mg CR | MINOCIN ® | | | Lower | Upper |
| $AUC_{0-t}$ (ng-hr/mL) | 28573 | 33598 | 0.850* | — | 0.795 | 0.905 |
| $AUC_{inf}$ (ng-hr/mL) | 30684 | 35702 | 0.859* | — | 0.806 | 0.912 |
| $C_{max}$ (ng/mL) | 1300 | 1661 | 0.782* | — | 0.714 | 0.851 |
| $T_{max}$ (hour) | 3.90 | 2.92 | 1.336* | — | — | — |
| Ke (1/hour) | 0.0424 | 0.0429 | 0.990 | — | — | — |
| T½ (hour) | 17.1 | 16.5 | 1.032 | — | — | — |
| Ln-Transformed: | | | | | | |
| $AUC_{0-t}$ (ng-hr/mL) | 27481 | 32340 | 0.850* | 10.8 | 0.801 | 0.901 |
| $AUC_{inf}$ (ng-hr/mL) | 29411 | 34335 | 0.857* | 10.4 | 0.809 | 0.906 |
| $C_{max}$ (ng/mL) | 1250 | 1596 | 0.783* | 13.2 | 0.729 | 0.841 |

[1] Least-squares geometric means for ln-transformed data.
[2] Ratio calculated as the 90-mg least-squares mean divided by the MINOCIN ® capsules least-squares mean.
[3] Estimated intra-subject coefficient of variation, CV % = 100 * SQRT($e^{MSE}$ − 1), where MSE is the mean square error term from the ANOVA.
[4] Confidence interval on the ratio.
*Comparison is detected as statistically significant by ANOVA ($\alpha$ = 0.05).

TABLE 9

|  | Least-Squares Means[1] | | Ratio[2] | CV %[3] | 90% Confidence Interval[4] | |
|---|---|---|---|---|---|---|
| Parameter | 135-mg CR | MINOCIN ® | | | Lower | Upper |
| $AUC_{0-t}$ (ng-hr/mL) | 28748 | 33598 | 0.856* | — | 0.801 | 0.911 |
| $AUC_{inf}$ (ng-hr/mL) | 30611 | 35702 | 0.857* | — | 0.804 | 0.910 |
| $C_{max}$ (ng/mL) | 1358 | 1661 | 0.817* | — | 0.749 | 0.886 |
| $T_{max}$ (hour) | 3.85 | 2.92 | 1.317* | — | — | — |
| Ke (1/hour) | 0.0425 | 0.0429 | 0.992 | — | — | — |
| T½ (hour) | 16.7 | 16.5 | 1.008 | — | — | — |
| Ln-Transformed: | | | | | | |
| $AUC_{0-t}$ (ng-hr/mL) | 27671 | 32340 | 0.856* | 10.8 | 0.807 | 0.907 |
| $AUC_{inf}$ (ng-hr/mL) | 29418 | 34335 | 0.857* | 10.4 | 0.810 | 0.907 |

TABLE 9-continued

| | Least-Squares Means[1] | | Ratio[2] | CV %[3] | 90% Confidence Interval[4] | |
|---|---|---|---|---|---|---|
| Parameter | 135-mg CR | MINOCIN ® | | | Lower | Upper |
| $C_{max}$ (ng/mL) | 1308 | 1596 | 0.820* | 13.2 | 0.763 | 0.881 |

[1] Least-squares geometric means for ln-transformed data.
[2] Ratio calculated as the 135-mg least-squares mean divided by the MINOCIN ® capsules least-squares mean.
[3] Estimated intra-subject coefficient of variation, CV % = 100 * SQRT($e^{MSE} - 1$), where MSE is the mean square error term from the ANOVA.
[4] Confidence interval on the ratio.
*Comparison is detected as statistically significant by ANOVA ($\alpha = 0.05$).

TABLE 10

| | Least-Squares Means[1] | | Ratio[2] | CV %[3] | 90% Confidence Interval[4] | |
|---|---|---|---|---|---|---|
| Parameter | 45-mg CR | 90-mg CR | | | Lower | Upper |
| $AUC_{0-t}$ (ng·hr/mL) | 28769 | 28573 | 1.007 | — | 0.942 | 1.072 |
| $AUC_{inf}$ (ng·hr/mL) | 30886 | 30684 | 1.007 | — | 0.945 | 1.068 |
| $C_{max}$ (ng/mL) | 1326 | 1300 | 1.020 | — | 0.932 | 1.108 |
| $T_{max}$ (hour) | 3.96 | 3.90 | 1.014 | — | — | — |
| Ke (1/hour) | 0.0424 | 0.0424 | 0.998 | — | — | — |
| T½ (hour) | 16.9 | 17.1 | 0.992 | — | — | — |
| Ln-Transformed: | | | | | | |
| $AUC_{0-t}$ (ng·hr/mL) | 27249 | 27481 | 0.992 | 10.8 | 0.935 | 1.051 |
| $AUC_{inf}$ (ng·hr/mL) | 29254 | 29411 | 0.995 | 10.4 | 0.940 | 1.053 |
| $C_{max}$ (ng/mL) | 1255 | 1250 | 1.005 | 13.2 | 0.935 | 1.079 |

[1] Least-squares geometric means for ln-transformed data.
[2] Ratio calculated as the 45-mg least-squares mean divided by the 90-mg least-squares mean. None of the comparisons are detected as statistically significant by ANOVA ($\alpha = 0.05$).
[3] Estimated intra-subject coefficient of variation, CV % = 100 * SQRT($e^{MSE} - 1$), where MSE is the mean square error term from the ANOVA.
[4] Confidence interval on the ratio.

TABLE 11

| | Least-Squares Means[1] | | Ratio[2] | CV %[3] | 90% Confidence Interval[4] | |
|---|---|---|---|---|---|---|
| Parameter | 45-mg CR | 135-mg CR | | | Lower | Upper |
| $AUC_{0-t}$ (ng·hr/mL) | 28769 | 28748 | 1.001 | — | 0.936 | 1.065 |
| $AUC_{inf}$ (ng·hr/mL) | 30886 | 30611 | 1.009 | — | 0.947 | 1.071 |
| $C_{max}$ (ng/mL) | 1326 | 1358 | 0.976 | — | 0.892 | 1.060 |
| $T_{max}$ (hour) | 3.96 | 3.85 | 1.029 | — | — | — |
| Ke (1/hour) | 0.0424 | 0.0425 | 0.996 | — | — | — |
| T½ (hour) | 16.9 | 16.7 | 1.016 | — | — | — |
| Ln-Transformed: | | | | | | |
| $AUC_{0-t}$ (ng·hr/mL) | 27249 | 27671 | 0.985 | 10.8 | 0.929 | 1.044 |
| $AUC_{inf}$ (ng·hr/mL) | 29254 | 29418 | 0.994 | 10.4 | 0.940 | 1.052 |

TABLE 11-continued

| Parameter | Least-Squares Means[1] | | Ratio[2] | CV %[3] | 90% Confidence Interval[4] | |
|---|---|---|---|---|---|---|
| | 45-mg CR | 135-mg CR | | | Lower | Upper |
| $C_{max}$ (ng/mL) | 1255 | 1308 | 0.959 | 13.2 | 0.893 | 1.031 |

[1]Least-squares geometric means for ln-transformed data.
[2]Ratio calculated as the 45-mg least-squares mean divided by the 135-mg least-squares mean. None of the comparisons are detected as statistically significant by ANOVA ($\alpha = 0.05$).
[3]Estimated intra-subject coefficient of variation, CV % = 100 * SQRT($e^{MSE}$ – 1), where MSE is the mean square error term from the ANOVA.
[4]Confidence interval on the ratio.

TABLE 12

| Parameter | Least-Squares Means[1] | | Ratio[2] | CV %[3] | 90% Confidence Interval[4] | |
|---|---|---|---|---|---|---|
| | 90-mg CR | 135-mg CR | | | Lower | Upper |
| $AUC_{0-t}$ (ng-hr/mL) | 28573 | 28748 | 0.994 | — | 0.930 | 1.058 |
| $AUC_{inf}$ (ng-hr/mL) | 30684 | 30611 | 1.002 | — | 0.941 | 1.064 |
| $C_{max}$ (ng/mL) | 1300 | 1358 | 0.957 | — | 0.873 | 1.041 |
| $T_{max}$ (hour) | 3.90 | 3.85 | 1.015 | — | — | — |
| Ke (1/hour) | 0.0424 | 0.0425 | 0.998 | — | — | — |
| T½ (hour) | 17.1 | 16.7 | 1.024 | — | — | — |
| Ln-Transformed: | | | | | | |
| $AUC_{0-t}$ (ng-hr/mL) | 27481 | 27671 | 0.993 | 10.8 | 0.937 | 1.053 |
| $AUC_{inf}$ (ng-hr/mL) | 29411 | 29418 | 1.000 | 10.4 | 0.945 | 1.058 |
| $C_{max}$ (ng/mL) | 1250 | 1308 | 0.955 | 13.2 | 0.889 | 1.026 |

[1]Least-squares geometric means for ln-transformed data.
[2]Ratio calculated as the 90-mg least-squares mean divided by the 135-mg least-squares mean. None of the comparisons are detected as statistically significant by ANOVA ($\alpha = 0.05$).
[3]Estimated intra-subject coefficient of variation, CV % = 100 * SQRT($e^{MSE}$ – 1), where MSE is the mean square error term from the ANOVA.
[4]Confidence interval on the ratio.

Figure 2:
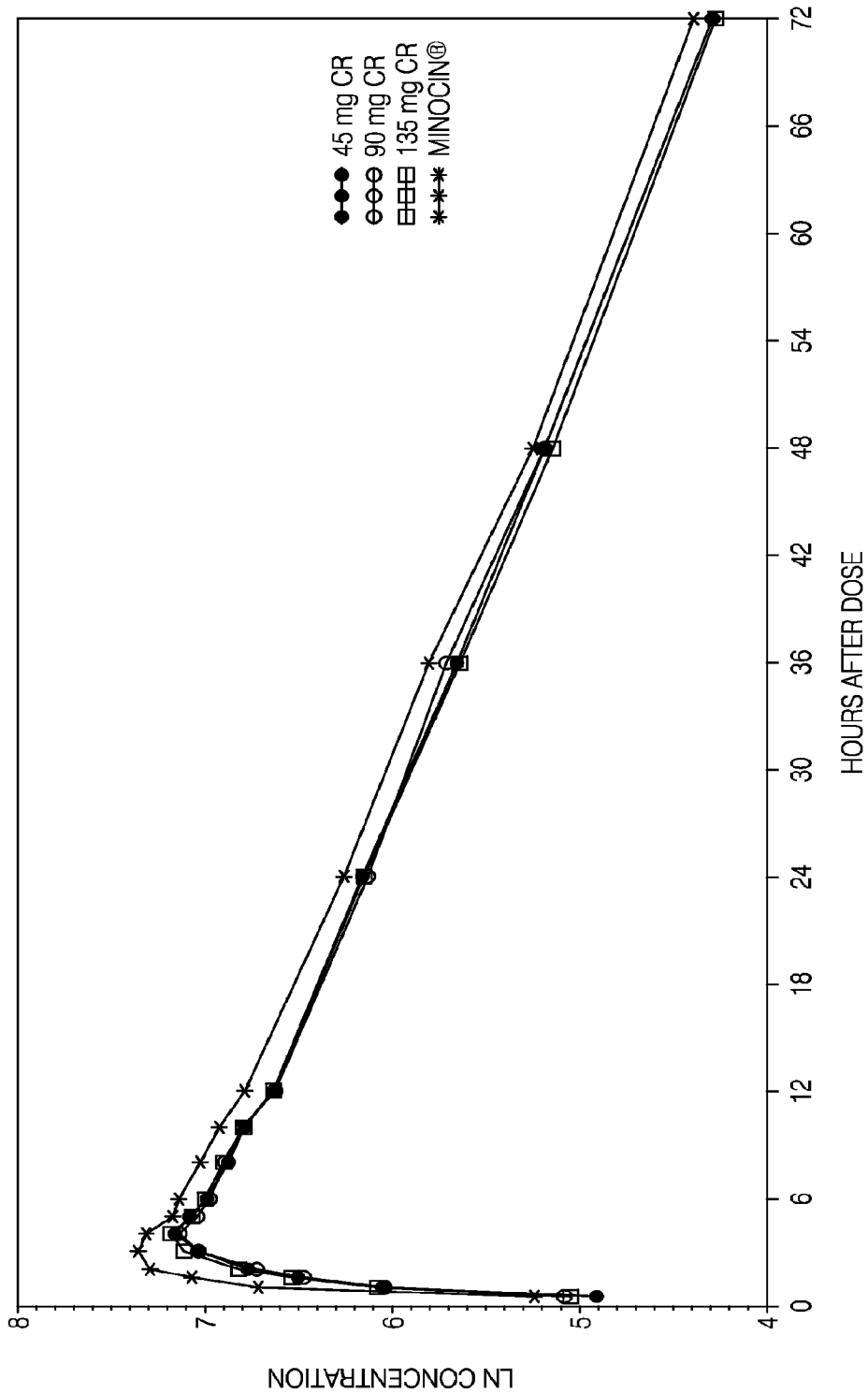
FIG. 2 is a plot showing the logarithm of minocycline plasma concentrations as a function of time across different dosages and formulations.

FIGS. 1-2 show the time dependence of the plasma concentrations.

Each of the three controlled-release caplets produces statistically significantly lower areas and $C_{max}$ than does the MINOCIN® capsule. None of the confidence intervals on the geometric mean $C_{max}$ ratios of the controlled-release compositions to the MINOCIN® capsule are within the bioequivalence acceptable region of 0.80 to 1.25. The mean time of peak ($T_{max}$) of the controlled-release compositions is approximately 1 hour later than the mean for the MINOCIN® capsule, a difference which is detected as statistically significant (p<0.05).

The 90% confidence intervals for the area and $C_{max}$ geometric mean ratios for all possible pair-wise comparisons of the controlled-release caplets are within the bioequivalence acceptance region, 0.80 to 1.25. In addition, the mean time to reach peak concentration for each of the three caplets is essentially the same.

Regarding safety and tolerability, the treatments are well tolerated. The clinical portion of the study is completed per protocol with a total of 19 subjects completing all periods of the study. The rate of absorption from the controlled-release caplets is slower than that of the MINOCIN® capsule.

All three controlled-release caplets are bioequivalent to each other in the dose-adjusted evaluations indicating that the controlled-release caplets have dose-proportional pharmacokinetics.

Example 13

A purpose of this study is to determine the relative bioavailability of minocycline from controlled-release 135 mg minocycline HCl caplets after administration of single doses to normal healthy subjects under fed and fasted conditions. These data are evaluated statistically to determine if the product demonstrates a food effect.

Before entering the study, volunteers undergo a physical examination including clinical laboratory screening and electrocardiogram, to verify inclusion criteria. Subjects are at least 18 years of age, have a body weight within 15% of the appropriate range as defined in the 1983 Metropolitan Life Insurance tables, and weigh at least 110 pounds. A total of 24 non-smoking subjects (12 men and 12 women) are included in this study, of which all 24 finish the study according to the protocol.

The study is performed as a single-dose (one 135 mg CR caplet), two-way crossover study with an adequate washout period (7 days) between the two periods of the study and with an equal number of subjects randomly assigned to receive the study test drug in a fasted state (Treatment A) and after receiving the FDA high-fat Breakfast (Treatment B).

The study conduct is consistent with Good Clinical Practice (GCP) and regulatory requirements of the U.S. Food and Drug Administration. Venous blood samples are collected over a 72-hour period of time post drug administration. Medical care of the volunteers is assured by the presence of a physician for at least 4 hours post dose and the physician is on-call throughout the blood-sampling period. Professional medical personnel are on site during the entire study confinement period. Subjects are confined in the clinical facility for at least 10 hours before dosing and for 24 hours after dosing. Subjects are discharged after the 24-hour blood sample and return as outpatients for the remaining blood samples. Standardized meals are served and no caffeine, alcohol, or grapefruit-containing foods or beverages are allowed to be consumed 24 hours before dosing or throughout study confinement.

All subjects fast for at least 10 hours before dosing. When receiving the fasted dose, subjects continue their fast for an additional 4 hours post drug administration. When receiving the fed dose, subjects are given the FDA high-fat breakfast 30 minutes prior to dosing. From 1 hour before, through 1 hour after dosing, fluid intake is restricted to the water supplied with dosing and the milk supplied with the breakfast. After this time, water is permitted ad lib. Four hours after drug administration, a standardized boxed lunch is served.

The study drugs are administered per randomization code together with 240 ml of tepid water and a mouth check is performed. The time of drug administration is defined as study time=0 in each period. All further study times indicated refer to this time.

No serious adverse events are reported during the entire course of the study. There are eleven (11) adverse events reported including headache (5), dizziness (2), drowsiness (1), syncopy (1), R cheek contusion (1) and lightheadedness (1). A summary of the Adverse Event observed during the study is provided in Table 13.

Blood samples (1×10 ml) are drawn from an antecubital or forearm vein into sodium heparin vacuum tubes and are obtained as shown in Table 14.

TABLE 14

| Day | Procedure | Collection | Time | Hours (relative to dosing) |
|---|---|---|---|---|
| −1 | Confinement | | 1900 | |
| | Snack (provided, not required) | | 2000 | |
| | Fasting Begins | | 2100 | −10 |
| 0 | Vital Signs | | 0530 | |
| | Water restriction begins | | 0600 | |
| | | 1 | 0615 | Pre Dose (0) |
| | Breakfast (Fed treatment only) | | 0630 | −0.5 |
| | Dosing | | 0700 | 0 |
| | | 2 | 0730 | 0.5 |
| | Water restriction ends | 3 | 0800 | 1 |
| | | 4 | 0830 | 1.5 |
| | | 5 | 0900 | 2 |
| | | 6 | 1000 | 3 |
| | Lunch (after sample) | 7 | 1100 | 4 |
| | | 8 | 1200 | 5 |
| | | 9 | 1300 | 6 |
| | | 10 | 1500 | 8 |
| | Dinner (after sample) | 11 | 1700 | 10 |
| | | 12 | 1900 | 12 |
| | Snack | | 2000 | |
| 1 | Discharge | 13 | 0700 | 24 |
| | Safety Labs (P2 only) | | | |
| | Outpatient Return Sample | 14 | 1900 | 36 |
| 2 | Outpatient Return Sample | 15 | 0700 | 48 |
| 3 | Outpatient Return Sample | 16 | 0700 | 72 |

Approximately 320 ml of blood is obtained for the pharmacokinetic samples. Blood samples are centrifuged until separation of red cells from plasma occurs. Plasma is transferred into a polypropylene tube and placed into a freezer within one hour of sample collection. Plasma samples are stored at a temperature at or below −20±5° C. until transferred to the analytical laboratory for analysis.

The study is performed in accordance with the protocol for all essential parts except as outlined below. None of the subjects violate inclusion/exclusion criteria.

TABLE 13

Summary of Adverse Events

| Subj # | Trt (1) | Adverse Event | Sev (2) | Out (3) | Act (4) | Occur (5) | Rel (6) |
|---|---|---|---|---|---|---|---|
| 1 | B | Drowsiness | 1 | 1 | 2 | 2 | 2 |
| 3 | B | Headache | 1 | 1 | 2 | 2 | 2 |
| 4 | A | Dizziness | 1 | 1 | 2 | 2 | 3 |
| 4 | A | Syncopy | 2 | 1 | 2 | 1 | 1 |
| 4 | A | R Cheek Contusion | 1 | 2 | 2, 5 (ice) | 1 | 1 |
| 9 | B | Headache | 2 | 1 | 2, 5 (ice) | 2 | 3 |
| 10 | A | Headache | 1 | 1 | 2 | 2 | 3 |
| 10 | A | Lightheadedness | 1 | 1 | 2 | 2 | 3 |
| 10 | A | Headache | 2 | 2 | 2, 5 (heat) | 1 | 3 |
| 15 | A | Headache | 1 | 1 | 2, 5 (ice) | 2 | 3 |
| 18 | B | Dizziness | 1 | 1 | 2 | 2 | 3 |

(1) Treatment: A = Test, B = Reference, NA = Not applicable (pre-dose)

(2) Severity of Adverse Event: 1-Mild, 2-Moderate, 3-Severe (3) Outcome: 1-Resolved, 2-AE Continuing, 3-Subject Lost to Follow-up, 4-Other (4) Action Taken: 1-None, 2-Increased Surveillance, 3-Medication, 4-Suspend Study Medication, 5-Other (specify)

(5) Occurrence: 1-Intermittent, 2-Continuous (6) Relationship to Drug (Possible Cause): 1-None, 2-Remote, 3-Possible, 4-Probable, 5-Definite There are 5 significant deviations to the blood draw schedule. These are reported to the study Biostatistician.

The sample storage freezer temperature rises beyond −15° C. for short periods of time during the study. These deviations are caused by frequent placement of samples into the freezer or by sample preparation for shipment.

The available data from the 24 subjects who complete the study are used in the pharmacokinetic analyses. Pharmacokinetic procedures and statistical analyses are as described in Example 12.

There are no serious adverse events observed or reported during the study. Clinical laboratory parameters (clinical chemistry and hematology) are obtained at the end of the final period of subject confinement. No clinically significant laboratory abnormalities are observed.

Figure 3:
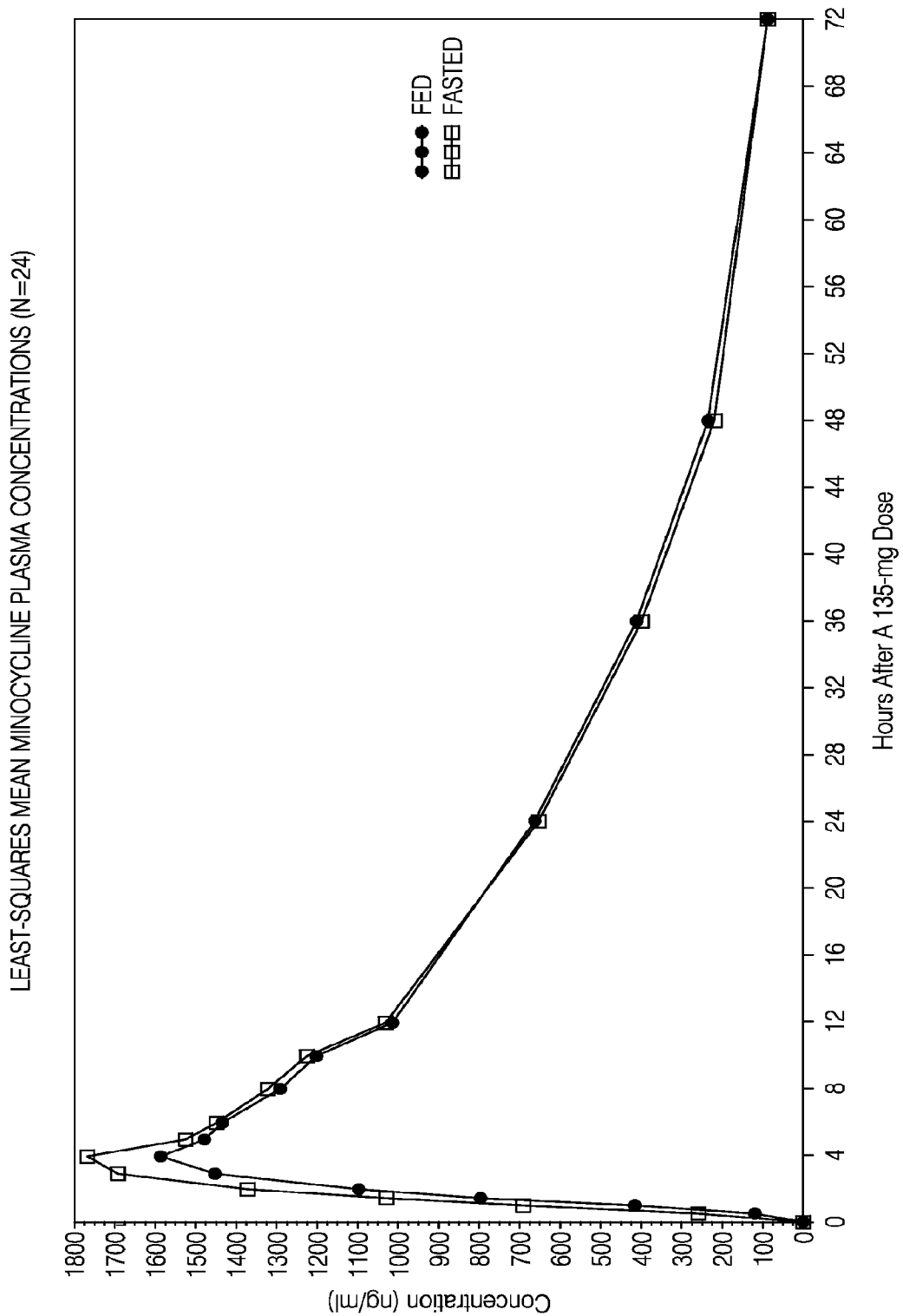
FIG. 3 is a plot showing minocycline plasma concentrations as a function of time for patients under fed and fasted conditions.
Figure 4:
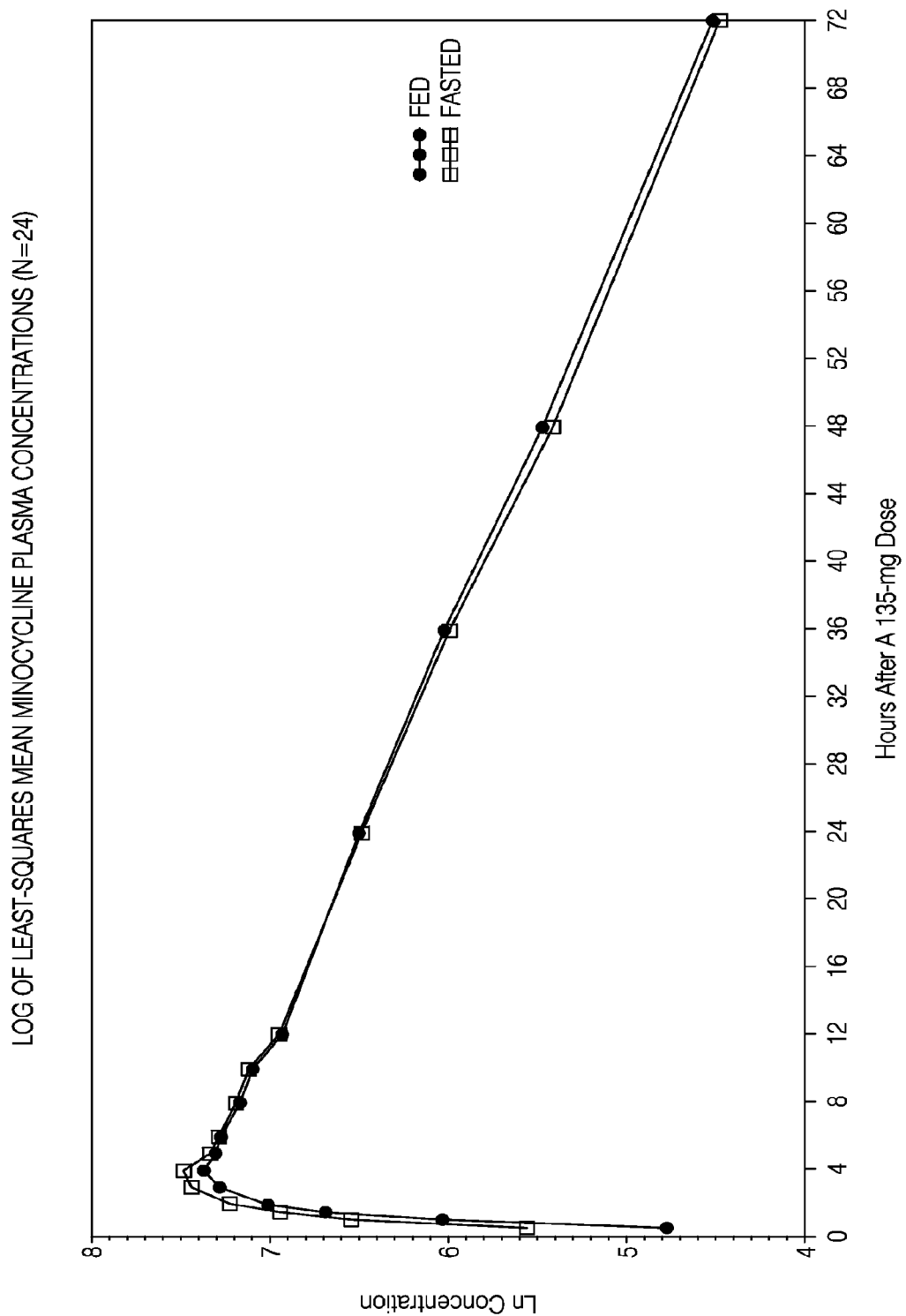
FIG. 4 is a plot showing the logarithm of minocycline plasma concentrations as a function of time for patients under fed and fasted conditions.
Figure 5:
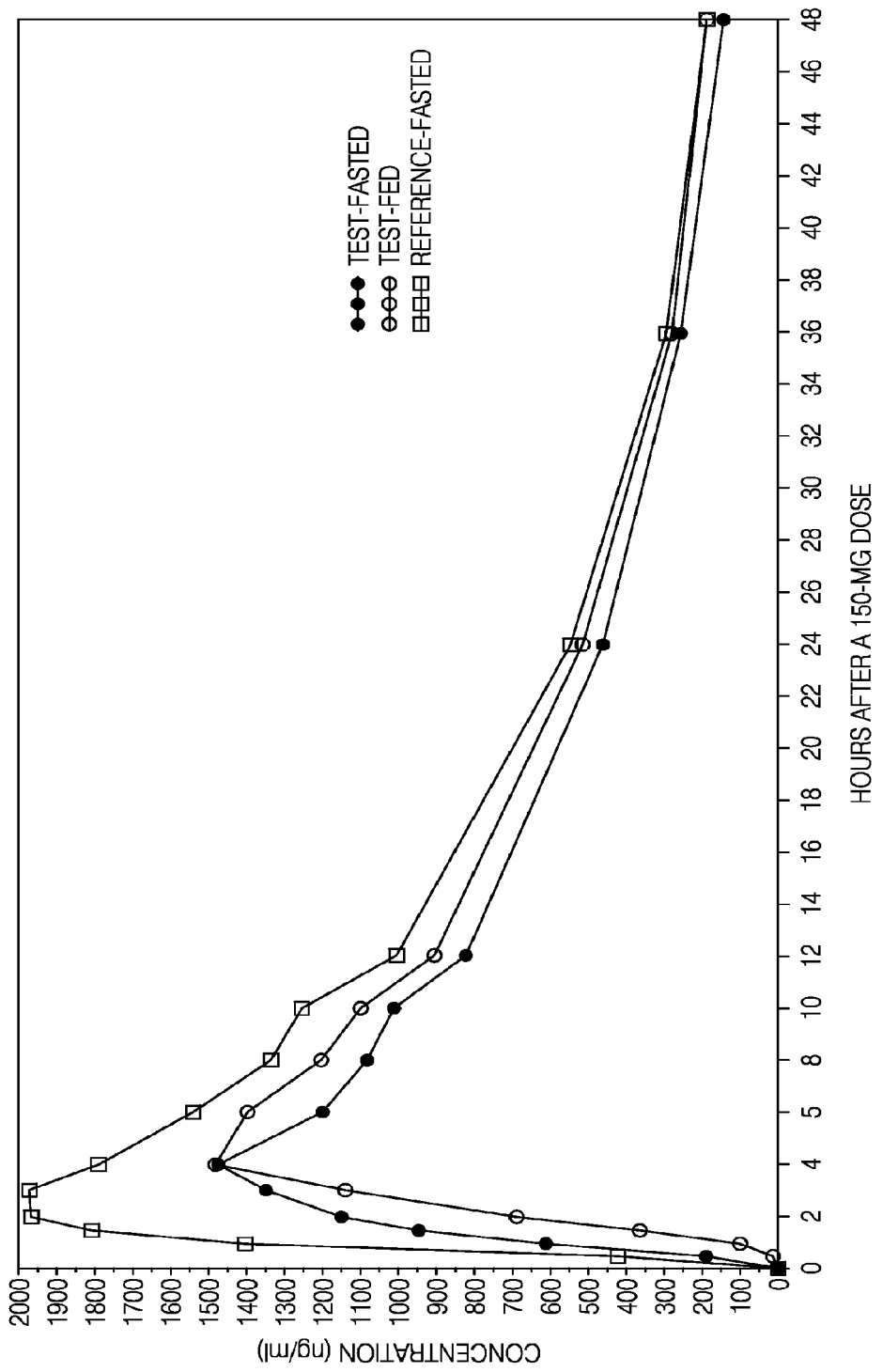
FIG. 5 is a plot showing minocycline plasma concentrations as a function of time across fed and fasted conditions and formulations.
Figure 6:
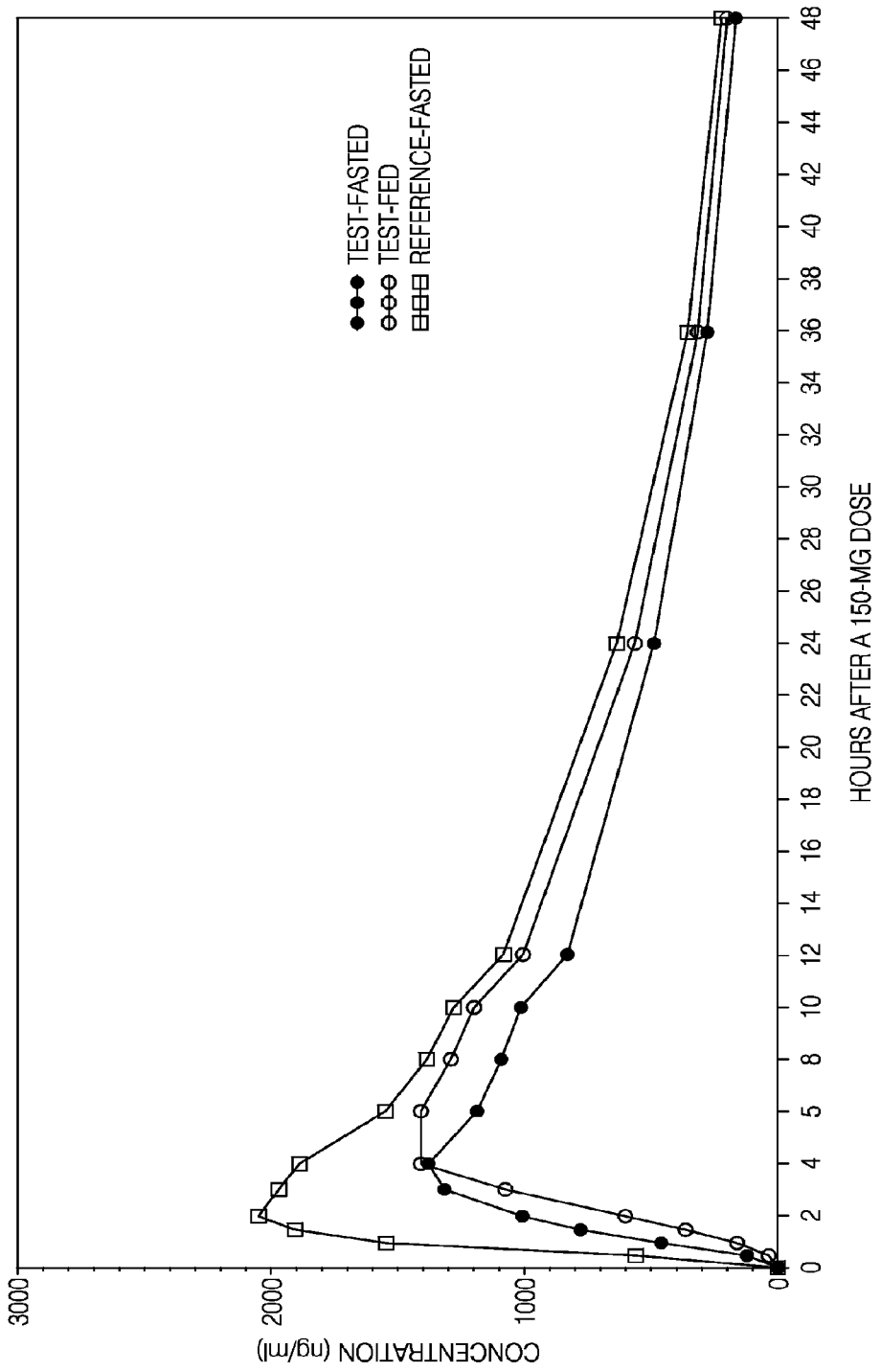
FIG. 6 shows minocycline plasma concentrations as a function of time across fed and fasted conditions and formulations.
Figure 7:
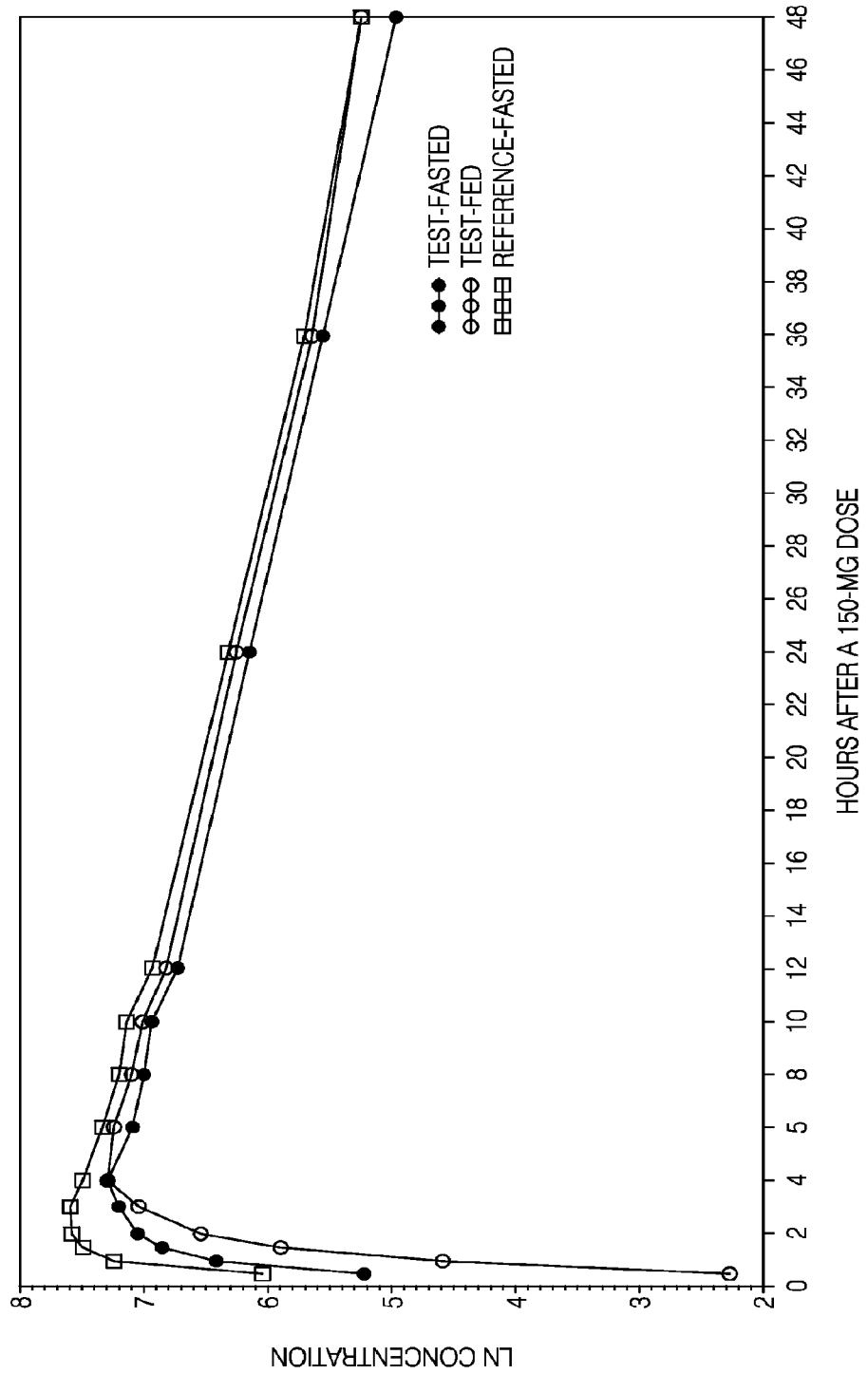
FIG. 7 shows the logarithm of minocycline plasma concentrations as a function of time across fed and fasted conditions and formulations.
Figure 8:
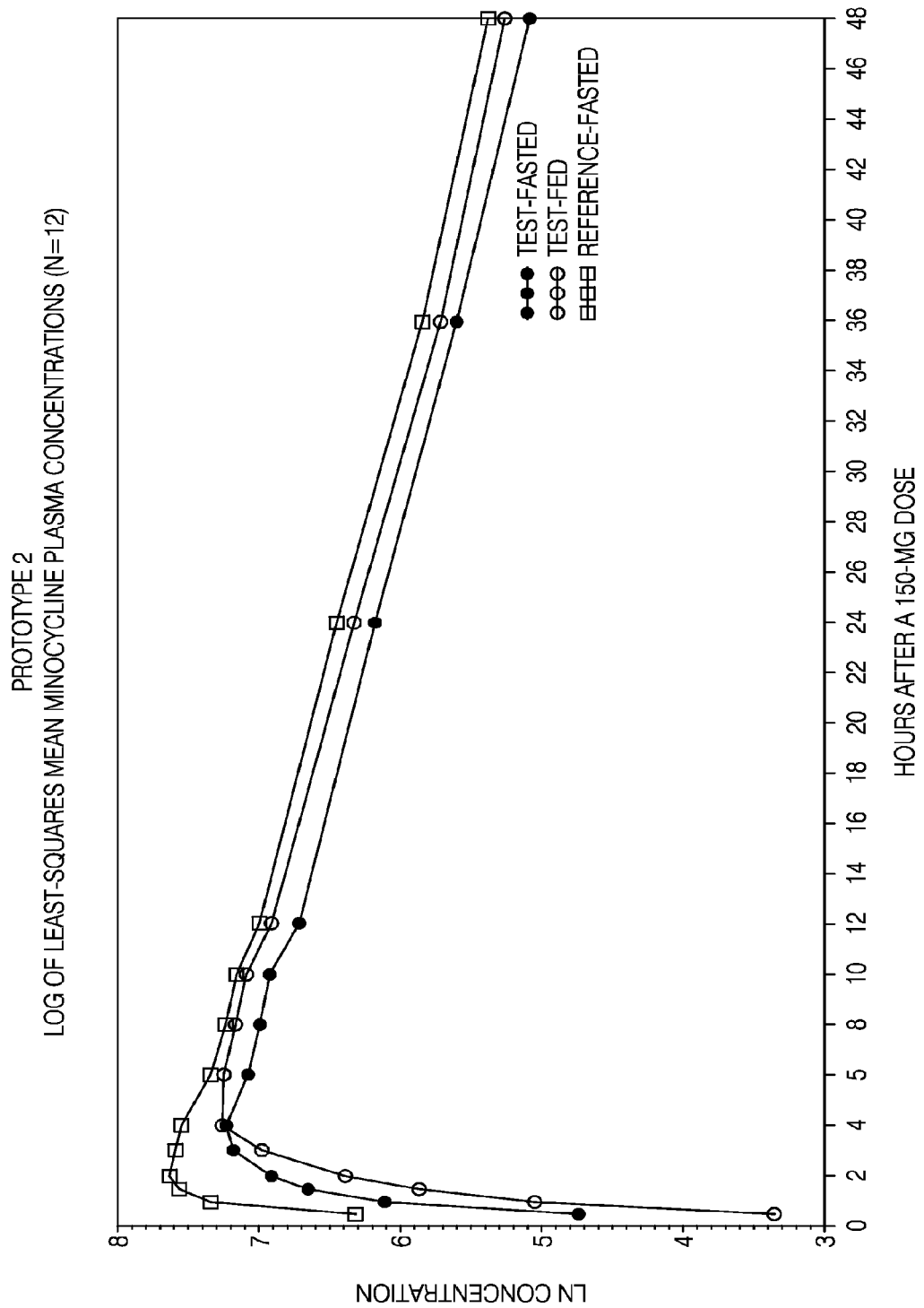
FIG. 8 shows the logarithm of minocycline plasma concentrations as a function of time across fed and fasted conditions and formulations.

Statistical analyses are performed to evaluate the effect of food on the pharmacokinetics of minocycline absorption from controlled-release caplets comprising 135 mg of minocycline. Table 15 summarizes the results of the fed-to-fasted comparisons for the pharmacokinetic parameters. Comparisons of the minocycline levels at each sampling time are summarized in Table 16 and FIGS. 3-4.

TABLE 15

| Parameter | Least-Sequares Means[1] | | Ratio[2] | CV %[3] | 90% Confidence Interval[4] | |
|---|---|---|---|---|---|---|
| | Fed | Fasted | | | Lower | Upper |
| $AUC_{0-t}$ (ng-hr/ml) | 38392 | 39085 | 0.982 | — | 0.895 | 1.070 |
| $AUC_{inf}$ (ng-hr/ml) | 40800 | 41331 | 0.987 | — | 0.900 | 1.074 |
| $C_{max}$ (ng/mL) | 1853 | 1836 | 1.010 | — | 0.893 | 1.126 |
| $T_{max}$ (hour) | 3.52 | 3.69 | 0.955 | — | — | — |
| Ke (1/hour) | 0.0428 | 0.0437 | 0.980 | — | — | — |
| $T^{1/2}$ (hour) | 16.6 | 16.3 | 1.021 | — | — | — |
| Ln-Transformed: | | | | | | |
| $AUC_{0-t}$ (ng-hr/ml) | 36686 | 37781 | 0.971 | 25.2 | 0.858 | 1.098 |
| $AUC_{inf}$ (ng-hr/ml) | 38938 | 39905 | 0.976 | 24.5 | 0.866 | 1.100 |
| $C_{max}$ (ng/ml) | 1775 | 1758 | 1.010 | 28.1 | 0.881 | 1.158 |

[1] Least-squares geometric means for ln-transformed data.
[2] Ratio calculated as the Fed least-squares mean divided by the Fasted least-squares mean. None of the comparisons are detected as statistically significant by ANOVA ($\alpha = 0.05$).
[3] Estimated intra-subject coefficient of variation, CV % = 100 * SQRT($e^{MSE} - 1$), where MSE is the mean square error term from the ANOVA.
[4] Confidence interval on the ratio.

TABLE 16

| Collection (Hour) | Least-Squares Means (ng/ml) | | Significance* (p < 0.05) |
|---|---|---|---|
| | Fed | Fasted | |
| 0.00 | 0.00 | 0.00 | None |
| 0.50 | 118 | 259 | 0.0055 |
| 1.00 | 415 | 693 | 0.0028 |
| 1.50 | 797 | 1029 | None |
| 2.00 | 1100 | 1373 | None |
| 3.00 | 1454 | 1696 | None |
| 4.00 | 1586 | 1771 | None |
| 5.00 | 1479 | 1524 | None |
| 6.00 | 1436 | 1448 | None |
| 8.00 | 1293 | 1319 | None |
| 10.00 | 1204 | 1225 | None |
| 12.0 | 1015 | 1032 | None |
| 24.0 | 659 | 651 | None |
| 36.0 | 410 | 398 | None |
| 48.0 | 235 | 222 | None |
| 72.0 | 91.4 | 87.8 | None |

*Results of the statistical evaluation by ANOVA ($\alpha = 0.05$) for the hypothesis of equal treatment effects. None indicates that no statistically significant difference is detected between treatment means (p > 0.05) at the sampling time evaluated.

Regarding safety and tolerability, the treatments are well tolerated. The clinical portions of the study are completed per protocol with a total of 24 subjects completing all periods of the study.

The 90% confidence intervals for the geometric mean fed-to-fasted area and peak concentration ratios are within the bioequivalence interval 0.80 to 1.25. Food does not appear to affect either the rate or extent of minocycline absorption from the controlled-release minocycline caplets.

Example 14

A purpose of this study is to determine the bioequivalence of Minocycline HCl formulations after administration of single doses to normal healthy males under fed and fasting conditions. These data are evaluated statistically.

Before entering the study, volunteers a physical examination, including clinical laboratory screening and electrocardiogram, to verify inclusion criteria. Prior to study start, volunteers are informed about the aim, design, risks and preparations of the study in writing, and are offered the opportunity to ask any questions. Subjects declare their consent and the voluntary nature of participation by signing an informed consent form. A total of 24 non-smoking male subjects are included in this study, of which 24 finish the study according to the protocol. The mean age is 29.3 years with a range of 19 to 45. The mean height is 70.8 inches and the mean weight is 182.6 pounds.

The study is performed as a single-dose three-way (2×75 mg capsules or 1×150 mg tablet), crossover bioequivalence study with an adequate washout period (7 days) between the three periods of the study.

The study conduct is consistent with Good Clinical Practice (GCP) and regulatory requirements of the U.S. Food and Drug Administration. Venous blood samples are collected over a 48-hour period of time post drug administration. Medical care of the volunteers is assured by the presence of a physician for at least 4 hours post dose and the physician is on-call throughout the blood-sampling period. Professional medical personnel are on site during the entire study confinement period. Subjects are confined in the clinical facility for at least 10 hours before dosing and for 24 hours after dosing. Subjects are discharged after the 24-hour blood sample and returned for outpatient draws at 36, and 48 hours post administration. Standardized meals are served and no caffeine, alcohol, or grapefruit-containing foods or beverages are allowed to be consumed 24 hours before dosing or throughout study confinement.

Treatments A and B provide two prototype versions (Prototype 1 and Prototype 2) of controlled-release minocycline tablets (150 mg). Treatment C provides DYNACIN® immediate-release minocycline tablets (2×75 mg).

The study is performed in a comparative, single dose, three-treatment (Test Fed, Reference Fasted & Test Fasted), three-period, crossover study with an adequate washout period (7 days) between the three phases of the study. Subjects numbered 1-12 received Prototype 1 tablets while subjects 13-24 received Prototype 2 tablets.

All subjects fast for at least 10 hours before dosing. With the exception of consumption of a high fat breakfast (just prior to dosing) during one of the three periods, all subjects remain fasted for 4 hours post drug administration. From 1 hour before, through 1 hour after drug administration, only the water supplied with the drug is permitted. After this time, water is permitted ad lib. Four hours after drug administration, a standardized boxed lunch is served.

The study drugs are administered per randomization code together with 240 ml of tepid water and a mouth check is performed. The time of drug administration is defined as study time=0 in each period. All further study times indicated refer to this time.

No serious adverse events are reported during the entire course of the study. A total of 3 adverse events are reported by 2 subjects, including headache (1) and diarrhea (2). A summary of the adverse events is provided in Table 17.

TABLE 17

Summary of Adverse Events

| Subj # | Trt (1) | Adverse Event | Occur (2) | Sev (3) | Act (4) | Rel (5) | Out (6) |
| --- | --- | --- | --- | --- | --- | --- | --- |
| 1 | A | Headache | 2 | 2 | 2 | 2 | 1 |
| 7 | B | Diarrhea | 1 | 1 | 1 | 3 | 1 |
| 7 | B | Diarrhea | 1 | 1 | 1 | 2 | 1 |

(1) Treatment: A = Test, B = Reference, NA = Not applicable (pre-dose)
(2) Occurrence: 1-Intermittent, 2-Continuous
(3) Severity of Adverse Event: 1-Mild, 2-Moderate, 3-Severe
(4) Action Taken: 1-None, 2-Increased Surveillance, 3-Medication, 4-Suspend Study Medication, 5-Other (specify)
(5) Relationship to Drug (Possible Cause): 1-None, 2-Remote, 3-Possible, 4-Probable, 5-Definite
(6) Outcome: 1-Resolved, 2-AE Continuing, 3-Subject Lost to Follow-up, 4-Other Blood samples (1×10 ml) are drawn from an antecubital or forearm vein into sodium heparin vacuum tubes and are obtained according to Table 18.

TABLE 18

| Day | Procedure | Collection | Time (relative to dosing) | Hours (relative to dosing) |
| --- | --- | --- | --- | --- |
| −1 | Confinement | | 1930 | |
| | Evening Snack | | 2000 | |
| | Fasting Begins | | 2100 | −10 |
| | Water Restriction Begins | | 0600 | |
| 1 | Vital Signs | | 0530-0600 | |
| | Blood Draw | 1 | 0630 | Pre Dose (0) |
| | Breakfast (where applicable) | | 0645 | −0.25 |
| | Dosing | | 0700 | 0 |
| | Blood Draw | 2 | 0730 | 0.50 |
| | Water Restriction Ends (After Blood Draw) | 3 | 0800 | 1.0 |
| | Blood Draw | 4 | 0830 | 1.5 |
| | Blood Draw | 5 | 0900 | 2.0 |
| | Blood Draw | 6 | 1000 | 3.0 |
| | Lunch (After Blood Draw) | 7 | 1100 | 4.0 |
| | Blood Draw | 8 | 1300 | 6.0 |
| | Blood Draw | 9 | 1500 | 8.0 |
| | Blood Draw | 10 | 1700 | 10.0 |
| | Dinner | | 1800 | |
| | Blood Draw | 11 | 1900 | 12.0 |
| | Evening Snack | | 2100 | |
| 2 | Discharge (After Blood Draw) | 12 | 0700 | 24.0 |
| | Outpatient Blood Draw | 13 | 1900 | 36.0 |
| 3 | Outpatient Blood Draw | 14 | 0700 | 48.0 |

Approximately 420 ml of blood is obtained for the pharmacokinetic samples. Blood samples are centrifuged until separation of red cells from plasma occurs. Plasma is transferred split into a polypropylene tube and placed into a freezer within one hour of sample collection. Plasma samples are stored at a temperature at or below −20°±5° C. until transferred to the analytical laboratory for analysis.

Sample analyses are performed as described in Example 12.

The available data from the 24 subjects who completed all three periods of the study are used in the pharmacokinetic analyses. Pharmacokinetic calculations are performed using SAS (PC version 6.12). Any sample concentration reported less than the assay limit of quantitation is set to zero for use in the pharmacokinetic and statistical analyses.

Pharmacokinetic parameters (areas, times to peak and elimination rates) are calculated using the actual rather than the scheduled times of sample collection. Graphical presentations of individual subject results also use the exact times of sample collection. Graphical presentations of mean results use the scheduled times of sample collection.

Peak concentration ($C_{max}$) is the observed maximum value during the collection period of 0 to 48 hours. The time to peak concentration ($T_{max}$) is the time at which $C_{max}$ is observed (or first observed, if the peak value occurs at more than one time).

The apparent first-order elimination rate constant (Ke) is estimated as the negative value of the slope of the regression line for the terminal log-linear concentration-time values. A minimum of six terminal values is used to obtain an estimate. The values included in the regression analyses are determined by examination of the individual subject plots of natural logarithm of concentration against time. Elimination half-life (T½) is estimated as $\log_e(2)/Ke$.

Area under the curve ($AUC_{0-t}$) to the last measured concentration ($C_t$) is calculated by the linear trapezoidal method. Area to infinite time ($AUC_{inf}$) is calculated by extrapolating $AUC_{0-t}$ by the addition of the quantity: $C_t/Ke$.

Statistical analyses are performed using the General Linear Models (GLM) procedure of the SAS statistical program (PC version 6.12). The pharmacokinetic parameter estimates, as well as the concentrations at each scheduled sample time are evaluated by analysis of variance. Hypothesis testing for treatment effects in the analysis are conducted at $\alpha=0.05$.

The statistical model contains main effects of sequence, subject nested within sequence treatment, and period. F-ratios for testing main effects are constructed using the mean square error term for the effect as the numerator and the mean square error term from the ANOVA as the denominator. The F-ratio to test for sequence effects is constructed using the type III mean square term for sequence as the numerator and type III mean square for subjects nested within sequence as the denominator.

When statistically significant differences are detected (p<0.05), pairwise comparisons of treatment means are conducted to determine if the significance could be attributed to the difference between one or more pairs of treatment means. These pairwise comparisons are performed at an adjusted $\alpha=0.017$ level to maintain the overall experimental error rate at 0.05.

Pairwise comparisons of interest are controlled-release minocycline 150 mg tablets (Test Fasted) vs. DYNACIN® 75 mg capsules (Reference Fasted) for determining bioequivalence and Test Fed vs. Test Fasted for assessing the effects of food on the generic product. These comparisons are conducted on the 12 subjects (subjects 1-12) who are randomized with Prototype 1 (Test) of minocycline and also on the 12 subjects (subjects 13-24) who are randomized with Prototype 2 (Test).

Power for the pair-wise pharmacokinetic comparisons is calculated as the probability ($\alpha=0.05$) of detecting a difference equal to 20% of the mean for the reference treatment in the comparison (or a test-to-reference ratio of 1.25 for log-transformed results). (Winer, B J. Statistical Principles in Experimental Design. New York: McGraw-Hill Book Company (1962) 21-26.)

Confidence Intervals (90%) for the area and peak concentration comparisons are calculated by the t-test approach (2, 1-sided) at $\alpha=0.10$ overall, $\alpha=0.05$ each side:

$$\text{Interval Lower Limit} = (X_T - X_R) - Se \cdot t_{\alpha/2}$$

$$\text{Interval Upper Limit} = (X_T - X_R) + Se \cdot t_{\alpha/2}$$

Where $X_T$, $X_R$ are the Test-Fasted and Reference-Fasted (Test-Fed and Test-Fasted for food-effect comparison) least-squares means, respectively.

Se is the standard error of the estimated difference between means from the SAS estimate statement.

$t_{\alpha/2}$ is the critical value from the t-distribution with degrees of freedom that of the error term and $\alpha=0.10$.

For log-transformed data the interval is calculated from the ANOVA results on the transformed values and then exponentiated to convert to the non-transformed scale:

$$\text{Interval Limit} = e^{(\text{log-transformed interval limit})}$$

The intervals are computed for the "true" mean treatment differences, expressed as a percent of the reference mean, and true geometric mean ratios (from logarithmic transformation).

There are no serious adverse events observed or reported during the study. Clinical laboratory parameters (clinical chemistry and hematology) are obtained at the end of the final period of subject confinement. No clinically significant laboratory abnormalities are observed.

Statistical analyses are performed on the results in order to compare controlled-release Prototype 1 minocycline 150 mg tablets to DYNACIN® 75 mg capsules and controlled-release Prototype 2 minocycline 150 mg tablets to DYNACIN® 75 mg capsules when each is administered as a single 150 mg dose immediately after an overnight fast. Tables 19-22 summarize the results of the statistical analyses of the major pharmacokinetic parameters. Tables 23-24 and FIGS. 5-8 summarize the comparisons of the concentrations at each sampling time.

TABLE 19

| | Prototype 1 | | | | | |
|---|---|---|---|---|---|---|
| | Least-Squares Means[1] | | | | 90% Confidence Interval[4] | |
| | Test | Reference | | | | |
| Parameter | Fasted | Fasted | Ratio[2] | Power[3] | Lower | Upper |
| $AUC_{0-t}$ (ng-hr/ml) | 27007 | 34303 | 0.787* | 0.98 | 0.705 | 0.870 |
| $AUC_{inf}$ (ng-hr/ml) | 29766 | 38005 | 0.783* | 0.97 | 0.697 | 0.870 |
| $C_{max}$ (ng/ml) | 1523 | 2091 | 0.728* | 0.97 | 0.643 | 0.814 |
| $T_{max}$ (hour) | 3.58 | 2.25 | 1.590* | 0.20 | — | — |
| Ke (1/hour) | 0.0518 | 0.0523 | 0.992 | >0.99 | — | — |
| T½ (hour) | 13.54 | 13.53 | 1.001 | >0.99 | — | — |

TABLE 19-continued

Prototype 1

| | Least-Squares Means[1] | | | | 90% Confidence Interval[4] | |
|---|---|---|---|---|---|---|
| Parameter | Test Fasted | Reference Fasted | Ratio[2] | Power[3] | Lower | Upper |
| | Ln-Transformed: | | | | | |
| AUC$_{0-t}$ (ng-hr/ml) | 26221 | 33677 | 0.779* | 0.95 | 0.704 | 0.861 |
| AUC$_{inf}$ (ng-hr/ml) | 28911 | 37334 | 0.774* | 0.95 | 0.699 | 0.858 |
| C$_{max}$ (ng/ml) | 1480 | 2030 | 0.729* | 0.98 | 0.665 | 0.798 |

[1]Least-squares geometric means for ln-transformed data.
[2]Ratio calculated as Test-Fasted least-squares mean divided by Reference-Fasted least-squares mean.
[3]Power to detect a difference of 20% of the Reference mean or a ratio of 1.25 (ln-transformed results).
[4]Confidence interval on the ratio.
*Comparison is detected as statistically significant by ANOVA (α = 0.05).

TABLE 20

Prototype 1

| | Least-Squares Means[1] | | | | 90% Confidence Interval[4] | |
|---|---|---|---|---|---|---|
| Parameter | Test Fed | Test Fasted | Ratio[2] | Power[3] | Lower | Upper |
| AUC$_{0-t}$ (ng-hr/ml) | 28312 | 27007 | 1.048 | 0.88 | 0.943 | 1.153 |
| AUC$_{inf}$ (ng-hr/ml) | 32207 | 29766 | 1.082 | 0.84 | 0.972 | 1.192 |
| C$_{max}$ (ng/ml) | 1706 | 1523 | 1.120 | 0.80 | 1.002 | 1.238 |
| T$_{max}$ (hour) | 4.00 | 3.58 | 1.116 | 0.43 | — | — |
| Ke (1/hour) | 0.0497 | 0.0518 | 0.958 | >0.99 | — | — |
| T½ (hour) | 14.24 | 13.54 | 1.052 | >0.99 | — | — |
| | Ln-Transformed: | | | | | |
| AUC$_{0-t}$ (ng-hr/ml) | 27577 | 26221 | 1.052 | 0.95 | 0.951 | 1.163 |
| AUC$_{inf}$ (ng-hr/ml) | 31279 | 28911 | 1.082 | 0.95 | 0.976 | 1.199 |
| C$_{max}$ (ng/ml) | 1644 | 1480 | 1.111 | 0.98 | 1.014 | 1.217 |

[1]Least-squares geometric means for ln-transformed data.
[2]Ratio calculated as Test-Fed least-squares mean divided by Test-Fasted least-squares mean.
[3]Power to detect a difference of 20% of the Test-Fasted mean or a ratio of 1.25 (ln-transformed results).
[4]Confidence interval on the ratio.

TABLE 21

Prototype 2

| | Least-Squares Means[1] | | | | 90% Confidence Interval[4] | |
|---|---|---|---|---|---|---|
| Parameter | Test Fasted | Reference Fasted | Ratio[2] | Power[3] | Lower | Upper |
| AUC$_{0-t}$ (ng-hr/ml) | 26984 | 37130 | 0.727* | >0.99 | 0.671 | 0.783 |
| AUC$_{inf}$ (ng-hr/ml) | 30617 | 41776 | 0.733* | >0.99 | 0.671 | 0.795 |
| C$_{max}$ (ng/ml) | 1402 | 2169 | 0.646* | >0.99 | 0.578 | 0.715 |
| T$_{max}$ (hour) | 3.58 | 2.25 | 1.593* | 0.25 | — | — |
| Ke (1/hour) | 0.0513 | 0.0504 | 1.016 | >0.99 | — | — |
| T½ (hour) | 14.26 | 14.17 | 1.007 | >0.99 | — | — |
| | Ln-Transformed: | | | | | |
| AUC$_{0-t}$ (ng-hr/ml) | 25952 | 36471 | 0.712* | >0.99 | 0.657 | 0.771 |
| AUC$_{inf}$ (ng-hr/ml) | 29144 | 40807 | 0.714* | 0.99 | 0.657 | 0.777 |
| C$_{max}$ (ng/ml) | 1358 | 2142 | 0.634* | 0.95 | 0.573 | 0.701 |

[1]Least-squares geometric means for ln-transformed data.
[2]Ratio calculated as Test-Fasted least-squares mean divided by Reference-Fasted least-squares mean.
[3]Power to detect a difference of 20% of the Reference mean or a ratio of 1.25 (ln-transformed results).
[4]Confidence interval on the ratio.
*Comparison is detected as statistically significant by ANOVA (α = 0.05).

TABLE 22

Prototype 2

| | Least-Squares Means[1] | | | | 90% Confidence Interval[4] | |
|---|---|---|---|---|---|---|
| Parameter | Test Fed | Test Fasted | Ratio[2] | Power[3] | Lower | Upper |
| AUC$_{0-t}$ (ng-hr/ml) | 30062 | 26984 | 1.114 | 0.99 | 1.037 | 1.191 |
| AUC$_{inf}$ (ng-hr/ml) | 34228 | 30617 | 1.118 | 0.97 | 1.033 | 1.203 |
| C$_{max}$ (ng/ml) | 1670 | 1402 | 1.191* | 0.87 | 1.085 | 1.297 |
| T$_{max}$ (hour) | 4.42 | 3.58 | 1.233 | 0.52 | — | — |
| Ke (1/hour) | 0.0507 | 0.0513 | 0.990 | >0.99 | — | — |

TABLE 22-continued

Prototype 2

| Parameter | Least-Squares Means[1] | | Ratio[2] | Power[3] | 90% Confidence Interval[4] | |
|---|---|---|---|---|---|---|
| | Test Fed | Test Fasted | | | Lower | Upper |
| T½ (hour) | 14.21 | 14.26 | 0.997 | >0.99 | — | — |
| Ln-Transformed: | | | | | | |
| $AUC_{0-t}$ (ng-hr/ml) | 29591 | 25952 | 1.140* | >0.99 | 1.053 | 1.235 |
| $AUC_{inf}$ (ng-hr/ml) | 33493 | 29144 | 1.149* | 0.99 | 1.057 | 1.250 |
| $C_{max}$ (ng/ml) | 1650 | 1358 | 1.215* | 0.95 | 1.099 | 1.344 |

[1]Least-squares geometric means for ln-transformed data.
[2]Ratio calculated as Test-Fed least-squares mean divided by Test-Fasted least-squares mean.
[3]Power to detect a difference of 20% of the Test-Fasted mean or a ratio of 1.25 (ln-transformed results).
[4]Confidence interval on the ratio.
*Comparison is detected as statistically significant by ANOVA ($\alpha = 0.05$).

TABLE 23

Prototype 1
Least-Squares Means (ng/ml)

| Collection (Hour) | Test Fasted (A) | Test Fed (B) | Reference Fasted (C) | Significance (p < 0.05) |
|---|---|---|---|---|
| 0.00 | 0.00 | 0.00 | 0.00 | None |
| 0.50 | 188 | 9.60 | 419 | C > B |
| 1.00 | 613 | 100 | 1405 | C > A > B |
| 1.50 | 946 | 362 | 1807 | C > A > B |
| 2.00 | 1153 | 690 | 1967 | C > A > B |
| 3.00 | 1349 | 1143 | 1972 | C > A, B |
| 4.00 | 1472 | 1478 | 1788 | C > A, B |
| 6.00 | 1200 | 1396 | 1540 | C > A |
| 8.00 | 1082 | 1203 | 1334 | C > A |
| 10.0 | 1012 | 1097 | 1253 | C > A |
| 12.0 | 820 | 901 | 1002 | C > A |
| 24.0 | 457 | 510 | 540 | None |
| 36.0 | 253 | 274 | 292 | None |
| 48.0 | 140 | 182 | 185 | A < B, C |

* Results of the statistical evaluation by ANOVA ($\alpha = 0.05$) for the hypothesis of equal treatment effects. When significance is detected (p < 0.05), pairwise comparisons are performed to determine if the significance could be attributed to differences between any two treatment means.
C > A, B indicates that the Reference-Fasted mean is statistically significantly different from both the Test-Fasted and Test-Fed means.
None indicates that no difference is detected between treatment means (p > 0.05) at the sampling time evaluated.

TABLE 24

Prototype 2
Least-Squares Means (ng/ml)

| Collection (Hour) | Test Fasted (A) | Test Fed (B) | Reference Fasted (C) | Significance (p < 0.05) |
|---|---|---|---|---|
| 0.00 | 0.00 | 0.00 | 0.00 | None |
| 0.50 | 115 | 28.7 | 553 | C > A, B |
| 1.00 | 453 | 156 | 1542 | C > A > B |
| 1.50 | 772 | 356 | 1906 | C > A > B |
| 2.00 | 1002 | 595 | 2040 | C > A > B |
| 3.00 | 1308 | 1070 | 1966 | C > A, B |
| 4.00 | 1374 | 1409 | 1885 | C > A, B |
| 6.00 | 1181 | 1405 | 1544 | A < B, C |
| 8.00 | 1084 | 1285 | 1381 | A < B, C |
| 10.0 | 1007 | 1191 | 1274 | A < B, C |
| 12.0 | 820 | 999 | 1075 | A < B, C |
| 24.0 | 478 | 554 | 624 | C > B > A |
| 36.0 | 269 | 301 | 342 | C > A |
| 48.0 | 158 | 189 | 215 | C > A |

* Results of the statistical evaluation by ANOVA ($\alpha = 0.05$) for the hypothesis of equal treatment effects. When significance is detected (p < 0.05), pairwise comparisons are performed to determine if the significance could be attributed to differences between any two treatment means.
C > A, B indicates that the Reference-Fasted mean is statistically significantly different from both the Test-Fasted and Test-Fed means.
None indicates that no difference is detected between treatment means (p > 0.05) at the sampling time evaluated.

Prototype 1 has a statistically significantly (p<0.05) lower extent of absorption than the DYNACIN® product. The mean test-to-reference area ratios are less than 0.78 and mean peak concentration ratio is 0.73. The time to peak for Prototype 1 is statistically significantly longer than that for the Reference product (3.58 hours compared to 2.25 hours). Food increases both the area and $C_{max}$ for Prototype 1 and slightly delays the time to peak. However, the differences between dosing Prototype 1 with or without food are not detected as statistically significant (p<0.05).

Prototype 2 has a statistically significantly (p<0.05) lower extent of absorption than the DYNACIN® product. The mean test-to-reference area ratios are less than 0.72 and peak concentration ratio is 0.63. The time to peak for Prototype 2 is statistically significantly longer than that for the Reference product (3.58 hours compared to 2.25 hours). Food increases the extent (area ratios greater than 1.14) and delays the rate ($T_{max}$ ratio 1.23) of absorption from Prototype 2. The differences between the fed and fasted results are statistically significant (p<0.05).

Regarding safety and tolerability, the treatments are reasonably well tolerated. The clinical portion of the study is completed per protocol with a total of 24 subjects completing all periods of the study.

Example 15

A purpose of this study is to determine the pharmacokinetics of two minocycline formulations after administration of multiple doses to normal, healthy subjects. These data are evaluated statistically to determine the relative bioavailability at steady state between Controlled-Release (CR) Minocycline HCl Caplets and commercially available MINOCIN® (minocycline HCl) Capsules.

The study is a randomized 2-way crossover study in 28 healthy males and females to evaluate the pharmacokinetics of minocycline during 6 days of once daily treatment with Controlled-Release Minocycline HCl Caplets, 135 mg (Test product). The reference product is commercially available MINOCIN® (minocycline HCl) Capsules, 100 mg (Lederle) administered every 12 hours for 6 days. Each dose is taken at approximately the same time each day with or without food, except for the morning dose on Day 6 of each period which is taken in a fasting state. Subjects self-administer the medication on an outpatient basis for the afternoon capsule doses on Day 1 and Day 4, and for all doses on Days 2 and 3. On all other days subjects are dosed at the clinic in conjunction with other study-related activities.

Each subject receives treatment with either the Test or the Reference products in each of the 2 study periods, in randomized sequence. The first dose of the second period is administered 20 days after the first dose of Period 1. Blood samples for minocycline analysis are drawn pre-dose on Day 1, Day 4, and Day 5 of each period. Sampling on Day 6 is pre-dose and at 0.5, 1.0, 1.5, 2.0, 3.0, 4.0, 5.0, 6.0, 8.0, 12.0, 12.5, 13.0, 13.5, 14.0, 15.0, 16.0, 17.0, 18.0 and 20.0 hours post-dose. On Day 7, subjects are discharged from the research facility after a 24-hour post-dose sample is obtained. Subjects return to the clinic each morning on Days 8 and 9 (at 48 and 72 hours postdose, respectively) for additional sampling.

The total duration of the study for each participant is approximately 30 days, including the washout period. Plasma concentrations are determined by a validated and sensitive bioanalytical method. The analytical data are utilized to compare the formulations in regard to plasma concentrations at each collection, $C_{max}$, $T_{max}$, and AUC for each dose.

The study design follows standard methodology for the determination of steady state pharmacokinetic (PK) parameters. It is estimated that 6 days of the dosing regimen is sufficient to attain steady state plasma minocycline levels, consistent with the PK principle of dosing over 5 half-lives to reach steady-state blood levels.

Subjects are recruited from a population of healthy male and female adults. Good physical health is determined by medical history, physical examination, including electrocardiogram (ECG), and clinical laboratory tests, conducted within 2 weeks of study dosing.

Subjects are assigned upon enrollment to a sequence of treatments according to a predetermined randomization schedule. A subject could either receive once daily Controlled-Release Minocycline HCl Caplets, 135 mg, in Period 1 and twice daily MINOCIN® (minocycline HCl) Capsules, 100 mg, in Period 2 (sequence=QB); or twice daily MINOCIN® (minocycline HCl) Capsules, 100 mg, in Period 1 and once daily Controlled-Release Minocycline HCl Caplets, 135 mg, in Period 2 (sequence=BQ).

Neither the subjects nor the clinical site personnel are blinded to the identities of the study medications. However, samples are shipped to the analytical laboratory without identification of the treatments, so the analysis of plasma minocycline concentrations and the data management are performed in a blinded manner.

The study drugs are administered by trained clinical personnel on the mornings of Day 1, Day 4, Day 5, and Day 6, and on the evenings of Day 5 and Day 6. All other doses are self-administered by the subjects at home. The drug is administered orally with 240 mL of tepid water. On Day 6, the subjects fast from 10 hours prior to the morning dose until 4 hours post-dose. Subjects are confined to the clinical site in each period from the evening before Day 1 until after the Day 1 morning dose, and from the evening of Day 5 until 24 hours after the morning dose of Day 6.

All medications taken during the study are recorded on the Concomitant Medication page of the CRF. No caffeine, alcohol, grapefruit, or xanthine-containing food or drinks are permitted during the treatment periods.

Hand and mouth checks are performed for all supervised doses to ensure dosing compliance.

A summary of the visit schedule and assessments is presented in Table 25.

TABLE 25

| | Screening | Period 1 | | | | | | | | | Washout | Period 2 | | | | | | | | |
|---|---|---|---|---|---|---|---|---|---|---|---|---|---|---|---|---|---|---|---|---|
| Study Day | −14 to −1 | 1 | 2 | 3 | 4 | 5 | 6 | 7 | 8 | 9 | 10-20 | 21 | 22 | 23 | 24 | 25 | 26 | 27 | 28 | 29 |
| Informed consent | X | | | | | | | | | | | | | | | | | | | |
| Demographics* | X | | | | | | | | | | | | | | | | | | | |
| Medical History | X | | | | | | | | | | | | | | | | | | | |
| Physical Exam[H] | X | | | | | | | | | | | | | | | | | | | |
| Vital Signs | X | X | | | | | X | | | | | X | | | | | X | | | | |
| Serum Chemistry and Hematology[I] | X | | | | | | | | | | | | | | | | | | | X | |
| Urinalysis[§] | X | | | | | | | | | | | | | | | | | | | | |
| Urine Drug Screen[II] | X | X | | | | | | | | | | X | | | | | | | | | |
| Pregnancy Test | X | X | | | | | | | | | | X | | | | | | | | | |
| Adverse Events | | | | | X | X | X | X | X | X | | X | | | X | X | X | X | X | X | |
| Plasma Collection | | X | | | X | X | X[¶] | X | X | X | | X | | | X | X | X[¶] | X | X | X | |
| Dosing at Clinic | | X | | | X | X | X | | | | | X | | | X | X | X | | | | |
| Self-Dose[#] | | X | X | X | X | | | | | | | X | X | X | X | | | | | | |
| Dispense Study Drug | | X | | | | | | | | | | X | | | | | | | | | |
| Collect/Reconcile Study Drug | | | | | | | X | | | | | | | | | | X | | | | |
| Dispense Diaries | | X | | | | | | | | | | X | | | | | | | | | |
| Collect Diaries | | | | | | | X | | | | | | | | | | X | | | | |

*Includes sex, age, race, body weight, height, body build, and tobacco use.
[H]Including ECG.
[I]Complete blood counts (CBC), serum electrolytes, glucose, creatinine, blood urea nitrogen (BUN), liver function tests (alanine aminotransferase [ALT], aspartate aminotransferase (AST), alkaline phosphatase, and bilirubin).
[§]Dipstick with microscopic examination if indicated.
2 Negative for drugs of abuse at Screening and as a safety assessment at check-in each period by rapid qualitative screening test device.
[¶]Blood draws on Day 6 occur pre-dose, 0.5, 1.0, 1.5, 2.0, 3.0, 4.0, 5.0, 6.0, 8.0, 12.0, 12.5, 13.0, 13.5, 14.0, 15.0, 16.0, 17.0, 18.0, and 20.0 hours post-dose.
[#]For subjects receiving MINOCIN ® capsules, the evening doses on Days 1 and 4 of each period are self-administered.

A listing of adverse events reported in this study is summarized and provided by system organ class and MedDRA term in Tables 26-29.

Ten subjects (35.7%) report at least one AE while treated with the Test product; 12 subjects (44.4%) report at least one AE while treated with the Reference product. No subjects report a severe AE; there are no serious AEs, and no subject discontinues treatment due to an AE.

The most common AEs with the Test product are headache (25.0%), fatigue (17.9%), somnolence (14.3%), dizziness (7.1%), and nausea (7.1%). The most common AEs reported by subjects under treatment with the Reference drug are headache (33.3%), dizziness (22.2%), fatigue (7.4%), and nausea (7.4%).

TABLE 26

Summary of Incidence of Adverse Events
All Subjects (N = 28)

|  | Test (CR) | Reference |
|---|---|---|
| Subjects Treated | 28 | 27 |
| Subjects with AE | 10 (35.7%) | 12 (44.4%) |
| Subjects with treatment-related AE | 5 (17.9%) | 9 (33.3%) |
| Subjects with severe AE | 0 | 0 |
| Subjects discontinued due to AE | 0 | 0 |
| Subjects with serious AE | 0 | 0 |
| Adverse events reported by more than 1 subject for either treatment |  |  |
| Headache | 7 (25.0%) | 6 (22.2%) |
| Fatigue | 5 (17.9%) | 2 (7.4%) |
| Somnolence | 4 (14.3%) | 0 |
| Dizziness | 2 (7.1%) | 6 (22.2%) |
| Nausea | 2 (7.1%) | 2 (7.4%) |

TABLE 27

|  | 100 mg MINOCIN ® Capsules | Controlled-Release Caplet |
|---|---|---|
| Number of subjects treated | 27 | 28 |
| Number of subjects with at least 1 event | 12 (44.4%) | 10 (35.7%) |
| Number of events | 36 | 39 |
| Number of subjects with at least 1 serious adverse event | 0 (0.0%) | 0 (0.0%) |
| Number of subjects with at least 1 treatment related adverse event | 9 (33.3%) | 5 (17.9%) |
| Number of subjects with at least 1 severe adverse event | 0 (0.0%) | 0 (0.0%) |
| Number of subjects discontinued due to adverse event | 0 (0.0%) | 0 (0.0%) |
| Nervous System Disorders | 11 (40.7%) | 9 (32.1%) |
| Headache | 5 (22.2%) | 7 (25.0%) |
| Dizziness | 6 (22.2%) | 2 (7.1%) |
| Somnolence | 0 (0.0%) | 4 (14.3%) |
| Photophobia | 0 (0.0%) | 1 (3.6%) |
| General Disorders & Site Conditions | 3 (11.1%) | 6 (21.4%) |
| Fatigue | 2 (7.4%) | 5 (17.9%) |
| Malaise | 1 (3.7%) | 1 (3.6%) |
| Asthenia | 0 (0.0%) | 1 (3.6%) |
| Gastrointestinal Disorders | 4 (14.8%) | 3 (10.7%) |
| Nausea | 2 (7.4%) | 2 (7.1%) |
| Abdominal pain upper | 1 (3.7%) | 0 (0.0%) |
| Diarrhoea | 1 (3.7%) | 0 (0.0%) |
| Dry mouth | 0 (0.0%) | 1 (3.6%) |
| Dysgeusia | 1 (3.7%) | 0 (0.0%) |
| Rectal haemorrhage | 0 (0.0%) | 1 (3.6%) |
| Eye Disorders | 1 (3.7%) | 2 (7.1%) |
| Vision blurred | 1 (3.7%) | 1 (3.6%) |
| Eye pruritus | 0 (0.0%) | 1 (3.6%) |
| Metabolism and Nutrition Disorders | 1 (3.7%) | 0 (0.0%) |
| Anorexia | 1 (3.7%) | 0 (0.0%) |
| Reproductive System and Breast Disorders | 1 (3.7%) | 0 (0.0%) |
| Vaginal discharge | 1 (3.7%) | 0 (0.0%) |
| Vascular Disorders | 0 (0.0%) | 1 (3.6%) |
| Haematoma | 0 (0.0%) | 1 (3.6%) |

TABLE 28

|  | 100 mg MINOCIN ® Capsules | | Controlled-Release Caplet | |
|---|---|---|---|---|
| Number of subjects treated | 27 | | 28 | |
|  | Related | Not Rel | Related | Not Rel |
| Number of subjects with at least 1 event - N (%) | 9 (33.3) | 7 (25.9) | 5 (17.9) | 10 (35.7) |
| Number of events | 25 | 11 | 16 | 23 |
| Nervous System Disorders | 5 (18.5) | 6 (22.2) | 5 (17.9) | 4 (14.3) |
| Headache | 4 (14.8) | 2 (7.4) | 3 (10.7) | 4 (14.3) |
| Dizziness | 2 (7.4) | 4 (14.8) | 2 (7.1) | 0 (0.0) |
| Somnolence | 0 (0.0) | 0 (0.0) | 3 (10.7) | 1 (3.6) |
| Photophobia | 0 (0.0) | 0 (0.0) | 1 (3.6) | 0 (0.0) |
| General Disorders and Administration Site Conditions | 1 (3.7) | 2 (7.4) | 4 (14.3) | 2 (7.1) |
| Malaise | 0 (0.0) | 1 (3.7) | 1 (3.6) | 0 (0.0) |
| Asthenia | 0 (0.0) | 0 (0.0) | 0 (0.0) | 1 (3.6) |
| Gastrointestinal Disorders | 1 (3.7) | 3 (11.1) | 0 (0.0) | 3 (10.7) |
| Nausea | 0 (0.0) | 2 (7.4) | 0 (0.0) | 2 (7.1) |
| Abdominal pain upper | 1 (3.7) | 0 (0.0) | 0 (0.0) | 0 (0.0) |
| Diarrhoea | 0 (0.0) | 1 (3.7) | 0 (0.0) | 0 (0.0) |
| Dry mouth | 0 (0.0) | 0 (0.0) | 0 (0.0) | 1 (3.6) |
| Dysgeusia | 0 (0.0) | 1 (3.7) | 0 (0.0) | 0 (0.0) |
| Rectal haemorrhage | 0 (0.0) | 0 (0.0) | 1 (3.6) | 0 (0.0) |
| Eye Disorders | 0 (0.0) | 1 (3.7) | 2 (7.1) | 0 (0.0) |
| Vision blurred | 0 (0.0) | 1 (3.7) | 1 (3.6) | 0 (0.0) |
| Eye pruritus | 0 (0.0) | 0 (0.0) | 1 (3.6) | 0 (0.0) |
| Metabolism and Nutrition Disorders | 0 (0.0) | 1 (3.7) | 0 (0.0) | 0 (0.0) |
| Anorexia | 0 (0.0) | 1 (3.7) | 0 (0.0) | 0 (0.0) |
| Reproductive System and Breast Disorders | 0 (0.0) | 1 (3.7) | 0 (0.0) | 0 (0.0) |
| Vaginal discharge | 0 (0.0) | 1 (3.7) | 0 (0.0) | 0 (0.0) |

TABLE 28-continued

| | 100 mg MINOCIN ® Capsules | | Controlled- Release Caplet | |
|---|---|---|---|---|
| Vascular Disorders | 0 (0.0) | 0 (0.0) | 1 (3.6) | 0 (0.0) |
| Haematoma | 0 (0.0) | 0 (0.0) | 1 (3.6) | 0 (0.0) |

Note:

RELATED = Adverse events possibly, probably or definitely related to study treatment.

NOT REL = Adverse events not related or unlikely related to study treatment.

Subject Counts (% of all subjects) are presented.

Each subject is counted only once per treatment in the body system's total using the most related adverse event.

Only the most related for a subject is counted in each adverse event's total. Subjects may be counted more than once per treatment in the total number of subjects with AEs.

TABLE 29

| | 100 mg MINOCIN ® Capsules | | | Controlled- Release Caplet | | |
|---|---|---|---|---|---|---|
| Number of subjects treated | | | | | | |
| | 27 | | | 28 | | |
| | Mild | Moderate | Severe | Mild | Moderate | Severe |
| Number of subjects with at least 1 event | 11 (40.7) | 3 (11.1) | 0 (0.0) | 9 (32.1) | 3 (10.7) | 0 (0.0) |
| Number of events | 33 | 3 | 0 | 36 | 3 | 0 |
| Nervous System Disorders | 8 (29.6) | 3 (11.1) | 0 (0.0) | 6 (21.4) | 3 (10.7) | 0 (0.0) |
| Headache | 5 (18.5) | 1 (3.7) | 0 (0.0) | 5 (17.9) | 2 (7.1) | 0 (0.0) |
| Dizziness | 4 (14.8) | 2 (7.4) | 0 (0.0) | 2 (7.1) | 0 (0.0) | 0 (0.0) |
| Somnolence | 0 (0.0) | 0 (0.0) | 0 (0.0) | 3 (10.7) | 1 (3.6) | 0 (0.0) |
| Photophobia | 0 (0.0) | 0 (0.0) | 0 (0.0) | 1 (3.6) | 0 (0.0) | 0 (0.0) |
| General Disorders and Administration Site Conditions | 3 (11.1) | 0 (0.0) | 0 (0.0) | 6 (21.4) | 0 (0.0) | 0 (0.0) |
| Fatigue | 2 (7.4) | 0 (0.0) | 0 (0.0) | 5 (17.9) | 0 (0.0) | 0 (0.0) |
| Malaise | 1 (3.7) | 0 (0.0) | 0 (0.0) | 1 (3.6) | 0 (0.0) | 0 (0.0) |
| Asthenia | 0 (0.0) | 0 (0.0) | 0 (0.0) | 1 (3.6) | 0 (0.0) | 0 (0.0) |
| Gastrointestinal Disorders | 4 (14.8) | 0 (0.0) | 0 (0.0) | 3 (10.7) | 0 (0.0) | 0 (0.0) |
| Nausea | 2 (7.4) | 0 (0.0) | 0 (0.0) | 2 (7.1) | 0 (0.0) | 0 (0.0) |
| Abdominal pain upper | 1 (3.7) | 0 (0.0) | 0 (0.0) | 0 (0.0) | 0 (0.0) | 0 (0.0) |
| Diarrhoea | 1 (3.7) | 0 (0.0) | 0 (0.0) | 0 (0.0) | 0 (0.0) | 0 (0.0) |
| Dry mouth | 0 (0.0) | 0 (0.0) | 0 (0.0) | 1 (3.6) | 0 (0.0) | 0 (0.0) |
| Dysgeusia | 1 (3.7) | 0 (0.0) | 0 (0.0) | 0 (0.0) | 0 (0.0) | 0 (0.0) |
| Rectal haemorrhage | 0 (0.0) | 0 (0.0) | 0 (0.0) | 1 (3.6) | 0 (0.0) | 0 (0.0) |
| Eye Disorders | 1 (3.7) | 0 (0.0) | 0 (0.0) | 2 (7.1) | 0 (0.0) | 0 (0.0) |
| Vision blurred | 1 (3.7) | 0 (0.0) | 0 (0.0) | 1 (3.6) | 0 (0.0) | 0 (0.0) |
| Eye pruritus | 0 (0.0) | 0 (0.0) | 0 (0.0) | 1 (3.6) | 0 (0.0) | 0 (0.0) |
| Metabolism and Nutrition Disorders | 1 (3.7) | 0 (0.0) | 0 (0.0) | 0 (0.0) | 0 (0.0) | 0 (0.0) |
| Anorexia | 1 (3.7) | 0 (0.0) | 0 (0.0) | 0 (0.0) | 0 (0.0) | 0 (0.0) |
| Reproductive System and Breast Disorders | 1 (3.7) | 0 (0.0) | 0 (0.0) | 0 (0.0) | 0 (0.0) | 0 (0.0) |
| Vaginal discharge | 1 (3.7) | 0 (0.0) | 0 (0.0) | 0 (0.0) | 0 (0.0) | 0 (0.0) |
| Vascular Disorders | 0 (0.0) | 0 (0.0) | 0 (0.0) | 1 (3.6) | 0 (0.0) | 0 (0.0) |
| Haematoma | 0 (0.0) | 0 (0.0) | 0 (0.0) | 1 (3.6) | 0 (0.0) | 0 (0.0) |

Note:

Subject Counts (% of all subjects) are presented.

Each subject is counted only once per treatment in the body system's total using the most severe adverse event.

Only the greatest severity for a subject is counted in each adverse event's total.

Subjects may be counted more than once per treatment in the total number of subjects with AEs.

Plasma specimens are collected for minocycline analysis pre-dose on Day 1, Day 4, and Day 5 of each period. Sampling on Day 6 is pre-dose and at 0.5, 1.0, 1.5, 2.0, 3.0, 4.0, 5.0, 6.0, 8.0, 12.0, 12.5, 13.0, 13.5, 14.0, 15.0, 16.0, 17.0, 18.0 and 20.0 hours post-dose. On Day 7, subjects are discharged from the research facility after a 24-hour post-dose sample is obtained. Subjects return to the clinic each morning on Days 8 and 9 (at 48 and 72 hours post-dose, respectively) for additional sampling.

The definitions of individual subject PK parameters and their methods of calculation, as used in this study, are presented in Table 30.

TABLE 30

| Symbol | Definition | Method of Calculation |
|---|---|---|
| $C_{max}$ | Maximum observed steady-state plasma concentration | As observed on Day 6 of each study phase. |
| $AUC_{(0-24)}$ | The area under the plasma concentration versus time curve from time of morning dose to the end of the 24-hour dosing interval at steady-time | Integration of the observed plasma concentration vs time curve from the time of morning dose on Day 6 (of each phase) through 24 hours later, using the linear trapezoidal method. |
| $T_{max}$ | Time of occurrence of $C_{max}$, relative to the time of the Day 6 morning dose. | As observed on Day 6 of each study phase. |
| $C_{min}$ | Minimum observed steady-state plasma concentration | As observed on Day 6 of each study phase. |
| $C_{av}$ | Average steady-state plasma concentration | $AUC_{(0-24)}$ divided by 24. |
| PTF | Percent fluctuation from peak to trough at steady state | $100 \times (C_{max} - C_{min})/C_{av}$ |

Each of these parameters are analyzed using an analysis of variance model with terms for subject, subject within sequence, period, and treatment. The sequence effect is tested against the variance for subjects within sequence; all other effects are tested against the residual variance of the model. Least squares means for each treatment, and the difference between the treatment least squares means are calculated. For $AUC_{(0-24)}$, $C_{max}$, and $C_{min}$ the parameters are also analyzed after log transformation. Ninety percent 2-sided confidence intervals are constructed on the treatment differences of the untransformed parameters, and on the ratio of geometric means for $AUC_{(0-24)}$, $C_{max}$, and $C_{min}$.

with effects of period, day, and period-day interaction for each treatment separately, using only the pre-dose minocycline concentrations on Days 4, 5, 6, and 7.

Twenty-eight healthy subjects, 7 men and 21 women, are enrolled in this study. All of them receive treatment with the assigned medication for Period 1; 14 subjects receive the Test product in Period 1, and 14 subjects receive the Reference product, in accordance with the randomization schedule. Subject 9 is dropped from the study before receiving the first dose of study medication (Reference product) at Period 2, after yielding a positive result on drug screening.

The results of the planned analysis of the steady state PK parameters for this study are presented in Table 31.

TABLE 31

Summary of Planned Analysis of Steady-State Pharmacokinetics Parameters
All Completed Subject (N = 27)

| Parameter | Least Squares Means | | Difference/ 90% CI | Ratio of Geom Means/ 90% CI | P Values | | |
|---|---|---|---|---|---|---|---|
| | Test | Reference* | | | Seq | Period | Treat |
| $C_{max}$ (µg/mL) | 2.63 | 2.92 | −0.28 (−0.52, −0.04) | 90% (82%, 99%) | 0.002 | 0.947 | 0.069 |
| $AUC_{(0-24)}$ (µg × hr/mL) | 33.32 | 46.35 | −13.0 (−16.8, −9.2) | 72% (65%, 79%) | 0.003 | 0.920 | <0.001 |
| $T_{max}$ (hr) | 3.34 | 3.00 | 0.34 (−0.93, 1.62) | — | 0.085 | 0.315 | 0.651 |
| $C_{min}$ (µg/mL) | 0.63 | 1.23 | −0.60 (−0.72, −0.48) | 49% (42%, 58%) | 0.015 | 0.541 | <0.001 |
| $C_{av}$ (µg/mL) | 1.39 | 1.93 | −0.54 (−0.70, −0.38) | — | 0.005 | 0.220 | <0.001 |
| PTF (%) | 144.8 | 88.4 | 56.4 (48.0, 64.8) | — | 0.778 | 0.614 | <0.001 |

*Note: All Reference product parameters are dose-adjusted to 135 mg total dose.
CI = confidence interval,
Seq = Sequence;
P values are from analysis of variance with effects of subject, subject within sequence, period, and treatment.
For $AUC_{(0-24)}$, $C_{max}$, and $C_{min}$, the data are log-transformed prior to analysis.

The plasma minocycline concentrations are plotted versus sampling point for each individual subject and period as well as for the means by treatment. The achievement of steady state is investigated by performing an analysis of variance The least squares mean $AUC_{(0-24)}$ at Day 6 for the Test product is 33.32 µg×hr/mL, and the least squares mean Cmax at Day 6 is 2.63 µg/mL. These are to be compared with the respective dose-adjusted values of 46.35 µg×hr/mL and 2.92

µg/mL for the Reference product. The ratio of geometric means is 72% for $AUC_{(0-24)}$, 90% for $C_{max}$, and 49% for $C_{min}$.

The analysis of variance reveals a statistically significant effect of sequence which appears consistently across most of the PK parameters. Further investigation shows that there is a statistically significant difference in the PK parameters between periods within each treatment group. A supplementary analysis of the PK parameters is therefore carried out taking the data from each period separately. The applicable analysis of variance is a 1-way model, with treatment as the only independent term. Table 32 shows the results.

TABLE 32

Summary of Supplementary Analysis of Steady-State Pharmacokinetic Parameters
By Period, By Treatment
All Completed Subjects (N = 27)

| Parameter | Period | Least Squares Means | | Difference/ 90% CI | Ratio of Geom Means/90% CI | P Value Treat |
| --- | --- | --- | --- | --- | --- | --- |
| | | Test | Reference* | | | |
| $C_{max}$ (µg/mL) | 1 | 2.20 | 3.45 | −1.25 (−1.84, −0.67) | 63% (51%, 78%) | 0.001 |
| | 2 | 3.07 | 2.38 | 0.69 (0.19, 1.18) | 128% (108%, 153%) | 0.021 |
| $AUC_{(0-24)}$ (µg × hr/mL) | 1 | 28.4 | 54.1 | −25.7 (−34.7, −16.7) | 52% (42%, 65%) | <0.001 |
| | 2 | 38.3 | 38.6 | −0.4 (−7.1, 6.3) | 99% (83%, 117%) | 0.901 |
| $T_{max}$ (hr) | 1 | 3.62 | 1.96 | 1.65 (1.18, 2.12) | — | <0.001 |
| | 2 | 3.07 | 4.04 | −0.97 (−3.44, 1.51) | — | 0.071 |
| $C_{min}$ (µg/mL) | 1 | 0.52 | 1.49 | −0.98 (−1.25, −0.70) | 34% (27%, 43%) | <0.001 |
| | 2 | 0.74 | 0.97 | −0.23 (−0.42, −0.04) | 70% (51%, 98%) | 0.080 |
| $C_{av}$ (µg/mL) | 1 | 1.18 | 2.25 | −1.07 (−1.45, −0.69) | — | <0.001 |
| | 2 | 1.59 | 1.61 | −0.02 (−0.29, 0.26) | — | 0.924 |
| PTF (%) | 1 | 142.6 | 88.1 | 54.5 (40.8, 68.3) | — | <0.001 |
| | 2 | 147.0 | 88.7 | 58.2 (44.0, 72.5) | — | <0.001 |

*Note: All Reference product parameters are dose-adjusted to 135 mg total dose.
CI = confidence interval, P values are from analysis of variance with effects of treatment. For $AUC_{(0-24)}$, $C_{max}$, and $C_{min}$, the data are log-transformed prior to analysis.

In Period 1, the mean $AUC_{(0-24)}$ at Day 6 for the Test product is 28.4 µg×hr/mL, and the least squares mean $C_{max}$ at Day 6 is 2.20 µg/mL. The respective dose-adjusted values for the Reference product are 54.1 µg×hr/mL and 3.45 µg/mL. The ratio of geometric means is 52% for $AUC_{(0-24)}$, 63% for $C_{max}$, and 34% for $C_{min}$. In Period 1, the value of $T_{max}$ for the Test product is 3.62 hours compared to 1.96 hours for the Reference product. The difference between treatments is statistically significant for all PK parameters in Period 1, showing the Test product to be less bioavailable and more slowly absorbed than the Reference product.

Figure 9:
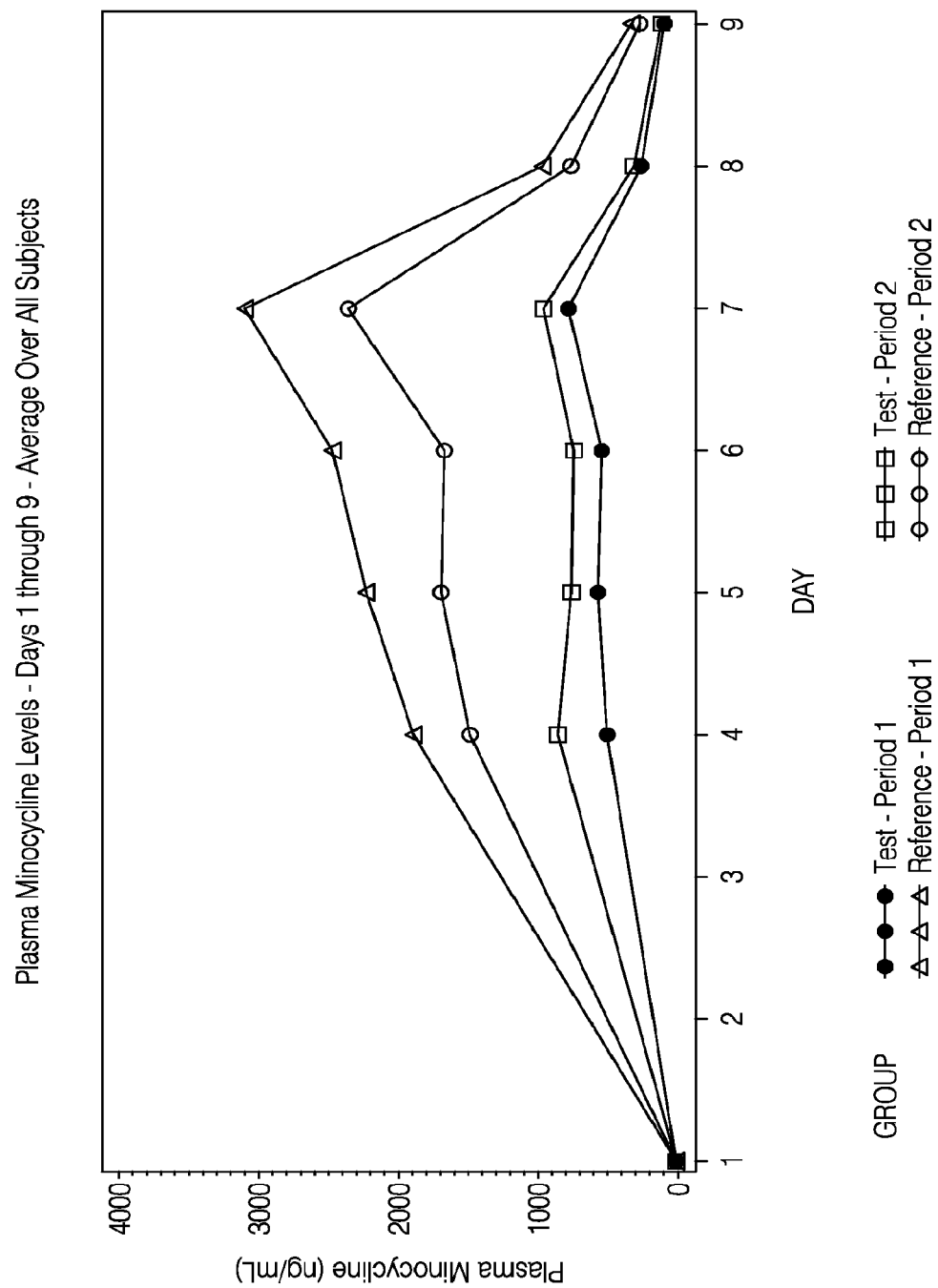
FIG. 9 shows minocycline plasma concentrations as a function of time across formulations.
Figure 10:
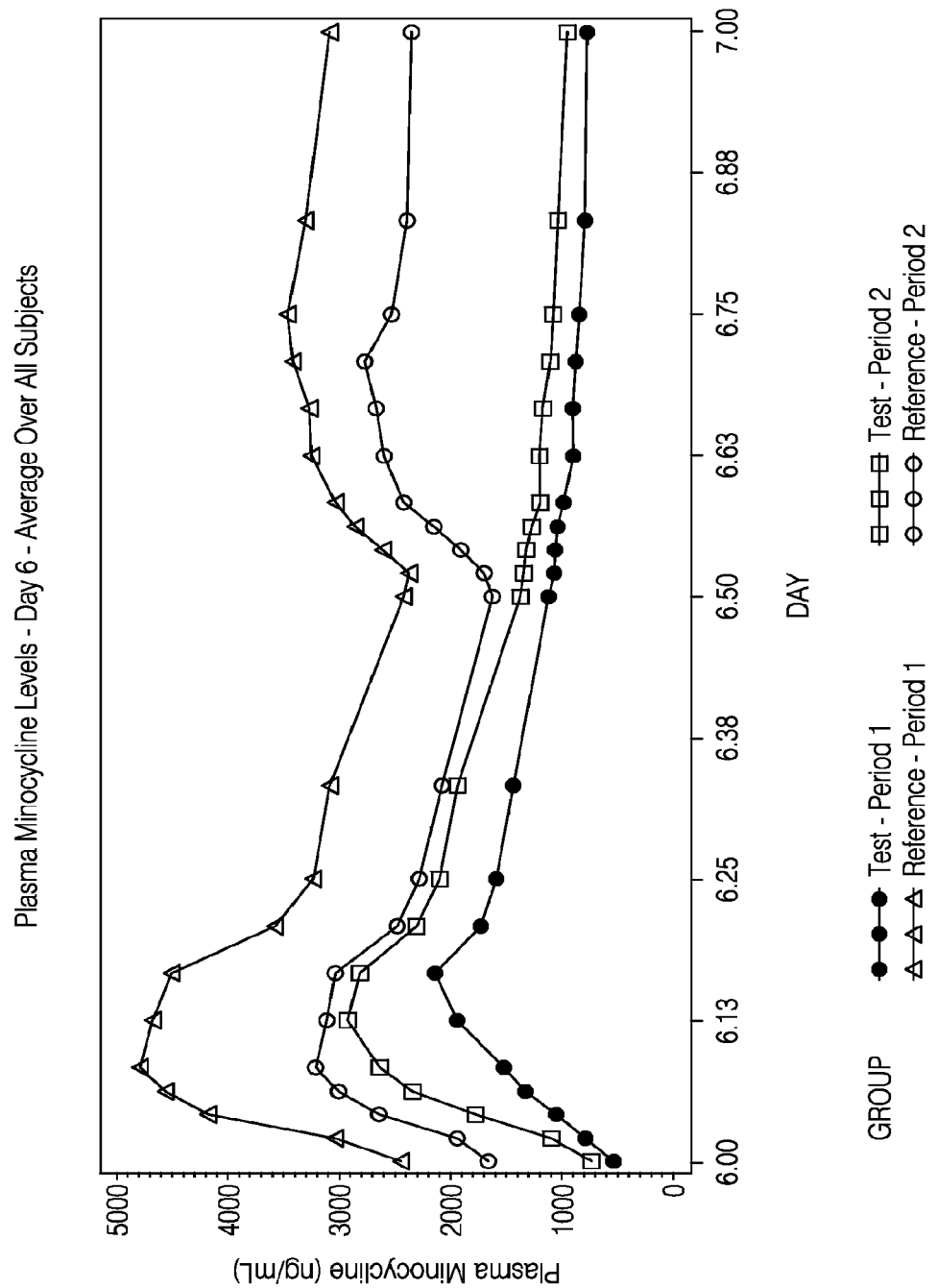
FIG. 10 shows minocycline plasma concentrations as a function of time across formulations.

Mean plasma minocycline concentrations are plotted versus time in FIGS. 9-10. The dose-adjusted curves show that the Reference product is less bioavailable, and the Test product more bioavailable, in Period 2 compared to Period 1.

In Period 2, the mean $AUC_{(0-24)}$ at Day 6 for the Test product is 38.6 µg×hr/mL, and the least squares mean $C_{max}$ at Day 6 is 3.07 µg/mL. The respective dose-adjusted values for the Reference product are 38.3 µg×hr/mL and 2.38 µg/mL. The ratio of geometric means is 99% for $AUC_{(0-24)}$, 128% for $C_{max}$, and 70% for $C_{min}$. In Period 2, the value of $T_{max}$ for the Test product is 3.07 hours compared to 4.04 hours for the Reference product. The difference between treatments is statistically significant only for $C_{max}$ and PTF in Period 2, with the Reference product showing a higher $C_{max}$ than the Test product. Thus, the Period 2 results are qualitatively different from the Period 1 results in this study.

Figure 11:
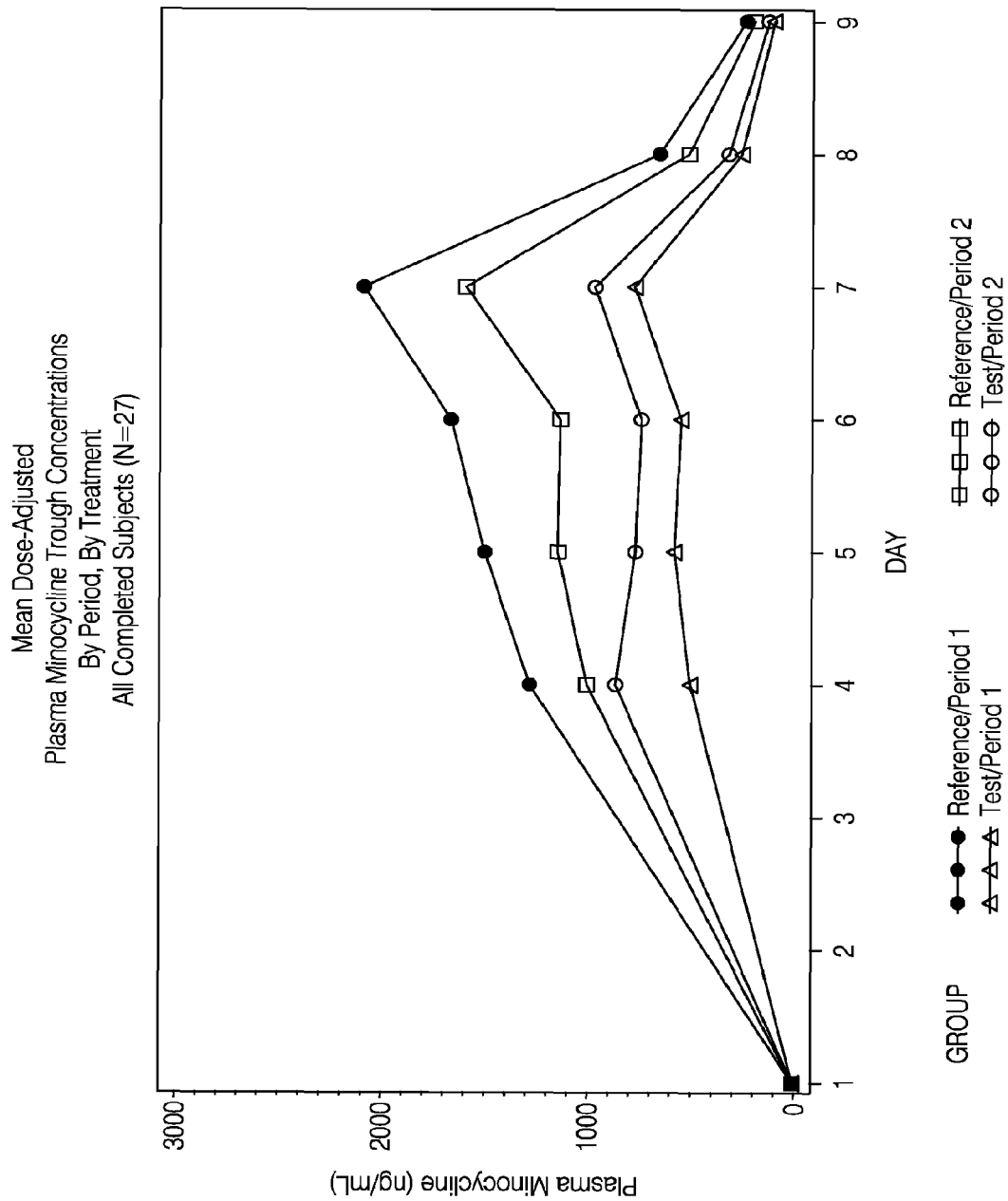
FIG. 11 shows minocycline plasma concentrations as a function of time across formulations.
Figure 12:
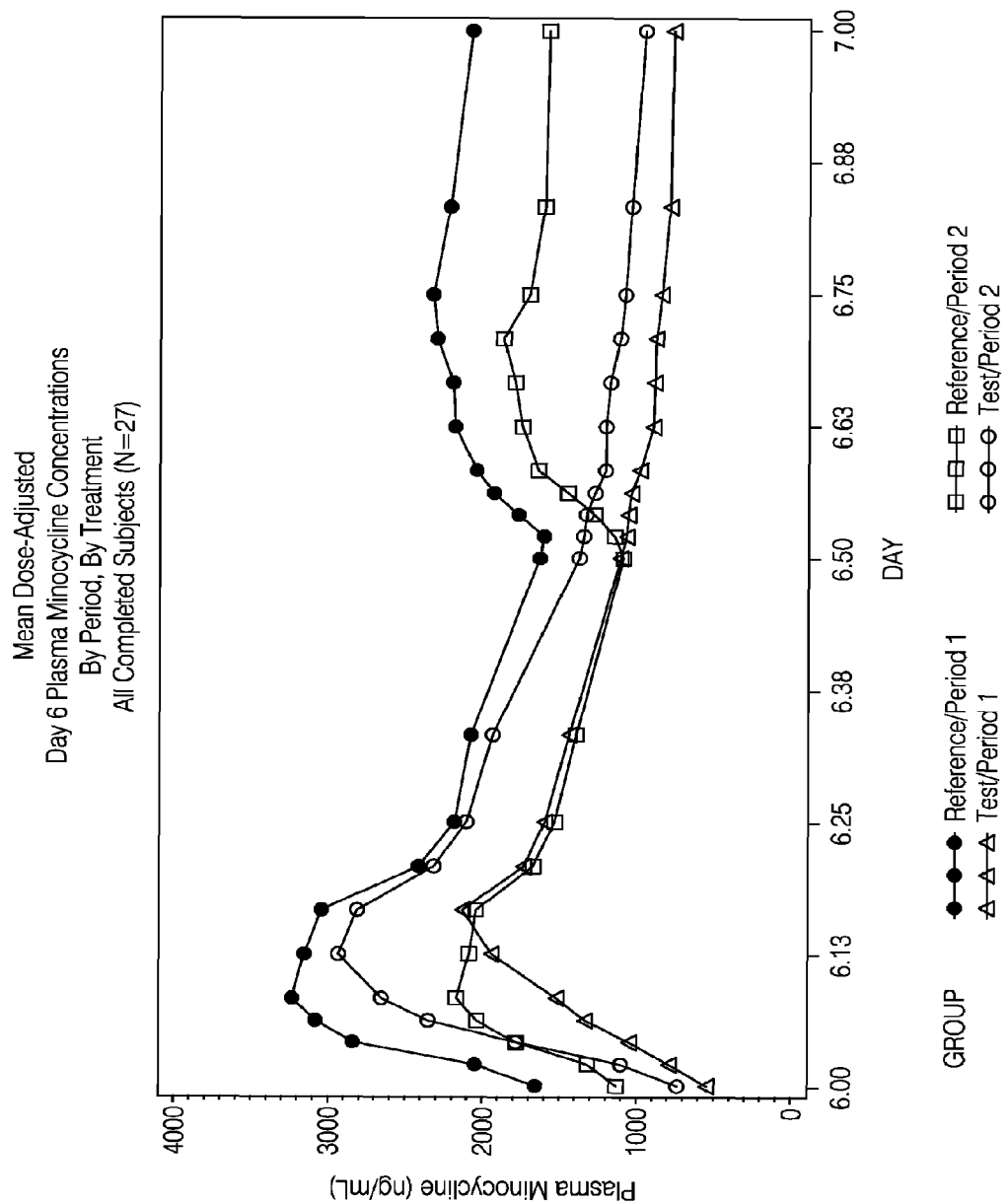
FIG. 12 shows minocycline plasma concentrations as a function of time across formulations.

The mean dose-adjusted concentration curves are displayed by treatment and period in FIGS. 11-12. FIG. 11 indicates that trough concentrations are still increasing on Day 6. An analysis of variance is performed to test whether steady state has been achieved. The analysis is performed separately for each treatment on the data from combined periods (including effects of period, day, and period-day interaction), and on the data from each treatment and each period separately (including effects of day only). Only the trough concentrations from Day 5, Day 6, and Day 7 are included in the analysis. The results showed a statistically significant effect of day, indicating that the trough plasma concentrations are increasing between Day 5 and Day 7 for both treatments and in both periods.

Twenty-eight healthy adult volunteers, 7 men and 21 women, ranging in age from 19 to 50 years old, are enrolled in this 2-way crossover study to determine the relative bioavailability at steady state of 2 formulations of minocycline HCl. The Test product is Controlled-Release Minocycline HCl Caplets, 135 mg, and the Reference product is MINOCIN® Capsules, 100 mg. The Test product is administered once daily for 6 consecutive days, and the Reference product is administered every 12 hours for 6 consecutive days. A total of 27 subjects receive the full 6 days of treatment with both formulations and are included in the analysis.

In the planned statistical analysis, the least squares mean $AUC_{(0-24)}$ at Day 6 for the Test product is 33.32 µg×hr/mL, and the least squares mean $C_{max}$ at Day 6 is 2.63 µg/mL. These are to be compared with the respective dose-adjusted values of 46.35 µg×hr/mL and 2.92 µg/mL for the Reference product. The ratio of geometric means is 72% for $AUC_{(0-24)}$, 90% for $C_{max}$, and 49% for $C_{min}$.

There is a statistically significant sequence effect in this study, associated with a significant difference in the PK parameters measured in the 2 study periods. In Period 1, the mean $AUC_{(0-24)}$ at Day 6 for the Test product is 28.4 µg×hr/mL, and the least squares mean $C_{max}$ at Day 6 is 2.20 µg/mL. The respective dose-adjusted values for the Reference product are 54.1 µg×hr/mL and 3.45 µg/mL. The ratio of geometric means is 52% for $AUC_{(0-24)}$, 63% for $C_{max}$, and 34% for $C_{min}$.

In Period 1, the value of $T_{max}$ for the Test product is 3.62 hours compared to 1.96 hours for the Reference product. The difference between treatments is statistically significant for all PK parameters in Period 1, showing the Test product to be less bioavailable and more slowly absorbed than the Reference product. In Period 2, the mean $AUC_{(0-24)}$ at Day 6 for the Test product is 38.6 µg×hr/mL, and the least squares mean $C_{max}$ at Day 6 is 3.07 µg/mL. The respective dose-adjusted values for the Reference product are 38.3 µg×hr/mL and 2.38 µg/mL. The ratio of geometric means is 99% for $AUC_{(0-24)}$, 128% for $C_{max}$, and 70% for $C_{min}$. In Period 2, the value of $T_{max}$ for the Test product is 3.07 hours compared to 4.04 hours for the Reference product. The difference between treatments is statistically significant only for $C_{max}$ and PTF in Period 2, with the Reference product showing a higher $C_{max}$ than the Test product. Thus, the Period 2 results are qualitatively different from the Period 1 results in this study. In Period 2, the Reference product is found to be less bioavailable than in Period 1, and the Test product is found to be slightly more bioavailable in Period 2 than in Period 1.

In Period 1, the Test product is clearly less bioavailable and more slowly absorbed than the Reference product. These results are consistent with the findings of the single-dose bioavailability study described in Example 12 above. In that study, a single dose of Modified-Release Minocycline HCl Caplets, 135 mg, yields a mean $AUC_{inf}$ of about 41.2 µg×hr/mL and mean $C_{max}$ of about 1.83 µg/mL (see Table 3). The dose-adjusted results for MINOCIN® Capsules, 100 mg, in that study are a mean $AUC_{inf}$ of about 48.2 µg×hr/mL and a mean $C_{max}$ of about 2.24 µg/mL. The respective mean values of $T_{max}$ after a single dose are 3.85 hours and 2.92 hours (see Table 4). The ratio of geometric means of AUC and $C_{max}$ in the single-dose study are 86% and 82%, respectively (see Table 5). Thus, the single-dose PK results for these products are consistent with the findings of Period 1 in the present repeat-dose study in showing that the new minocycline formulation is less bioavailable and more slowly absorbed than the MINOCIN® product.

The differences between treatment comparisons in the 2 periods are associated with an apparent difference between the sequence groups (Test-Reference vs Reference-Test) in minocycline bioavailability. The subject group receiving treatment in the order Reference-Test shows higher plasma minocycline concentrations overall, after adjustment for treatment differences, than the subject group receiving treatment in the order Test-Reference. Consequently, the PK parameter estimates for the 2 treatments are more similar in Period 2 than in Period 1.

The lowest exposures which yield adverse effects in the repeat-dose primate toxicology studies are on the order of 15 µg/mL for 4 weeks and 7 µg/mL for 13 weeks. These exposures are well above the levels observed in this study. The results show a statistically significant effect indicating that the trough plasma concentrations are increasing between Day 5 and Day 7 for both treatments and in both periods.

The most commonly observed adverse events in this study are headache, fatigue, somnolence, dizziness, and nausea. These adverse events are observed at the levels expected for the dose range of minocycline administered in this study (approximately 2 to 3 mg/kg/day), as indicated in current MINOCIN® minocycline labeling.

Mean $AUC_{(0-24)}$ at Day 6 for Controlled-Release Minocycline HCl Caplets, 135 mg, after 6 days of once daily dosing, is 33.32 µg×hr/mL, and mean $C_{max}$ at Day 6 is 2.63 µg/mL. The new CR formulation is absorbed more slowly and yields lower dose-adjusted systemic exposure than commercially available MINOCIN® Capsules.

Example 16

A multi-center, 12-week, randomized, double-blinded, placebo-controlled, dose-ranging study examines the effects of controlled-release minocycline in the treatment of moderate to severe facial acne vulgaris.

The study includes 250 subjects from up to 18 study centers in the United States. Subjects are between 12 to 30 years old at the time of enrollment, weigh between 39.1 kg and 102.3 kg (86-225 lb) and are diagnosed with moderate to severe facial acne vulgaris. They are required to have at least 20 and no more than 100 inflammatory facial lesions and less than 5 facial nodules or cysts. Females of childbearing potential have a negative urine pregnancy test result (25 µg/mL sensitivity), are practicing contraception, and are willing to continue on the contraceptive for the duration of the study. Subjects or a parent/guardian provide informed consent, The main criteria for exclusion are known sensitivity to minocycline or any of the components; females who are pregnant; males with facial hair; use of supplements containing aluminum, calcium, iron, or magnesium, or vitamin A; or a prior history of complicating illnesses or medications. Subjects randomly are assigned 1 of 3 active treatments (1, 2, or 3 mg/kg daily) or placebo according to the dosing schedule in Table 33. The study drug is administered once daily in the morning throughout the 84-day study. Randomization is stratified based on each subject's weight to ensure that all treatment groups contain equal numbers of subjects in each weight category. The primary efficacy endpoint is the reduction in the number and percentage of inflammatory lesions (papules, pustules, nodules, cysts) from baseline (day 1) to day 84. Secondary efficacy endpoints include the reduction in inflammatory lesions at interim visits (days 28 and 56), changes in noninflammatory (open and closed comedones) and total (inflammatory and noninflammatory) lesion counts, and changes in the Investigator's Static Global Evaluation of acne severity. Safety assessments are based on the incidence of adverse drug events (ADEs) reported at each post-baseline visit (days 28, 54, 84) and at telephone contacts on days 7 and 91 as well as ADEs recorded in each subject's daily diary during the first 5 days of treatment. Complete blood counts and serum chemistries are monitored at baseline and at the end of the study for evidence of clinically significant changes.

TABLE 33

| Treatment Group | Weight, lb | Weight, kg | Tablet Combination, mg | Actual Dose Range, mg/kg |
|---|---|---|---|---|
| 1 mg/kg | 86-149 | 39.1-67.7 | 45 + placebo | 0.66-1.15 |
|  | 150-225 | 68.2-102.3 | 45 + 45 | 0.88-1.32 |
| 2 mg/kg | 86-124 | 39.1-56.4 | 45 + 45 | 1.60-2.30 |
|  | 125-174 | 56.8-79.1 | 135 + placebo | 1.71-2.38 |
|  | 175-225 | 79.6-102.3 | 135 + 45 | 1.76-2.26 |
| 3 mg/kg | 86-115 | 39.1-52.3 | 135 + placebo | 2.58-3.45 |
|  | 116-145 | 52.7-65.9 | 135 + 45 | 2.73-3.41 |
|  | 146-170 | 66.4-77.3 | 150 + 45 | 2.52-2.94 |
|  | 171-225 | 77.7-102.3 | 135 + 135 | 2.64-3.47 |
| Placebo | 86-225 | 39.1-102.3 | Placebo + placebo | 0 |

Statistical analyses are performed using SAS® PC Version 6.12. Subject demographics are summarized using descriptive statistics. Interval data are compared between treatment groups using 2-way analysis of variance (treatment and center) with interaction. Categorical data are compared between groups using Cochran-Mantel-Haenszel statistics, adjusted for center.

The primary and secondary efficacy analyses are performed in the intent-to-treat (ITT) population, which is defined as all randomized subjects who received the study drug. Last observation carried forward is employed. The absolute lesion count, the change from baseline, and the percentage change from baseline are analyzed using the 2-way analysis of variance (treatment and center) with interaction. The dichotomized Investigator's Static Global Evaluation defines a treatment success as a score of 3 (clear) or 4 (almost clear), and treatment groups are compared using Cochran-Mantel-Haenszel statistics. A Cochran-Mantel-Haenszel analysis also is performed to compare the proportion of subjects who experience an improvement of 2 or more points from baseline to day 84.

Of 241 subjects randomized, 233 subjects are given medication and included in the safety and ITT populations (Table 34). Reasons for early discontinuation are ADEs (16 subjects), withdrawal of consent (9 subjects), lost to follow-up (8 subjects), and other (16 subjects). The treatment groups are similar with regard to the majority of demographics (age range, 17-19 years; mean height, 65.6-67.1 in; mean weight 146.9-149.6 lb). Race distribution among the groups also is similar, with more than 80% of the subjects being white. The only statistically significant difference (P=0.0481) is noted in the gender distribution: 64.4% of subjects in the controlled-release-minocycline 1-mg/kg treatment group are male compared with 45.5% to 56.7% in the other treatment groups.

Figure 13:
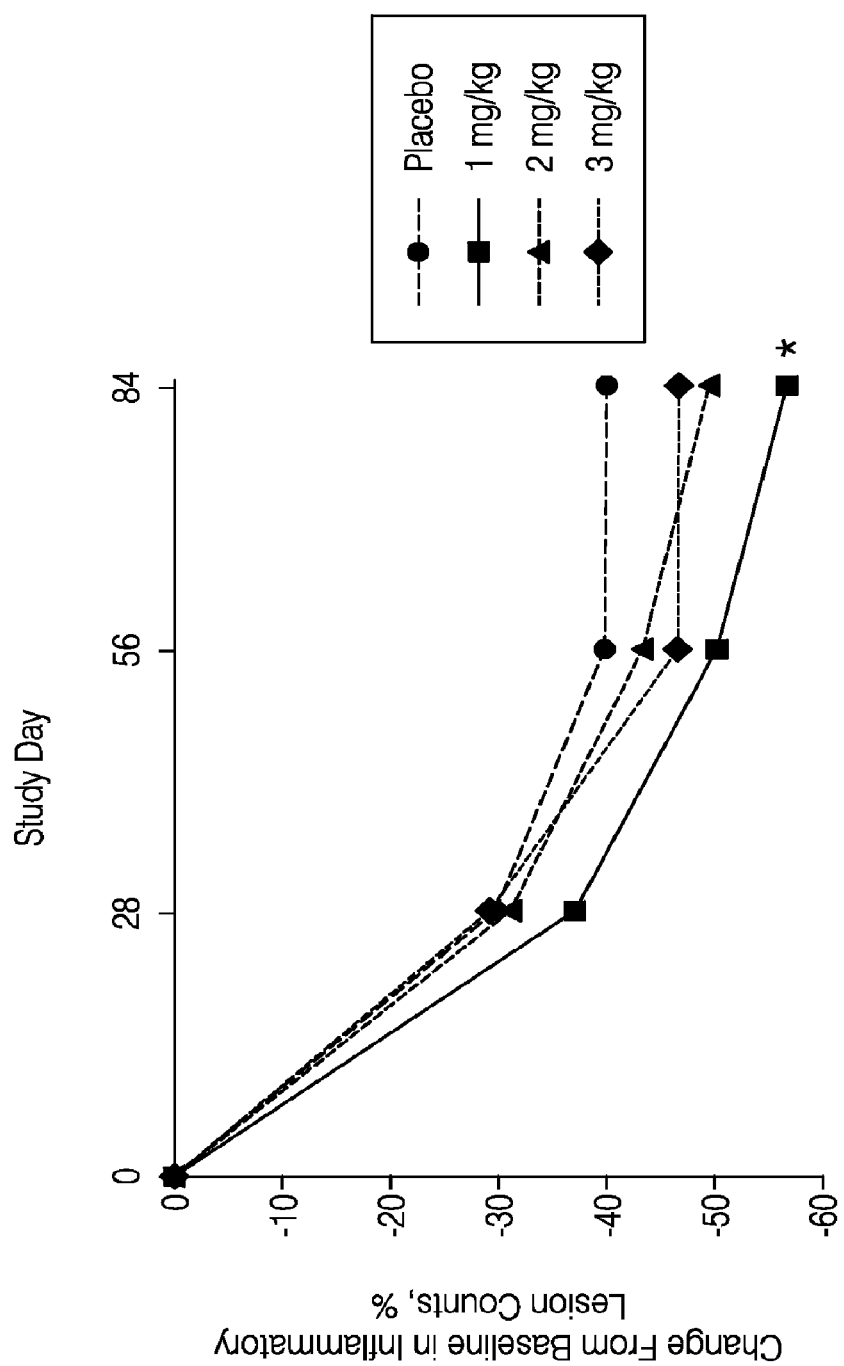
FIG. 13 shows percentage decrease from baseline in inflammatory lesion counts in several extended-release minocycline hydrochloride dose groups and a placebo group.

Mean inflammatory lesion counts at baseline range from 38.8 in the 1-mg/kg treatment group to 47.0 in the 2-mg/kg treatment group; no statistically significant differences are noted among the baseline counts (Table 35). The mean number of inflammatory lesions is significantly greater (P=0.014) in the 2-mg/kg treatment group compared with placebo. All treatment groups show a decrease from baseline in the mean number of inflammatory lesions. By day 56, the decrease observed in all controlled-release-minocycline treatment groups numerically is greater than the placebo group; by day 84, the number of inflammatory lesions decreases by approximately 50% in all treatment groups except the placebo group (FIG. 13; asterisk indicates P=0.015). The decrease in the number of lesions from baseline to day 84 ranges from −18.3 in the controlled-release-minocycline 3-mg/kg treatment group to −23.7 in the 2-mg/kg treatment group compared with −7.2 in the placebo group. Percentage change from baseline to day 84 ranges from −46.6% in the controlled-release-minocycline 3-mg/kg treatment group to −56.8% in the 1-mg/kg treatment group compared with −39.4% in the placebo group. No dose-dependent effect is observed; the percentage decrease in the number of inflammatory lesions in the controlled-release-minocycline 1-mg/kg group is equal to or greater than that observed with 2 mg/kg or 3 mg/kg. The pairwise difference between controlled-release minocycline 1 mg/kg and placebo in the percentage decrease in inflammatory lesions from baseline to day 84 is statistically significant (P=0.015).

TABLE 34

Subject Baseline Demographics (Intent-to-Treat Population)

| | Controlled-Release Minocycline Hydrochloride | | | Placebo (n = 55) | Total (N = 233) | Overall P Value |
|---|---|---|---|---|---|---|
| | 1 mg/kg (n = 59) | 2 mg/kg (n = 59) | 3 mg/kg (n = 60) | | | |
| Age, y | | | | | | .9275 |
| Mean | 17.6 | 17.8 | 17.6 | 17.9 | 17.7 | |
| Gender, n (%) | | | | | | .0481 |
| Male | 38 (64.4) | 29 (49.2) | 34 (56.7) | 25 (45.5) | 126 (54.1) | |
| Female | 21 (35.6) | 30 (50.8) | 26 (43.3) | 30 (54.5) | 107 (45.9) | |
| Race, n (%) | | | | | | .6656 |
| White | 50 (84.7) | 50 (84.7) | 57 (95.0) | 48 (87.3) | 205 (88.0) | |
| Black | 3 (5.1) | 3 (5.1) | 1 (1.7) | 2 (3.6) | 9 (3.9) | |
| Hispanic | 5 (8.5) | 4 (6.8) | 1 (1.7) | 4 (7.3) | 14 (6.0) | |
| American Indian | 0 (0) | 1 (1.7) | 0 (0) | 1 (1.8) | 2 (0.9) | |
| Asian/Pacific Islander | 1 (1.7) | 1 (1.7) | 1 (1.7) | 0 (0) | 3 (1.3) | |
| Height, in | | | | | | .1351 |
| Mean | 67.1 | 65.6 | 66.3 | 66.8 | 66.5 | |
| Weight, lb | | | | | | .9693 |
| Mean | 148.6 | 148.2 | 149.6 | 146.9 | 148.3 | |

TABLE 35

Primary Efficacy Endpoint: Inflammatory
Lesion Counts (Intent-to-Treat Population)*

| | Controlled-Release Minocycline Hydrochloride | | | Placebo |
|---|---|---|---|---|
| | 1 mg/kg (n = 59) | 2 mg/kg (n = 59) | 3 mg/kg (n = 60) | (n = 55) |
| Baseline | | | | |
| Mean | 38.8 | 47.0 | 39.1 | 40.3 |
| P value[H] | .697 | .014 | .944 | NA |
| Change from baseline to day 84 | | | | |
| Mean | −21.8 | −23.7 | −18.3 | −17.2 |
| P value[H] | .213 | .043 | .623 | NA |
| Change from baseline to day 84, % | | | | |
| Mean | −56.8 | −49.3 | −46.6 | −39.4 |
| P value[H] | .015 | .160 | .271 | NA |

*NA indicates not applicable.
[H]P value vs placebo.

Results of subgroup analyses performed by gender body weight, body mass index (BMI), and number of inflammatory lesions at baseline generally are similar to those obtained in the overall ITT population. The mean number of inflammatory lesions decreases over time in all treatment groups, and the mean decrease tends to be greater in subjects in the controlled-release-minocycline treatment groups than in the placebo group. The reduction in inflammatory lesions is not dose related. There is no evidence of gender-related effects on the overall efficacy of controlled-release minocycline. However, body weight analyses indicate that controlled-release minocycline appears to be somewhat less effective in the heaviest subjects ($\geq$171 lb) and in those with a BMI of 25 or more than in subjects who weigh less.

In the subgroup of subjects with at least 25 and no more than 50 inflammatory lesions at baseline, a significantly greater (P=0.006) percentage decrease in the number of inflammatory lesions is observed in the controlled-release-minocycline 1-mg/kg treatment group than in the placebo group.

Baseline noninflammatory lesion counts ranges from 36.9 in the controlled-release minocycline 3-mg/kg treatment group to 44.6 in the 2-mg/kg treatment group, and total (inflammatory and noninflammatory) lesion counts ranges from 76.0 in the 3-mg/kg treatment group to 91.6 in the 2-mg/kg treatment group. There are no statistically significant differences among the dose groups or from placebo for both noninflammatory and total lesion counts. As with the number of inflammatory lesions, the number of noninflammatory and total lesions decreases over the treatment period in all 3 dose groups, though the changes are smaller. There are no significant dose-related effects.

Global assessment scores also are similar (no statistically significant differences) among the groups and are not different from placebo at baseline. Analysis of changes in global assessment scores shows an overall improvement in all 4 treatment groups, with a mean change of approximately one unit and no evidence of dose-related effects. No statistically significant differences between study groups are noted. The percentage of subjects who have a static global assessment of clear or almost clear at day 84 is 23.7%, 16.9% and 30.0%, in the controlled-release-minocycline 1-, 2-, and 3-mg/kg treatment groups, respectively, compared with 14.5% in the placebo group. Results of subgroup analyses by gender, body weight, and BMI generally are similar to those obtained for the entire ITT population.

The overall difference in the incidence of treatment-emergent ADEs between treatment groups is not statistically significant (P=0.590) and is summarized in Table 36.

TABLE 36

Treatment-Related Treatment-Emergent Adverse Drug Events
Occurring in $\geq$ 5% of Subjects (Intent-to-Treat Population)*

| | Controlled-Release Minocycline Hydrochloride | | | Placebo, n |
|---|---|---|---|---|
| Adverse Drug Events | 1 mg/kg, n (%) (n = 59) | 2 mg/kg, n (%) (n = 59) | 3 mg/kg, n (%) (n = 60) | (%) (n = 55) |
| $\geq$1 event | 31 (53) | 33 (56) | 39 (65) | 28 (51) |
| Ear and Labyrinth Disorders | 3 (5) | 3 (5) | 4 (7) | 1 (2) |
| Vertigo | 1 (2) | 1 (2) | 3 (5) | 0 (0) |
| Gastrointestinal Tract Disorders | 9 (15) | 14 (24) | 20 (33) | 18 (33) |
| Abdominal pain, upper | 0 (0) | 1 (2) | 3 (5) | 4 (7) |
| Diarrhea NOS | 3 (5) | 1 (2) | 3 (5) | 1 (2) |
| Gastrointestinal tract pain NOS | 2 (3) | 3 (5) | 4 (7) | 7 (13) |
| Nausea | 4 (7) | 8 (14) | 13 (22) | 7 (13) |
| Vomiting NOS | 1 (2) | 0 (0) | 3 (5) | 1 (2) |
| General Disorders and Administration Site Conditions | 6 (10) | 10 (17) | 12 (20) | 7 (13) |
| Fatigue | 2 (3) | 3 (5) | 6 (10) | 2 (4) |
| Malaise | 3 (5) | 6 (10) | 7 (12) | 2 (4) |
| Nervous System Disorders | 21 (36) | 26 (44) | 26 (43) | 14 (25) |
| Dizziness | 8 (14) | 13 (22) | 13 (22) | 3 (5) |
| Headache | 17 (29) | 20 (34) | 20 (33) | 13 (24) |
| Psychiatric Disorders | 2 (3) | 4 (7) | 7 (12) | 5 (9) |
| Mood alterations NOS | 0 (0) | 2 (3) | 4 (7) | 3 (5) |
| Skin and Subcutaneous Tissue Disorders | 4 (7) | 6 (10) | 5 (8) | 2 (4) |
| Pruritus | 1 (2) | 3 (5) | 2 (3) | 1 (2) |

*NOS indicates not otherwise specified.
[H]Intent-to-treat population is $\geq$ 5% of subjects in any treatment group.

Acute vestibular adverse events (AVAEs), including nausea, vomiting, dizziness, vertigo, and ringing in the ears, are more commonly reported during the first 5 days of treatment. On study days 1 to 5, the incidence of AVAEs is 10.2%, 23.7%, 28.3%, and 16.4% in the controlled-release-minocycline 1-, 2- and 3-mg/kg treatment groups and placebo, respectively (Table 37). The incidence for the 1-mg/kg dose group is less than half the incidence for the higher-dose groups, and overall differences among the groups are not statistically significant. Lower incidences are seen at each subsequent reporting period throughout the 84-day study; additionally, during this time, differences among the dose and placebo groups at any time point during treatment are not statistically different. Subgroup analyses of AVAEs over the 12-week treatment period indicate a dose-related increase with increasing weight (146 lb), with statistical significance (P=0.009) reached for the highest weight group only (171-225 lb). Differences in AVAEs also are more apparent as BMI increases, with statistical significance (P=0.004) noted for the highest BMI group ($\geq$25). The incidence of AVAEs is similar for males and females across the active dose groups. Although the incidence increases with higher doses in both subgroups, the overall differences for the 12-week period are not statistically significant (P$\geq$0.360).

TABLE 37

Acute Vestibular Adverse Events (Intent-to-Treat Population)*[H]

| | Controlled-Release Minocycline Hydrochloride | | | | |
|---|---|---|---|---|---|
| | 1 mg/kg, n (%) (n = 59) | 2 mg/kg, n (%) (n = 59) | 3 mg/kg, n (%) (n = 60) | Placebo, n (%) (n = 55) | Overall P Value |
| Study days 1-5 | | | | | .062 |
| $\geq$1 AVAE | 6 (10.2) | 14 (23.7) | 17 (28.3) | 9 (16.4) | |
| No AVAE | 53 (89.8) | 45 (76.3) | 43 (71.7) | 46 (83.6) | |
| Study days 6-28 | | | | | .188 |
| $\geq$AVAE | 5 (8.5) | 4 (6.8) | 9 (15.0) | 2 (3.6) | |
| No AVAE | 54 (91.5) | 55 (93.2) | 51 (85.0) | 53 (96.4) | |
| Study days 29-56 | | | | | .405 |
| $\geq$1 AVAE | 3 (5.1) | 1 (1.7) | 1 (1.7) | 0 (0) | |
| No AVAE | 53 (89.8) | 55 (93.2) | 55 (91.7) | 52 (94.5) | |
| Study days 57-84 | | | | | .620 |
| $\geq$1 AVAE | 4 (6.8) | 2 (3.4) | 2 (3.3) | 4 (7.3) | |
| No AVAE | 50 (84.7) | 51 (86.4) | 52 (86.7) | 42 (76.4) | |
| Study days 1-84 | | | | | .148 |
| $\geq$1 AVAE | 14 (23.7) | 19 (32.2) | 25 (41.7) | 14 (25.5) | |
| No AVAE | 45 (76.3) | 40 (67.8) | 35 (58.3) | 41 (74.5) | |

*AVAE indicates acute vestibular adverse event; subjects are counted once for each AVAE in each study day interval.
[H]AVAE includes $\geq$1 of the following symptoms: nausea, vomiting, dizziness, vertigo, and ringing in the ears.

Severe ADEs are reported by 1 subject (2%) in the controlled-release-minocycline 1-mg/kg treatment group and 2 subjects (3%) each in the 2- and 3-mg/kg treatment groups. One subject (2%) in the placebo group also reports a severe ADE. The severe ADEs include one report of severe headache in each of the 3 dose groups, one report of severe urticaria and severe pruritus in the 2-mg/kg treatment group, one report of severe vomiting in the 3-mg/kg treatment group, and one report each of severe fatigue and severe pruritus in the placebo group.

A total of 16 subjects have ADEs that led to treatment discontinuation; of these, 13 are possibly, probably, or definitely related to treatment. ADEs leading to subject discontinuation are shown in Table 38.

TABLE 38

Adverse Drug Events Leading to Subject Discontinuation*

| Subject | Adverse Drug Event | Severity | Relationship to Treatment | Action Taken/Outcome |
|---|---|---|---|---|
| 1-mg/kg treatment | | | | |
| 005-04 | Pruritus | Moderate | Probably | Medication discontinued; resolved |
| 005-04 | Rash NOS | Moderate | Probably | Medication discontinued; resolved |
| 005-24 | Gastrointestinal pain NOS | Moderate | Possibly | Medication discontinued; resolved |
| 011-06 | Acne aggravated | Severe | Unrelated | Medication discontinued; remedial drug therapy; resolved |
| 2-mg/kg treatment | | | | |
| 012-06 | Pruritus | Severe | Definitely | Medication discontinued; remedial drug therapy; resolved |
| 012-06 | Urticaria | Severe | Definitely | Medication discontinued; remedial drug therapy; resolved |
| 012-31 | Headache | Mild | Possibly | Medication discontinued; remedial drug therapy; resolved |
| 012-31 | Dizziness | Moderate | Possibly | Medication discontinued |
| 013-01 | Esophagitis NOS | Mild | Possibly | Medication discontinued; resolved |
| 014-14 | Urticaria NOS | Moderate | Possibly | Medication discontinued; resolved |

TABLE 38-continued

Adverse Drug Events Leading to Subject Discontinuation*

| Subject | Adverse Drug Event | Severity | Relationship to Treatment | Action Taken/Outcome |
|---|---|---|---|---|
| 015-09 | Tooth abscess | Moderate | Unrelated | Medication discontinued; resolved |
| | | 3-mg/kg treatment | | |
| 005-08 | Pruritus | Moderate | Probably | Medication discontinued; remedial drug therapy; resolved |
| 005-09 | Pruritus | Moderate | Probably | Medication discontinued; remedial drug therapy; resolved |
| 005-23 | Gastrointestinal pain NOS | Mild | Possibly | Medication discontinued; resolved |
| 005-23 | Flatulence | Mild | Possibly | Medication discontinued; resolved |
| 007-08 | Mood alteration NOS | Moderate | Possibly | Medication discontinued; resolved |
| 007-10 | Malaise | NA | Possibly | Medication discontinued; resolved |
| 007-10 | Fatigue | NA | Possibly | Medication discontinued; resolved |
| 007-10 | Dizziness | Mild | Possibly | Medication discontinued; resolved |
| 007-10 | Diarrhea NOS | Mild | Possibly | Medication discontinued; resolved |
| 007-10 | Gastrointestinal pain NOS | Mild | Possibly | Medication discontinued; resolved |
| 007-10 | Nausea | Mild | Possibly | Medication discontinued; resolved |
| 007-10 | Mood alteration NOS | Mild | Possibly | Medication discontinued; resolved |
| 011-09 | Acne aggravated | Severe | Unrelated | Medication discontinued; remedial drug therapy; resolved |
| 014-01 | Headache | Moderate | Possibly | Medication discontinued; remedial drug therapy; resolved |
| | | Placebo group | | |
| 007-07 | Gastrointestinal pain NOS | Moderate | Possibly | Medication discontinued; resolved |

*NOS indicates not otherwise specified;
NA, not available.

There is no consistent pattern of change in laboratory parameters. None of the observed changes are considered clinically significant.

In this study, after 12 weeks of treatment, inflammatory lesions decrease by approximately 50% in each of the dose groups compared with 39% in the placebo group, with no dose-dependent effect observed. The pairwise difference between the controlled-release-minocycline 1-mg/kg treatment group and the placebo group in the percentage decrease in the number of inflammatory lesions from baseline to day 84 is statistically significant (P=0.015). Thus, higher doses of controlled-release minocycline do not result in greater efficacy.

One milligram per kilogram of controlled-release minocycline delivers a low sustained release of minocycline into the systemic circulation with once-daily dosing. The reduced peak and delay in peak blood levels appears to clinically reduce the incidence of AVAEs. Higher doses of controlled-release minocycline do not result in greater efficacy for the study population. In fact, higher doses (2 and 3 mg/kg daily) are associated with more ADEs that particularly are notable during the acute period of 5 days after beginning treatment. These findings form the basis for initiating confirmatory phase 3 studies.

Example 17

A dose-ranging phase 2 study is undertaken to determine the optimal dosing regimen of the new controlled-release-minocycline formulation. The study compares once-daily doses of controlled-release minocycline 1, 2, and 3 mg/kg with placebo in a 12-week treatment protocol. (See Stewart et al., Cutis. 2006; 78(suppl 4):11-20, which is herein incorporated by reference in its entirety.)

Throughout the study, the 1-mg/kg treatment group shows a statistically significant (P=0.015) superiority to placebo in efficacy and demonstrates a safety profile comparable with the placebo. The higher doses do not provide greater efficacy than the 1-mg/kg dose but demonstrate increased rates of ADEs. Based on these results, controlled-release minocycline 1-mg/kg is chosen as the dose to be tested in the phase 3 studies.

Because the dose-ranging study and the phase 3 studies share similar populations and a common primary efficacy assessment of inflammatory lesion counts, subjects given 1 mg/kg of controlled-release minocycline in the phase 2 and phase 3 studies are pooled for safety and efficacy analysis.

The phase 2 study is a multicenter, 12-week, randomized, double-blinded, placebo-controlled dose-ranging study. The 2 phase 3 studies, which are identical in design, are independent, 12-week, randomized, double-blinded, placebo-controlled studies of controlled-release-minocycline tablets given in a 1-mg/kg daily-dosing regimen. Study drug is administered once daily in the morning from study days 1 to 84 in the phase 2 and phase 3 studies.

A total of 59 subjects (male and female) aged 12 to 30 years with moderate to severe facial acne vulgaris are given controlled-release minocycline 1 mg/kg in the phase 2 study. At baseline, subjects are required to have at least 20 and no more than 100 inflammatory facial lesions and less than 5 facial nodules or cysts. This group of subjects plus the 55 subjects given placebo in the phase 2 study are included in the pooled safety and efficacy analysis described here. Nine hundred twenty-four subjects with moderate to severe facial acne vulgaris are enrolled in the two phase 3 studies, which are conducted at 30 treatment centers in the United States. Subjects include males and females aged at least 12 years at the time of enrollment with moderate to severe facial acne. At baseline, subjects are required to have at least 25 and no more than 75 inflammatory facial lesions, no more than 2 facial nodules or cysts, and an Evaluator's Global Severity Assessment (EGSA) of moderate or severe facial acne (Table 39).

within 4 weeks, topical retinoid or retinol-containing products for facial acne within 2 weeks, topical antibiotics for facial acne within 2 weeks, topical corticosteroids applied to the face within 2 weeks, topical benzoyl peroxide for facial acne within 2 weeks, or topical over-the-counter remedies (e.g., salicylic acid) for facial acne within 2 weeks prior to the baseline visit.

After screening and baseline evaluations in the phase 2 study, subjects are randomized in a 1:1:1:1 ratio to 4 treatment groups (controlled-release minocycline 1, 2, or 3 mg/kg, or placebo); only the 1-mg/kg and placebo groups are included in this pooled analysis. After screening and baseline evaluations in the phase 3 studies, subjects are randomized in a 2:1 ratio to 2 treatment groups (controlled-release-minocycline 1-mg/kg (n=615) or placebo (n=309). Each subject study drug supply is determined by body weight and available tablet strength (Table 40). Assignment to treatment groups is stratified by the severity of acne (moderate or severe). Subjects return to the clinic on days 28, 56, and 84. Lesion counts and EGSA are performed at each visit.

TABLE 39

Evaluator's Global Severity Assessment

| Score | Grade | Inflammatory Lesions Only | Inflammatory and Noninflammatory Lesions |
|---|---|---|---|
| 0 | Clear | No evidence of papules/pustules (inflammatory lesions) | Healthy clear skin with no evidence of acne vulgaris |
| 1 | Almost clear | Rare noninflamed papules (<5) (papules must be resolving and may be hyperpigmented, though not pink-red) | Rare noninflammatory lesions present, with rare noninflamed papules (papules must be resolving and may be hyperpigmented though not pink-red) |
| 2 | Mild | Few inflammatory lesions (<10) (papules/pustules only, no nodular cystic lesions) | Some noninflammatory lesions are present with few inflammatory lesions (papules/pustules only, no nodular cystic lesions) |
| 3 | Moderate | Multiple inflammatory lesions present (25-40), many papules/pustules, and there may or may not be a few nodular cystic lesions | Noninflammatory lesions predominate, with multiple inflammatory lesions evident, several to many comedones and papules/pustules, and there may or may not be one small nodular cystic lesion |
| 4 | Severe | Inflammatory lesions are more apparent, many papules/pustules (40-75), and there may or may not be a few nodular cystic lesions | Inflammatory lesions are more apparent, many comedones and papules/pustules, and there may or may not be a few nodular cystic lesions |
| 5 | Very severe | Highly inflammatory lesions predominate, many papules/pustules, and many nodular cystic lesions | Highly inflammatory lesions predominate, variable number of comedones, many papules/pustules, and many nodular cystic lesions |

Exclusion criteria for the phase 2 and phase 3 studies are similar and include history of AVAEs such as vertigo, lightheadedness, nausea, or vomiting within 30 days prior to enrollment; history or current risk of hepatic dysfunction; history or current risk of renal dysfunction, systemic lupus erythematosus, or—in the phase 3 study only—a positive test result for antinuclear antibodies at screening; history of alcohol or drug dependency; baseline safety laboratory values outside of the reference range for liver function tests that are determined to be clinically significant; or use of oral isotretinoin within 6 months, oral antibiotics (eg, tetracyclines, erythromycin) within 4 weeks, systemic corticosteroids

TABLE 40

Controlled-Release Minocycline Hydrochloride Weight-Based Dosing Schedule

| Subject's Weight, lb (kg) | Tablet Strength, mg | Actual mg/kg Dose |
|---|---|---|
| 99-131 (45.00-59.54) | 45 | 1.00-0.76 |
| 132-199 (60.00-90.45) | 90 | 1.50-1.00 |
| 200-300 (90.91-136.36) | 135 | 1.48-0.99 |

Safety is assessed in the phase 2 and phase 3 studies at each visit by the results of physical examinations, vital sign assessments, chemistry and hematology panels, urinalysis, and review of ADEs. In the phase 3 studies, thyroid function tests and systemic evaluations (e.g., antinuclear antibodies) also are included.

In the phase 2 study, the primary efficacy assessment for the pooled analysis is the inflammatory lesion count conducted by the investigator at each study visit. Primary efficacy assessments for the phase 3 studies include the investigator-conducted inflammatory lesion count at each study visit as well as EGSA. Secondary efficacy assessments include noninflammatory and total (inflammatory and noninflammatory) lesion counts. Descriptive statistics are used to summarize baseline characteristics of subjects in the phase 2 and phase 3 studies. For continuous variables such as age, height, and weight, as well as comparisons among the treatment groups and analysis centers, statistical analyses are conducted using 2-way analysis of variance that includes treatment group and analysis center factors. Treatment groups are compared using the Cochran-Mantel-Haenszel test, stratified by center. Efficacy data for subjects who do not complete the study are Subject baseline demographic characteristics and the pooled population of the 3 studies are shown in Table 41. The mean age of the pooled population is 19.6 (19.4 years in the controlled-release-minocycline group and 20.1 years in the placebo group). The mean ages of the individual treatment groups in the phase 3 studies are similar to those of the overall population. Subjects, in the phase 2 study are, on average, younger than those in the phase 3 studies. More than 60% of the pooled subjects are younger than 18 years. Approximately 57% of subjects in the pooled population are male, 58.0% of the controlled-release-minocycline group is male, and 54.4% of the placebo group is male. Similar to the age data, gender distribution in the phase 3 studies reflects the pooled population; however, in the phase 2 population, the 1 mg/g controlled-release-minocycline treatment group is 64.4% male and the placebo group is 45.5% male. In the pooled population, 73.9% of subjects are white, 10.3% are black, and 12.1% are Hispanic. A greater percentage of the subjects in the phase 2 study than in the phase 3 studies are white.

TABLE 41

Subject Baseline Demographics (Phase 2 and Phase 3 Studies; Intent-to-Treat Population)*[H]

| | MP-0104-01 | | MP-0104-04 | | MP-0104-05 | | Pooled | | |
|---|---|---|---|---|---|---|---|---|---|
| | CRM (n = 59) | PLBO (n = 55) | CRM (n = 300) | PLBO (n = 151) | CRM (n = 315) | PLBO (n = 158) | CRM[I] (n = 674) | PLBO (n = 364) | Total (N = 1038) |
| Age, y | | | | | | | | | |
| Mean ± SD | 17.6 | 17.9 | 19.2 | 21.3 | 20.0 | 19.6 | 19.4 | 20.1 | 19.6 |
| Gender, n (%) | | | | | | | | | |
| Male | 38 (64.4) | 25 (45.5) | 171 (57.0) | 85 (56.3) | 182 (57.8) | 88 (55.7) | 391 (58.0) | 198 (54.4) | 589 (56.7) |
| Female | 21 (35.6) | 30 (54.5) | 129 (43.0) | 66 (43.7) | 133 (42.2) | 70 (44.3) | 283 (42.0) | 166 (45.6) | 449 (43.3) |
| Race, n | | | | | | | | | |
| White | 50 (84.7) | 48 (87.3) | 214 (71.3) | 97 (64.2) | 237 (75.2) | 121 (76.6) | 501 (74.3) | 266 (73.1) | 767 (73.9) |
| Black | 3 (5.1) | 2 (3.6) | 26 (8.7) | 22 (14.6) | 37 (11.7) | 17 (10.8) | 66 (9.8) | 41 (11.3) | 107 (10.3) |
| Hispanic | 5 (8.5) | 4 (7.3) | 51 (17.0) | 29 (19.2) | 26 (8.3) | 11 (7.0) | 82 (12.2) | 44 (12.1) | 126 (12.1) |
| American Indian | 0 (0) | 1 (1.8) | 0 (0) | 2 (1.3) | 0 (0) | 0 (0) | 0 (0) | 3 (0.8) | 3 (0.3) |
| Asian/Pacific Islander | 1 (1.7) | 0 (0) | 4 (1.3) | 0 (0) | 7 (2.2) | 7 (4.4) | 12 (1.8) | 7 (1.9) | 19 (1.8) |
| Other | 0 (0) | 0 (0) | 5 (1.7) | 1 (0.7) | 8 (2.5) | 2 (1.3) | 13 (1.9) | 3 (0.8) | 18 (1.5) |

*MP-0104-01, MP-0104-04 and MP-0104-05 are clinical study numbers.
[H]CRM indicates controlled-release minocycline; PLBO, placebo.
[I]Includes only subjects randomized to CRM 1 mg/kg.

imputed from the time of termination through study day 84 using last observation carried forward methodology.

The common primary efficacy endpoint for the phase 2 and phase 3 studies is the reduction in inflammatory lesion counts from baseline to day 84, which is analyzed as the change in absolute lesion count as well as the percentage change from baseline. An additional primary efficacy endpoint for the phase 3 studies is EGSA, which is based on inflammatory lesions only and defined as the proportion of subjects who achieve success (score of 0 (clear) or 1 (almost clear)). Secondary efficacy endpoints include reduction from baseline in both noninflammatory and total (inflammatory and noninflammatory) lesion counts at days 28, 56, and 84.

A total of 1038 subjects are included in the intent-to-treat populations for the pooled safety and efficacy analyses; 674 are given controlled-release minocycline 1 mg/kg and 364 are given placebo. Approximately 89% of subjects complete the 84-day treatment phase. The most frequent reasons for premature withdrawal in the controlled-release-minocycline group are lost to follow-up (3.3%) and adverse experiences (3.0%); the most frequent reasons for premature withdrawal in the placebo group are lost to follow-up (4.1%) and withdrawal of consent (4.9%).

Figure 14:
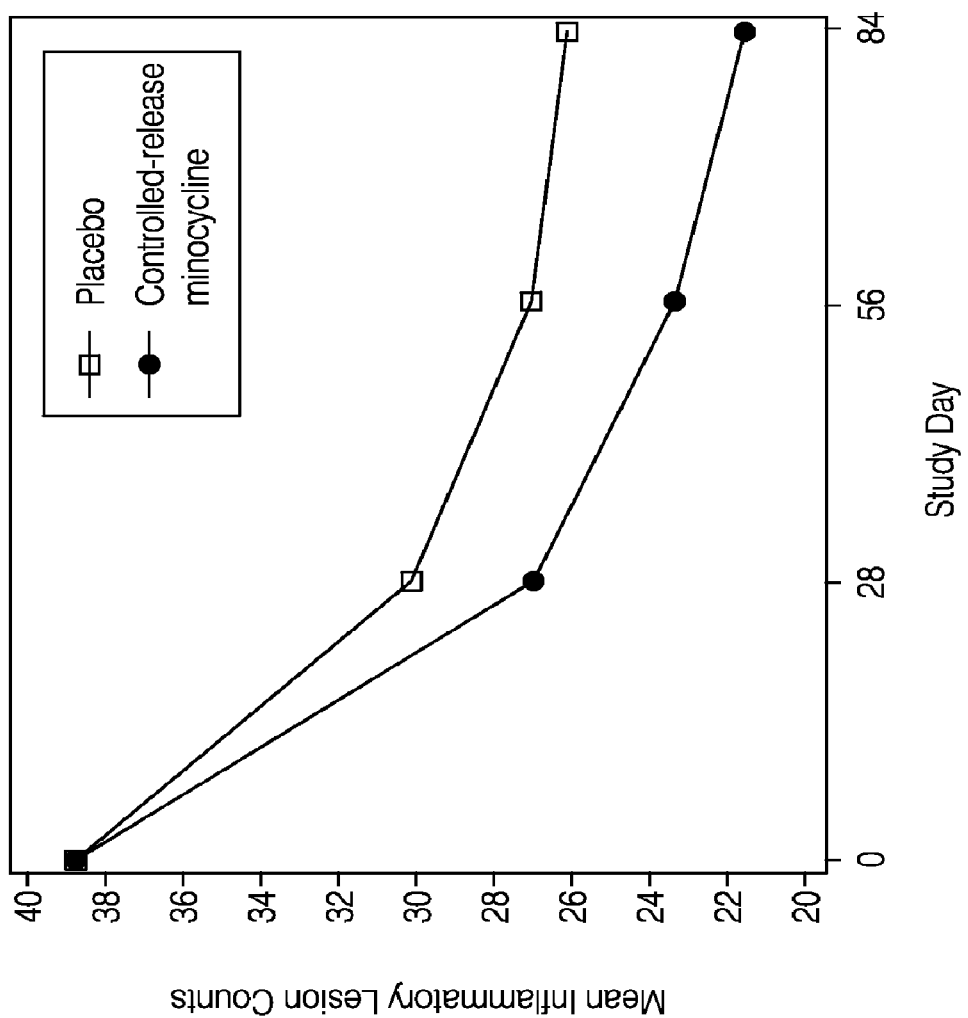
FIG. 14 shows mean inflammatory lesion counts by study day.

Analyses of the inflammatory lesion counts data from the individual studies and the pooled data for subjects given controlled-release-minocycline 1 mg/kg are shown in Table 42. Mean inflammatory lesion counts at baseline are similar between treatment groups in each study and among the 3 studies. In the individual studies, the absolute and percentage changes in the controlled-release-minocycline treatment group are greater than the placebo group. The difference between treatment groups observed in the individual studies is reflected in the pooled data: the mean absolute change at day 84 is 17.3 in the controlled-release-minocycline treatment group compared with 12.6 in the placebo group; the mean percentage change in the controlled-release-minocycline treatment group is 45.5% versus 3:2.4% in the placebo group. The treatment difference (change from baseline) is statistically significant (P<0.001) by both parametric and nonparametric techniques with no treatment-by-center effects. The inflammatory lesion counts data are displayed by study visit in FIG. 14 for controlled-release minocycline hydrochloride treatment group (n=674 at all time points) and placebo group (n=364 at all time points). Only subjects randomized to controlled-release minocycline 1 mg/kg are included in the count. The mean inflammatory lesion counts decreases over the course of all 3 studies and in the pooled data. In the pooled data, the mean percentage change in the controlled-release-minocycline treatment group is greater than the mean percentage change in the placebo group at all time points. The percentage change in lesion counts is 32.0% in the controlled-release-minocycline treatment group versus 22.8% in the placebo group at day 28; 40.8% versus 30, respectively, at day 56; and 45.5% versus 32.4% respectively, at day 84.

Weight-based dosing results in subjects receiving a range of 0.75 to 1.50 mg/kg of controlled-release minocycline. To further confirm that this dosing strategy of approximately 1 mg/kg daily is correct, a subset analysis of 472 subjects who complete all 84 days of treatment is performed of the mean reduction of inflammatory lesion counts from baseline at 4 dose quartiles. No substantial differences in lesion count reductions are seen in subjects given 0.75 to 0.98 (45.8%

TABLE 42

Primary Efficacy Endpoint: Inflammatory Lesion Counts (Phase 2 and Phase 3 Studies; Intent-to-Treat Population)*[H]

| | MP-0104-01 | | MP-0104-04 | | MP-0104-05 | | Pooled | |
|---|---|---|---|---|---|---|---|---|
| | CRM (n = 59) | PLBO (n = 55) | CRM (n = 300) | PLBO (n = 151) | CRM (n = 315) | PLBO (n = 158) | CRM[I] (n = 674) | PLBO (n = 364) |
| | Baseline | | | | | | | |
| Mean | 38.8 | 40.3 | 39.1 | 38.7 | 38.9 | 38.4 | 38.9 | 38.8 |
| P value[§] | .697 | | .789 | | .847 | | .698 | |
| | Reduction from baseline to day 84 | | | | | | | |
| Mean | 21.8 | 17.2 | 16.5 | 12.3 | 17.2 | 11.3 | 17.3 | 12.6 |
| P value[§] | .213 | | NA | | NA | | NA | |
| | Reduction from baseline to day 84, % | | | | | | | |
| Mean | 56.8 | 39.4 | 43.1 | 31.7 | 45.8 | 30.8 | 45.5 | 32.4 |
| P value[§] | .015 | | .001 | | <.001 | | <.001 | |

*MP-0104-01, MP-0104-04 and MP-0104-05 are clinical study numbers.
[H]CRM indicates controlled-release minocycline; PLBO, placebo; NA, not available.
[I]Includes only subjects randomized to CRM 1 mg/kg.
[§]P value vs placebo.

The second primary endpoint in the phase 3 studies is EGSA dichotomized as success or failure based on inflammatory lesions only (Table 43). In the phase 3 studies, the proportion of subjects with treatment success increases over the course of the study in both groups; at all time points in both studies, the proportion is greater in the controlled-release-minocycline treatment group compared with the placebo group. The pooled data reflects the results of the individual studies. The proportion of subjects with treatment success increases from 6% at day 28 to 16.6% at day 84 in the controlled-release-minocycline treatment group, and from 0.6% at day 28 to 8.7% at day 84 in the placebo group. At all 3 time points, the treatment difference is statistically significant (P=0.006 at day 28 and P<0.001 at days 56 and 84).

reduction), 0.98 to 1.23 (49.6% reduction), 1.23 to 1.37 (48.8% reduction), and 1.37 to 1.50 (45.6% reduction) mg/kg daily.

Because minocycline therapy is not considered to have an effect on noninflammatory lesions, the reduction in noninflammatory lesion counts at days 28, 56, and 84 is analyzed as a secondary efficacy endpoint. In the phase 3 studies, tests of noninferiority are performed on the percentage change in noninflammatory lesions from baseline to day 84. Table 44 displays baseline and reduction from baseline data for noninflammatory lesions. Mean noninflammatory lesion counts at baseline are comparable between treatment groups in the individual studies and in the pooled population. Generally, similar changes from baseline are seen at day 84 in all of the

TABLE 43

Evaluator's Global Severity Assessment: Inflammatory Lesions (Phase 3 Studies; Intent-to-Treat Population)*[HI]

| | Subjects in Success Category, n (%) | | | | | |
|---|---|---|---|---|---|---|
| | MP-0104-04 | | MP-0104-05 | | Pooled | |
| | CRM (n = 300) | PLBO (n = 151) | CRM (n = 315) | PLBO (n = 158) | CRM[§] (n = 615) | PLBO (n = 309) |
| Day 28 | 9 (3.0) | 0 (0) | 13 (4.1) | 2 (1.3) | 22 (3.6) | 2 (0.6) |
| P value[∥] | .031 | | .071 | | .006 | |
| Day 56 | 25 (8.3) | 5 (3.3) | 38 (12.1) | 5 (3.2) | 63 (10.2) | 10 (3.2) |
| P value[∥] | .036 | | <.001 | | <.001 | |
| Day 84 | 52 (17.3) | 12 (7.9) | 50 (15.9) | 15 (9.5) | 102 (16.6) | 27 (8.7) |
| P value[∥] | .006 | | .018 | | <.001 | |

*MP-0104-04 and MP-0104-05 are clinical study numbers.
[H]CRM indicates controlled-release minocycline; PLBO, placebo.
[I]Last observation carried forward; dichotomized as success or failure.
[§]Includes only subjects randomized to CRM 1 mg/kg.
[∥]P value vs placebo.

treatment groups across the study populations. The numbers for the percentage change from baseline at day 84 reflect only the phase 3 population for the noninferiority analyses. The results of the analyses of noninflammatory lesion data demonstrate that the effect of controlled-release minocycline on noninflammatory lesions is not inferior to the effect of placebo; that is, controlled-release-minocycline treatment statistically does not result in an exacerbation of noninflammatory processes. Clinically, controlled-release-minocycline therapy provides a numerically greater improvement in noninflammatory lesions than placebo.

baseline are similar between treatment groups in each study and among the 3 studies. In the pooled data, baseline mean total lesion counts are 84.1 in the controlled-release-minocycline treatment group and 83.9 in the placebo group. In all 3 studies, the absolute and percentage changes in the controlled-release-minocycline treatment group are greater compared with the placebo group. These results are reflected in the pooled data. The mean absolute change from baseline at day 84 is 26.8 in the controlled-release-minocycline treatment group compared with 19.2 in the placebo group. The

TABLE 44

Secondary Efficacy Endpoint; Noninflammatory Lesion Counts (Phase 2 and Phase 3 Studies; Intent-to-Treat Population)*[H]

| | MP-0104-01 | | MP-0104-04 | | MP-0104-05 | | Pooled | |
|---|---|---|---|---|---|---|---|---|
| | CRM | PLBO | CRM | PLBO | CRM | PLBO | CRM[I] | PLBO |
| Baseline | | | | | | | | |
| No. | 59 | 55 | 300 | 151 | 315 | 158 | 615 | 309 |
| Mean | 38.6 | 42.7 | 47.8 | 47.8 | 42.1 | 41.7 | 45.1 | 44.8 |
| Reduction from baseline to day 84 | | | | | | | | |
| No. | 59 | 55 | 300 | 151 | 315 | 158 | 615 | 309 |
| Mean | 12.6 | 7.7 | 9.8 | 8.7 | 8.8 | 4.4 | 9.4 | 6.6 |
| Reduction from baseline to day 84, % | | | | | | | | |
| No. | 59 | 55 | 299 | 150 | 314 | 158 | 613[§] | 308[§] |
| Mean | 18.0 | 15.7 | 15.6 | 14.3 | 13.8 | −1.6 | 14.9 | 6.3 |

*MP-0104-01, MP-0104-04, and MP-0104-05 are clinical study numbers.
[H]CRM indicates controlled-release minocycline; PLBO, placebo.
[I]Pooled data from phase 3 subjects only.
[§]Noninferiority analyses include only phase 3 subjects.

percentage change from baseline to day 84 in total lesion count is 32.9% in the controlled-release-minocycline treatment group and 22.1% in the placebo group. The treatment difference is statistically significant (P<0.001).

TABLE 45

Total (Inflammatory and Noninflammatory) Lesion Counts (Phase 2 and Phase 3 Studies; Intent-to-Treat Population)*[H]

| | MP-0104-01 | | MP-0104-04 | | MP-0104-05 | | Pooled | |
|---|---|---|---|---|---|---|---|---|
| | CRM (n = 59) | PLBO (n = 55) | CRM (n = 300) | PLBO (n = 151) | CRM (n = 315) | PLBO (n = 158) | CRM[I] (n = 674) | PLBO (n = 364) |
| Baseline | | | | | | | | |
| Mean | 77.4 | 82.9 | 86.4 | 85.4 | 83.3 | 82.8 | 84.1 | 83.9 |
| P value[§] | .731 | | NA | | NA | | NA | |
| Change from baseline to day 84 | | | | | | | | |
| Mean | 34.4 | 24.9 | 25.7 | 20.5 | 26.4 | 16.0 | 26.8 | 19.2 |
| P value[§] | .132 | | NA | | NA | | NA | |
| Change from baseline to day 84, % | | | | | | | | |
| Mean | 43.0 | 30.1 | 31.8 | 24.1 | 32.1 | 17.5 | 32.9 | 22.1 |
| P value[§] | .060 | | .015 | | <.001 | | <.001 | |

*MP-0104-01, MP-0104-04 and MP-0104-05 are clinical study numbers.
[H]CRM indicates extended-release minocycline; PLBO, placebo; NA, not available.
[I]Includes only subjects randomized to CRM 1 mg/kg.
[§]P value vs placebo.

Total (inflammatory and noninflammatory) lesion count data are presented in Table 45. Mean total lesion counts at Because the phase 2 and phase 3 studies are similar in study populations and design, safety data are pooled for analysis.

Table 46 presents the number and percentage of subjects (at least 1% of subjects in the dose groups) with treatment emergent ADEs in the pooled population. A total of 379 subjects (56.2%) given controlled-release minocycline 1 mg/kg and 197 subjects (54.1%) given placebo report treatment-emergent ADEs during the treatment phase (days 1 to 84). The most commonly reported treatment-emergent events in the controlled-release-minocycline treatment group are headache (22.6%), nausea (9.5%), fatigue (9.2%), dizziness (8.8%), diarrhea (5.2%), and pruritus (4.6%). The incidence of these ADEs is similar in the placebo group (22.8%, 11.3%, 6.6%, 4.7%, 5.8%, and 4.4%, for the 6 conditions, respectively). The majority of ADEs are mild in severity. Severe treatment-emergent ADEs are reported by 20 subjects (3%) given controlled-release minocycline and by 7 subjects (2%) given placebo. There are no reports of skin discoloration or hyperpigmentation in any of the phase 2 or phase 3 studies.

TABLE 46

Subjects with Treatment-Emergent Adverse Drug Events (Phase 2 and Phase 3 Studies; Intent-to-Treat Population)*

| | $CRM^H$ 1 mg/kg, n (%) (n = 674 | PLBO n (%) (n = 364) |
|---|---|---|
| ≧1 treatment-emergent adverse drug event | 379 (56.2) | 197 (54.1) |
| Headache | 152 (22.6) | 83 (22.8) |
| Nausea | 64 (9.5) | 41 (11.3) |
| Fatigue | 62 (9.2) | 24 (6.6) |
| Dizziness | 59 (8.8) | 17 (4.7) |
| Diarrhea | 35 (5.2) | 21 (5.8) |
| Pruritus | 31 (4.6) | 16 (4.4) |
| Malaise | 26 (3.9) | 9 (2.5) |
| Mood alteration | 17 (2.5) | 9 (2.5) |
| Vomiting | 14 (2.1) | 9 (2.5) |
| Upper respiratory tract infection | 13 (1.9) | 6 (1.6) |
| Somnolence | 13 (1.9) | 3 (0.8) |
| Urticaria | 10 (1.5) | 1 (0.3) |
| Tinnitus | 10 (1.5) | 5 (1.4) |
| Vertigo | 8 (1.2) | 3 (0.8) |
| Dry mouth | 7 (1.0) | 5 (1.4) |
| Myalgia | 7 (1.0) | 4 (1.1) |
| Other | 133 (19.7) | 85 (23.4) |

*CRM indicates controlled-release minocycline;
PLBO, placebo.
[H]Includes only subjects randomized to CRM 1 mg/kg.

The protocols define nausea, dizziness, vomiting, tinnitus, and vertigo as ADEs possibly related to vestibular function and these events are analyzed separately because minocycline is known to be associated with AVAEs. AVAEs are reported more frequently during the first 5 days of treatment in the phase 2 and phase 3 studies. Possible AVAEs in the first 5 days of treatment for each study are shown in Table 47. AVAEs are reported with approximately the same frequency (7.9%-16.4%) in the placebo group as the dose group (9.0%-10.5%).

TABLE 47

Adverse Drug Events Related to Vestibular Function During the First 5 Days of Treatment (Phase 2 and Phase 3 Studies; Intent-to-Treat Population)*[H]

| | MP-0104-01 | | MP-0104-04 | | MP-0104-05 | |
|---|---|---|---|---|---|---|
| | $CRM^I$ (n = 59) | PLBO (n = 55) | $CRM^I$ (n = 300) | PLBO (n = 151) | $CRM^I$ (n = 315) | PLBO (n = 158) |
| ≧1 acute vestibular adverse event, n (%)[§] | 6 (10.2) | 9 (16.4) | 27 (9.0) | 12 (7.9) | 33 (10.5) | 17 (10.8) |

*MP-0104-01, MP-0104-04 and MP-0104-05 are clinical study numbers.
[H]CRM indicates extended-release minocycline; PLBO, placebo.
[I]Includes only subjects randomized to CRM 1 mg/kg.
[§]Nausea, dizziness, vomiting, vertigo, and tinnitus (ringing in the ears).

Of the 674 subjects treated with controlled-release minocycline 1 mg/kg in the pooled phase 2 and phase 3 studies, 20 subjects (3%) have ADEs that lead to treatment discontinuation: pruritus (7), urticaria (7), rash (3), aggravated acne (1), and fatigue (2). Other ADEs are gastrointestinal tract pain, diarrhea, nausea, headache, arthralgia, facial swelling, dizziness, migraine, insomnia, mood alteration, upper respiratory tract infection, neck pain, hypoesthesia, paresthesia, and dermatitis medicamentosa, ADEs such as urticaria, rash, dermatitis, and pruritus occur in a small number of subjects but account for a disproportionate number of discontinuations. In the dose group, some form of skin eruption (urticaria, rash, dermatitis) or pruritus is reported in 1.5% and 4.6% of subjects, respectively; however, 17 of 38 subjects who discontinue during the phase 2 and phase 3 studies reported one or both of these ADEs.

Pruritus occurs with about the same frequency in the dose and placebo groups, while skin eruptions occur slightly more often in the controlled-release-minocycline treatment group. Only one report of urticaria is considered severe, and none of the pruritus reports are severe. One possible explanation for the incidence of pruritus in both groups is that the trials are conducted during the winter months, when skin dryness is exacerbated by central heating and the seasonal low humidity. This explanation may account for some cases of skin eruptions, with the exception of urticaria. For the subjects who discontinue because of urticaria, the discontinuations generally occur within the first 2 to 3 weeks of therapy and resolved after treatment is discontinued.

No changes in vital signs or physical findings are reported. Analysis of the mean changes from baseline to day 84 for the pooled study populations in laboratory parameters, as well as the frequency of shifts in and out of reference ranges for the laboratory parameters from baseline to day 84, reveal no evidence of clinically significant changes. Specifically, there are no treatment-dependent effects on clinical laboratory parameters associated with liver or thyroid function observed at the end of the phase 2 and phase 3 studies. In each of the phase 3 studies, one subject has a positive antinuclear antibody at the end of treatment. One subject develops a weakly positive antinuclear antibody after experiencing flu symptoms, and one develops a weakly positive antinuclear antibody during follow-up after discontinuation of controlled-release minocycline. The subjects are asymptomatic and the clinical significance of the clinical findings is unclear.

The rates of incidence of ADEs also are investigated by age, gender, and race. None of the common ADEs are more common in the pediatric population (aged 12-17 years) than the adult population (aged 18 years). The incidence of dizziness among females taking controlled-release minocycline is 11.8% compared with 4.4% in females taking placebo. Seven females (2.7%) in the controlled-release-minocycline treatment group report urticaria compared with 1 female (0.7%) in the placebo group. Headache and fatigue are observed more frequently in females than males in both treatment groups. Other common ADEs are not seen more frequently in one gender compared with the other. None of the common ADEs are more frequent in one racial group than another.

The controlled-release minocycline used in this study is a modified formulation of minocycline with lower $C_{max}$ and $T_{max}$, lowering the amount and rate of drug crossing the blood-brain barrier into the central nervous system, thus lowering the incidence of AVAEs while maintaining desired minocycline efficacy. These pharmacokinetic studies confirm that the modified formulation of minocycline has the desired pharmacokinetic properties; the subsequent phase 2 dose-finding study demonstrate that about 1 mg/kg is an effective dose, with potential for desired improvement in AVAEs. The placebo-controlled phase 3 studies show that controlled-release-minocycline administered daily for 12 weeks at a dose of approximately 1 mg/g is safe and effective in the treatment of inflammatory lesions of acne vulgaris.

Similar study design, subject populations, and 1-mg/kg dose groups in the phase 2 and phase 3 studies allowed pooling of the data for the overall safety and efficacy analysis. Data from 1038 subjects (674 given controlled-release minocycline 1 mg/kg; 364 given placebo) with moderate to severe acne vulgaris are available for the pooled analysis. Results of the pooled analysis confirm the results of the individual studies for the primary efficacy endpoints. Controlled-release minocycline at 1 mg/kg is shown to be significantly ($P=0.015$) more effective than placebo as seen by reductions in both mean inflammatory lesion counts and EGSA for inflammatory lesions. Throughout the 12-week treatment period, the mean inflammatory and total (inflammatory and noninflammatory) lesion counts continues to decrease and EGSA, based either on inflammatory lesions only or on inflammatory and noninflammatory lesions, continues to improve.

The high incidence and severity of reported ADEs-particularly vestibular related-associated with minocycline use may have been exacerbated by the high doses that traditionally have been given. This pooled analysis of more than 1000 subjects given controlled-release minocycline 1 mg/kg indicates an incidence of AVAEs similar to the incidence in subjects given placebo.

Example 18

A batch of 90 mg Minocycline hydrochloride modified release tablets is prepared as follows in 3 sublots of 115 kg then commingled to produce a 345 kg batch (appropriate pharmaceutical manufacturing quality control procedures are used throughout): 31.050 kg of hydroxypropyl methylcellulose (Hypromellose Type 2910, Methocel E50 Premium LV), minocycline hydrochloride (free base Minocycline equivalent amount=28.875 kg), and 43.7 kg of de-agglomerated lactose monohydrate (#316 Fast-Flo) are charged into a high shear granulator and are pre-blended using the impeller only. The resulting pre-blend is then wet granulated by spraying 34.212 kg of purified water targeting 5000 g/min addition rate with the chopper and impeller on. At the completion of the wet granulation, the granulation is wet massed using the impeller and chopper. The resulting wet-massed material is wet-sized through a comminutor mill. The resulting wet-massed granulation is then dried in a fluid bed dryer at a inlet temperature of 65 degrees Celsius until a loss on drying (LOD) of 1.5% to 2.5% (target 2.0%). The resultant dried granulation is sized through a comminutor mill and collected in a tote.

Using the percent yield for the milled dried granulation sublot, the amounts of the remaining excipients, lactose monohydrate (11.787 kg), colloidal silicon dioxide (862.5 g) and magnesium stearate (1.725 kg), are adjusted to compensate for loss during granulation and milling. The colloidal silicon dioxide and lactose are charged into an appropriately sized V-blender and blended to from a pre-mix. This pre-mix is passed through a comminutor mill and collected into the tote containing the dried milled granulation and blended. Approximately 5 kg of this material is collected and added to a suitable V-blender with the adjusted magnesium stearate and blended. This blend is then passed through a comminutor mill and added to the tote. The material in the tote is then blended. This process is then repeated until all three granulation/blend sublots have been separately manufactured. All three blends are then charged to a tote and mixed. This produces the final blend used to form the tablet formulation.

The final blend tablet formulation is then compressed on a rotary tablet press using caplet shaped tooling (0.2343"× 0.6250) with a target weight of 400 mg. The caplets are then de-dusted and passed through a metal detector. The tablets are then coated in three 115 kg sub-lots, to a target weight gain of 14.0 mg/caplet with Opadry II Yellow Coating Solution (18% solids) in a 48" coating pan.

The various compositions and methods described above provide a number of ways to carry out the invention. It is to be understood that not necessarily all objectives or advantages described can be achieved in accordance with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. For example, one or more of the disclosed features or embodiments may be combined with one or more other features or embodiments. Accordingly, the invention is not intended to be limited by the specific disclosures of preferred embodiments herein.

What is claimed is:
1. A method for the treatment of acne in a person using an oral dosage form, comprising:
  determining the body weight of the person; and
  selecting the dosage form based on the body weight of the person so that the dosage form provides the person, without an initial load dose, 0.7 mg/kg/day to 1.3 mg/kg/day of the minocycline or a pharmaceutically acceptable salt thereof by a once daily administration,
  wherein the dosage form comprises:
    minocycline or the pharmaceutically acceptable salt thereof; and
    an amount of a carrier, said carrier being a controlled-release carrier that provides a release rate in gastric fluid of the minocycline or a pharmaceutically acceptable salt thereof that is either 25% to 52% within 1 hour, 53% to 89% within 2 hours, and at least 90% at

4 hours, or 30% to 52% within 1 hour, 53% to 84% within 2 hours, and at least 85% at 4 hours.

2. The method of claim 1, wherein said carrier comprises at least one ingredient selected from the group consisting of hydroxypropylmethylcellulose, hydroxypropylcellulose, and polyvinylpyrrolidone.

3. The method of claim 1, wherein said carrier is present in the range of 20% to 30%, by weight based on the total weight of the dosage form.

4. The method of claim 1, wherein the pharmaceutically acceptable salt comprises minocycline hydrochloride.

5. The method of claim 1, wherein the 0.7 mg/kg/day to 1.3 mg/kg/day of the minocycline or the pharmaceutically acceptable salt thereof is about 1 mg/kg/day.

6. The method of claim 5, wherein the minocycline is present in an amount selected from the group consisting of 45 mg, 90 mg and 135 mg.

7. The method of claim 6, wherein said carrier further includes a slow dissolving carrier.

8. The method of claim 1, wherein said carrier includes a slow dissolving carrier.

9. The method of claim 7, wherein when the minocycline is present in an amount of 45 mg or 90 mg, said slow dissolving carrier is 26% to 28% by weight based on the total weight of the dosage form.

10. The method of claim 7, wherein when the minocycline is 135 mg, said slow dissolving carrier is 22% to less than 25% by weight based on the total weight of the dosage form.

11. The method of claim 8, wherein said carrier further includes a fast dissolving carrier.

12. The method of claim 11, wherein said fast dissolving carrier includes an intragranular fast dissolving carrier and an extragranular fast dissolving carrier.

13. The method of claim 12, wherein said intragranular fast dissolving carrier and said slow dissolving carrier are each in an amount greater than said extragranular fast dissolving carrier.

14. The method of claim 1, further comprising a film coat of 2 to 3% of the total weight of the dosage form with coating.

* * * * *